United States Patent
Couffin et al.

(10) Patent No.: US 9,463,248 B2
(45) Date of Patent: Oct. 11, 2016

(54) MATERIAL, METHOD FOR PREPARING SAME, AND USES THEREOF

(71) Applicant: COMMISSARIAT À L'ÉNERGIE ATOMIQUE ET AUX ÉNERGIES ALTERNATIVES, Paris (FR)

(72) Inventors: Anne-Claude Couffin, Monestier-de-Clermont (FR); Thomas Delmas, Grenoble (FR); Emilie Heinrich, Sassenage (FR); Isabelle Texier-Nogues, Grenoble (FR); Jean-Sébastien Thomann, Longwy (FR); Véronique Mourier, Saint Jean de Moirans (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/389,432

(22) PCT Filed: Apr. 2, 2013

(86) PCT No.: PCT/EP2013/056923
§ 371 (c)(1),
(2) Date: Sep. 30, 2014

(87) PCT Pub. No.: WO2013/144369
PCT Pub. Date: Oct. 3, 2013

(65) Prior Publication Data
US 2015/0057374 A1    Feb. 26, 2015

(30) Foreign Application Priority Data
Mar. 30, 2012  (FR) .................................... 12 52941

(51) Int. Cl.
| | | |
|---|---|---|
| A61K 47/24 | (2006.01) | |
| A61K 47/34 | (2006.01) | |
| A61K 47/48 | (2006.01) | |
| A61K 47/18 | (2006.01) | |
| A61K 9/107 | (2006.01) | |
| A61K 47/20 | (2006.01) | |

(52) U.S. Cl.
CPC ............... *A61K 47/24* (2013.01); *A61K 9/107* (2013.01); *A61K 47/18* (2013.01); *A61K 47/20* (2013.01); *A61K 47/34* (2013.01); *A61K 47/488* (2013.01); *A61K 47/48192* (2013.01)

(58) Field of Classification Search
None
See application file for complete search history.

(56) References Cited

U.S. PATENT DOCUMENTS

| | | | |
|---|---|---|---|
| 2008/0311207 A1* | 12/2008 | Varshney | A61K 9/1075 424/489 |
| 2013/0121933 A1* | 5/2013 | Novack | A61Q 1/06 424/59 |
| 2013/0251629 A1* | 9/2013 | Delmas et al. | 424/1.11 |

FOREIGN PATENT DOCUMENTS

| | | | |
|---|---|---|---|
| WO | WO 2010/018223 A1 | 2/2010 | |
| WO | WO 2011/101602   * | 8/2011 | ............. A61K 9/107 |
| WO | WO 2011/101602 A1 | 8/2011 | |
| WO | WO 2013/039819   * | 3/2013 | ............. C01B 31/02 |

OTHER PUBLICATIONS

International Search Report dated Jul. 5, 2013 issued in corresponding International patent application No. PCT/EP2013/056923.
French Search Report dated Nov. 9, 2012 issued in corresponding French Application No. 1252941.
Meng F et al.: "Reduction-sensitive polymers and bioconjugates for biomedical applications", Biomaterials, Elsevier Science Publishers BV., Barking, GB, vol. 30, No. 12, Apr. 1, 2009, pp. 2180-2198, XP025990543.
Shen J et al.: "Mucoadhesive effect of thiolated Peg stearate and its modified NLC for ocular drug delivery", Journal Controlled Release, Elsevier, Amsterdam, NL, vol. 137, No. 3, Aug. 4, 2009, pp. 217-223, XP026223534.
Kovacevic A et al.: "Polyhydroxy surfactants for the formulation of lipid nanoparticles (SLN and NLC): Effects on size, physical stability and particle matrix structure", International Journal of Pharmaceutics, Elsevier BV, NL vol. 406, No. 1, Dec. 27, 2010, pp. 163-172, XP028363295.
Delmas T et al.: "Preparation and characterization of highly stable lipid nanoparticles with amorphous core of tuneable vixcosity" Journal of Colloid and Interface Science 2011 Academic Press Inc. USA LNKD-DOI:10.1016/J.JCIS.2011.04.080, vol. 360, No. 2, Aug. 15, 2011, pp. 471-481, XP002686819.

* cited by examiner

*Primary Examiner* — Brian Gulledge
(74) *Attorney, Agent, or Firm* — B. Aaron Schulman, Esq.; Stites & Harbison, PLLC.

(57) ABSTRACT

A material including a continuous aqueous phase and a dispersed phase in the form of droplets containing an amphiphilic lipid and a surfactant having the following formula (I):

$$(L_1\text{-}X_1\text{—}H_1\text{—}Y_1)_v\text{-}G\text{-}(Y_2\text{—}H_2\text{—}X_2\text{-}L_2)_w \qquad (I),$$

wherein:
$L_1$ and $L_2$ independently represent lipophilic groups,
$X_1$, $X_2$, $Y_1$, $Y_2$ and G independently represent a linking group,
$H_1$ and $H_2$ independently represent hydrophilic groups including a polyalkoxylated chain,
v and w are independently an integer from 1 to 8,
wherein the droplets of the dispersed phase are covalently bonded by the surfactant having the formula (I). The invention also relating to the method for preparing the same and to the uses thereof.

19 Claims, 4 Drawing Sheets

MATERIAL, METHOD FOR PREPARING SAME, AND USES THEREOF

CROSS REFERENCE TO RELATED APPLICATIONS

The present application is a 35 U.S.C. §371 National Phase conversion of PCT/EP2013/056923, filed Apr. 2, 2013, which claims benefit of French Application No. 12 52941, filed Mar. 30, 2012, the disclosure of which is incorporated herein by reference. The PCT International Application was published in the French language.

TECHNICAL FIELD OF THE INVENTION

The present invention relates to a material comprising of a continuous aqueous phase and a dispersed phase, dispersed in the form of droplets bonded to each other in a covalent manner, and the uses thereof as a membrane, diaphragm, valve, coating, chemical detector or sensor or for the delivery of agents of interest.

BACKGROUND OF THE INVENTION

The literature describes materials that are water based and whose physical form and properties may be modulated, thereby making possible various applications in fields that are widely varied. For example, mention may be made of hydrogels, which are three dimensional networks based on polymers having a number of applications in the food, agricultural and medical fields (contact lenses, delivery of therapeutic agent, breast implant, dressing, coating for prostheses) (Hamidi et al; Advanced Drug Delivery Reviews, 60, 2008, 1638).

The present invention provides a water based material that is an alternative to hydrogels and having the same advantageous properties, since it is possible to modulate and maintain a physical form and to adapt the physical and chemical properties of the material based on the desired application.

Furthermore, the patent application WO 2011/101602 describes an oil in water nano emulsion in form of a gel for the delivery of hydrophilic and lipophilic agents of interest. The three dimensional network of this gel is formed by the droplets bonded to each other by non covalent interactions. However, this gel is relatively fluid, and after being formed, it fails to sufficiently maintain its form. In addition, this gel when placed in the presence of an aqueous phase (and in particular physiological liquid during in vivo administration thereof) disaggregates rapidly and the three dimensional network of the gel is destroyed. Furthermore, these nano emulsions require high proportions of dispersed phase. These three disadvantages constitute an obstacle for many applications of a gel.

SUMMARY OF THE INVENTION

The present invention provides a material in the form of an oil in water emulsion which does not have these above noted disadvantages. The material is able to take form, remain therein and resist dilution in water. It can thus be used in very diverse applications, and in particular in applications that require the presence of an aqueous phase.

[Material]

According to a first object, the invention relates to a material comprising of a continuous aqueous phase and a dispersed phase, dispersed in the form of droplets containing an amphiphilic lipid and a surfactant having the following formula (I):

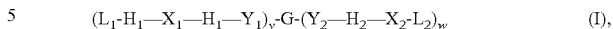

$$(L_1\text{-}H_1\text{—}X_1\text{—}H_1\text{—}Y_1)_v\text{-}G\text{-}(Y_2\text{—}H_2\text{—}X_2\text{-}L_2)_w \qquad (I),$$

wherein:
$L_1$ and $L_2$ independently represent lipophilic groups,
$X_1$, $X_2$, $Y_1$, $Y_2$ and G independently represent a linking group,
$H_1$ and $H_2$ independently represent hydrophilic groups including a polyalkoxylated chain,
v and w are independently an integer from 1 to 8,
the droplets of the dispersed phase being bonded to each other in a covalent manner by the surfactant having the formula (I).

The material is present in the form of an oil in water emulsion in which the droplets of the dispersed phase are bound to each other by covalent bonding. The emulsion may be single or multiple, in particular by including in the dispersed phase a second aqueous phase.

DEFINITIONS

Within the scope and context of the present patent application, the term "dispersed phase" is used to refer to oil droplets comprising the optional oil/the optional solubilising lipid/the amphiphilic lipid/the optional co-surfactant/the optional lipophilic agent of interest/surfactant having the formula (I). The dispersed phase is generally free of aqueous phase. The material is typically free of liposomes.

The term "droplet" encompasses both the actual liquid oil droplets as well as the solid particles derived from emulsions of the oil-in-water type in which the oily phase is solid.

The droplets of the material are advantageously monodisperse. The standard deviation between the minimum and maximum diameters of the droplets relative to the mean diameter is generally less than or equal to 30%, preferably 20%. The material is generally presented in the form of an oil in water nano emulsion: the mean diameter of the droplets of the dispersed phase is preferably from 20 nm to 200 nm, notably from 40 nm to 150 nm and in particular from 50 nm to 120 nm. These diameters are measured by means of light scattering. It is also possible to obtain the size of droplets by means of transmission electron microscopy (TEM), cryogenic transmission electron microscopy (cryo TEM) or even by atomic force microscopy (AFM). Diameters measuring less than 20 nm and more than 200 nm are difficult to obtain in practice.

The term "lipid" is used within the context of the discussion in this description to refer to all fatty substances or substances containing fatty acids present in the fats of animal origin and in plant oils. They are hydrophobic or amphiphilic molecules mainly formed of carbon, hydrogen and oxygen and having a density lower than that of water. The lipids may be in the solid state at ambient temperature (25° C.), as in waxes, or in the liquid state, as in oils.

The term "amphiphilic" is used to refer to a molecule possessing a hydrophobic part and a hydrophilic part, for example a hydrophobic apolar part and a hydrophilic polar part.

The term "phospholipid" is used to refer to lipids possessing a phosphate group, in particular phosphoglycerides. Most often, phospholipids include a hydrophilic end formed by the phosphate group possibly substituted and two hydrophobic ends formed by the fatty acid chains. Among the phospholipids, mention should be made in particular of phosphatidyl choline, phosphatidyl ethanolamine, phosphatidyl inositol, phosphatidyl serine and sphingomyelin.

The term "lecithin" is used to refer to phosphatidyl choline, that is to say a lipid formed from a choline, a phosphate, a glycerol and two fatty acids. It covers in a broader sense the phospholipids derived from living systems of plant or animal origin, as long as they primarily consist of phosphatidyl choline. These lecithins generally consist of mixtures of lecithins carrying different fatty acids.

The term "surfactant" is used to refer to compounds having an amphiphilic structure which gives them a special affinity for oil/water type and water/oil type interfaces which gives them the ability to reduce the free energy of these interfaces and thus to stabilise the dispersed systems.

The term "co-surfactant" is used to refer to a surfactant acting in addition to another surfactant in order to further reduce the energy of the interface.

The term "lipophilic" agent of interest, is used to refer to an agent of interest that is predominantly, preferably completely, in the dispersed phase, or inside of or on the surface of the droplets. A lipophilic agent of interest has affinities for oily compounds (fats, oils, waxes, etc) and apolar solvents (toluene, hexane, etc). The forces that enable the solubilisation of the lipophilic agent of interest are predominantly London forces (Van der Waals interactions). A lipophilic agent of interest has a high oil/water partition coefficient.

The term "hydrophilic" agent of interest, is used to refer to an agent of interest that is predominantly, preferably completely, in the continuous aqueous phase. Its solubility in water is generally greater than 1% by weight. The solubilisation in water of the hydrophilic agents of interest generally comes from the hydrogen and/or ionic bonds between the hydrophilic agents of interest and water.

The term "fatty acid" is used to refer to aliphatic carboxylic acids having a carbon chain of at least 4 carbon atoms. Natural fatty acids have a carbon chain of 4 to 28 carbon atoms (generally an even number). Long chain fatty acids refer to those with chains that are 14 to 22 carbon atoms long and very long chain fatty acids refer to those having more than 22 carbon atoms.

The term "hydrocarbon chain" is used to refer to a chain composed of atoms of carbon and hydrogen, whether saturated or unsaturated (double or triple bond). Preferred hydrocarbon chains are alkyl or alkenyl.

The term "alkylene" is used to refer to a divalent aliphatic saturated hydrocarbon group, that is linear or branched, preferably linear.

The term "activated ester" is used to refer to a group having the formula —CO-LG, and the term "activated carbonate" is used to refer to a group having the formula —O—CO-LG, where LG represents a good leaving group in particular selected from among a bromine, a chlorine, an imidazolyl, a pentafluorophenolate, a pentachlorophenolate, a 2,4,5-trichlorophenolate, 2,4,6-trichlorophenolate, an —O-succinimidyl group, an —O-benzotriazolyl, —O-(7-aza-benzotriazolyl) and an —O-(4-nitrophenyl) group.

Surfactant Having the Formula (I)

The material according to the invention includes a surfactant having the formula (I) which is located partially in the continuous aqueous phase and partially in the dispersed phase. Indeed, the surfactant having the formula (I) of the material according to the invention comprises two lipophilic groups ($L_1$ and $L_2$) and two hydrophilic groups ($H_1$ and $H_2$). The hydrophilic groups are located predominantly at the surface of the droplets, in the continuous aqueous phase while the lipophilic groups are located in the droplets of the material.

More precisely, the lipophilic group $L_1$ is located in certain droplets, and the group $L_2$ is in the adjacent droplets. The droplets of the material according to the invention are bound to each other in a covalent manner by the —($X_1$—$H_1$—$Y_1$)$_v$-G-($Y_2$—$H_2$—$X_2$)$_w$— group of the surfactant having the formula (I). FIGS. 1 and 2 illustrate the positioning of the surfactant having the formula (I), respectively when v and w represent 1 and when v and w represent 2.

The $X_1$ and $X_2$ groups are linking groups linking the lipophilic and hydrophobic groups. The G group is a linking group between at least two [lipophilic-hydrophilic] parts of the surfactant having the formula (I). The $Y_1$ and $Y_2$ groups are linking groups linking the G group to the [lipophilic-hydrophilic] parts.

The material according to the invention can advantageously be set in form (for example, by placing it in a mould or a container having a given shape or form), and can remain in the form desired according to the desired application.

Furthermore the material is resistant to dilution in an aqueous phase. More specifically, when an aqueous phase is added to the material according to the invention, it remains in form and is not diluted. In the medium, one observes on the one hand the material comprising the droplets, and on the other hand, an aqueous phase substantially free of droplets.

Without intending to be bound to any particular theory, it appears that the properties of the material according to the invention can be explained by the presence of covalent bonds between the droplets, which serves to confer a very strong cohesion therebetween.

In one embodiment, in the Formula (I) mentioned above:
$L_1$ and $L_2$ are independently selected from among:
  a R or R—(C═O)— group, where R represents a linear hydrocarbon chain containing from 11 to 23 carbon atoms,
  an ester or an amide of fatty acids containing from 12 to 24 carbon atoms and of phosphatidyl ethanolamine, such as distearyl phosphatidyl ethanolamine (DSPE), and
  a poly(propylene oxide), and/or
$X_1$, $X_2$, $Y_1$ and $Y_2$ are independently selected from among:
  a single bond,
  a Z group selected from among —O—, —NH—, —O(OC)—, —(CO)O—, —(CO)NH—, —NH(CO)—, —O—(CO)—O—, —NH—(CO)—O—, —O—(CO)—NH— et —NH—(CO)—NH,
  a Alk group being an alkylene containing from 1 to 6 carbon atoms, and
  a Z-Alk, Alk-Z, Alk-Z-Alk or Z-Alk-Z group, where Alk and Z are as defined here above and where the two Z groups of the Z-Alk-Z group are identical or different, and/or
$H_1$ and $H_2$ are independently selected from a poly(ethylene oxide) typically comprising from 3 to 500 ethylene oxide units, preferably from 20 to 200 ethylene oxide units, and/or
G includes at least one G' group having one of the following formulas (the $Y_1$ and $Y_2$ groups being linked to the left and right of the formulas described here below):

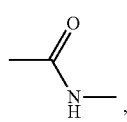

(XI)

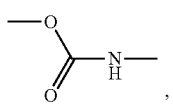 (XII)

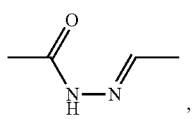 (XIII)

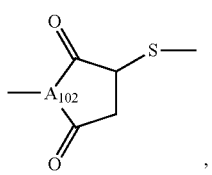 (XIV)

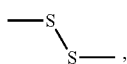 (XV)

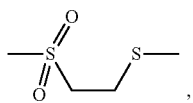 (XVI)

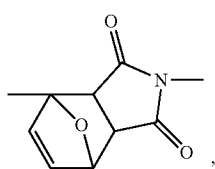 (XVII)

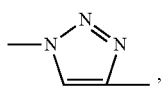 (XVIII)

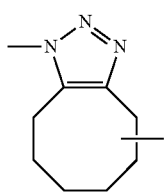 (XVIII')

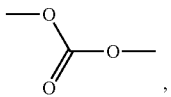 (XIX)

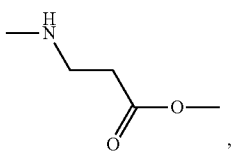 (XX)

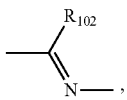 (XXI)

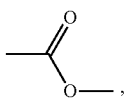 (XXII)

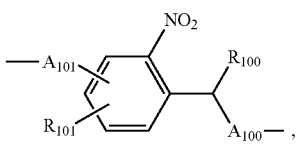 (XXIII)

—O—, (XXV)

—NH— (XXVI)

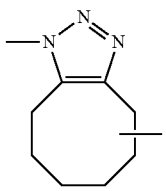 (XXVII)

where $A_{102}$ represents CH or N, $R_{102}$ represents H or a linear hydrocarbon chain containing from 1 to 6 carbon atoms, $A_{101}$ represents —O—, —NH—(CO)— ou —O(CO)—, $R_{100}$ represents H or a methyl, $A_{100}$ represents —O— or —NH— and $R_{101}$ represents H, Me or —OMe.

The formula understood to indicate that the $Y_2$ group may be linked to any one of the six atoms of cyclooctyl and the formula

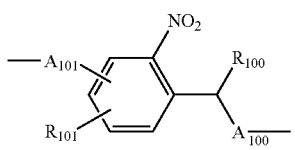

is understood to indicate that the $A_{101}$ and $R_{101}$ group may be linked to any one of the four atoms of phenyl.

In particular, v and w independently represent 1 or 2. v and w preferably represent 1.

The G group may include one or more of the G' groups defined here above.

Thus, in a first embodiment, the G group is constituted of a G' group. In this embodiment, in formula (I), v and w represent 1.

In a second embodiment, the G group has the formula -G'-$Y_3$-G'- wherein:
$Y_3$ represents a linking group, in particular selected from among:
a single bond,
a Z group selected from among —O—, —NH—, —O(OC)—, —(CO)O—, —(CO)NH—, —NH(CO)—, —O—(CO)—O—, —NH—(CO)—O—, —O—(CO)—NH— et —NH—(CO)—NH,
a Alk group being an alkylene containing from 1 to 6 carbon atoms, and
a Z-Alk, Alk-Z, Alk-Z-Alk or Z-Alk-Z group, where Alk and Z are as defined here above and where the two Z groups of the Z-Alk-Z group are identical or different,
each of the G' groups independently represents a group having the formula (XI) to (XXVI) described here above, and preferably, the two G' groups of the formula -G'-$Y_3$-G'- are identical.

In this embodiment, in the formula (I), v and w represent 1. This embodiment is particularly advantageous when the two G' groups are identical and include a cleavable function. Indeed, it is then sufficient to cleave only one of the two functions in order to break the covalent bonds between the droplets of the material.

In a third embodiment, the G group is a dendrimer comprising (v+w) G' groups. The G group may in particular be a dendrimer comprising several G' groups, such as a dendrimer including a polyamidoamine (PAMAM) group. For example, the G group may have one of the following formulas (XXX) to (XXXIII), which include:

4 G' groups having the formula (XXVI). v and w represent 2.

4 G' groups having the formula (XXIV), where $R_{101}$ represents —O-Me, $A_{101}$ represents —NH—, $R_{100}$ represents a methyl and $A_{100}$ represents —NH—. v and w represent 2.

4 G' groups having the formula (XIV). v and w represent 2.

16 G' groups having the formula (XXVI). v and w represent 8.

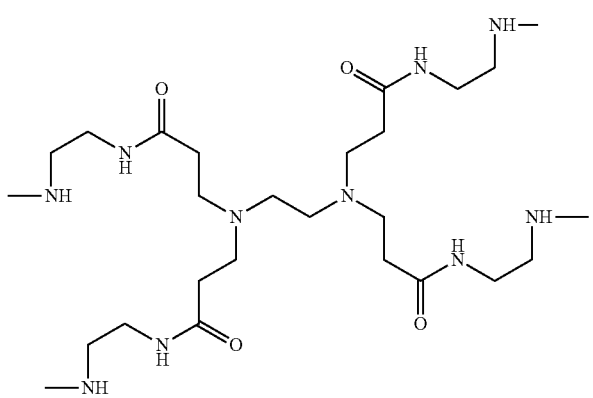

(XXX)

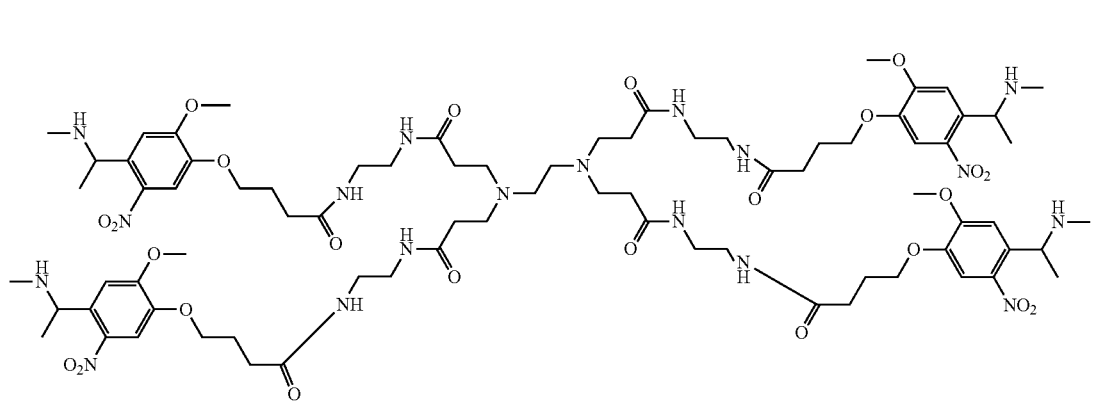

(XXXI)

(XXXII)
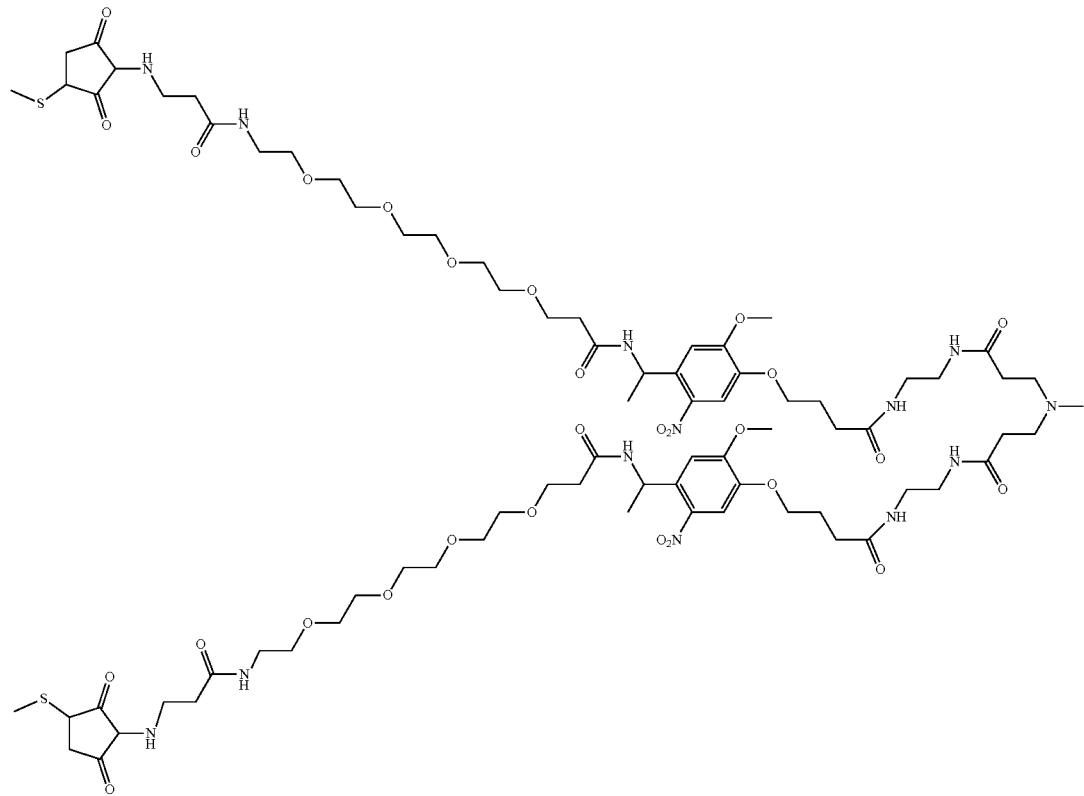
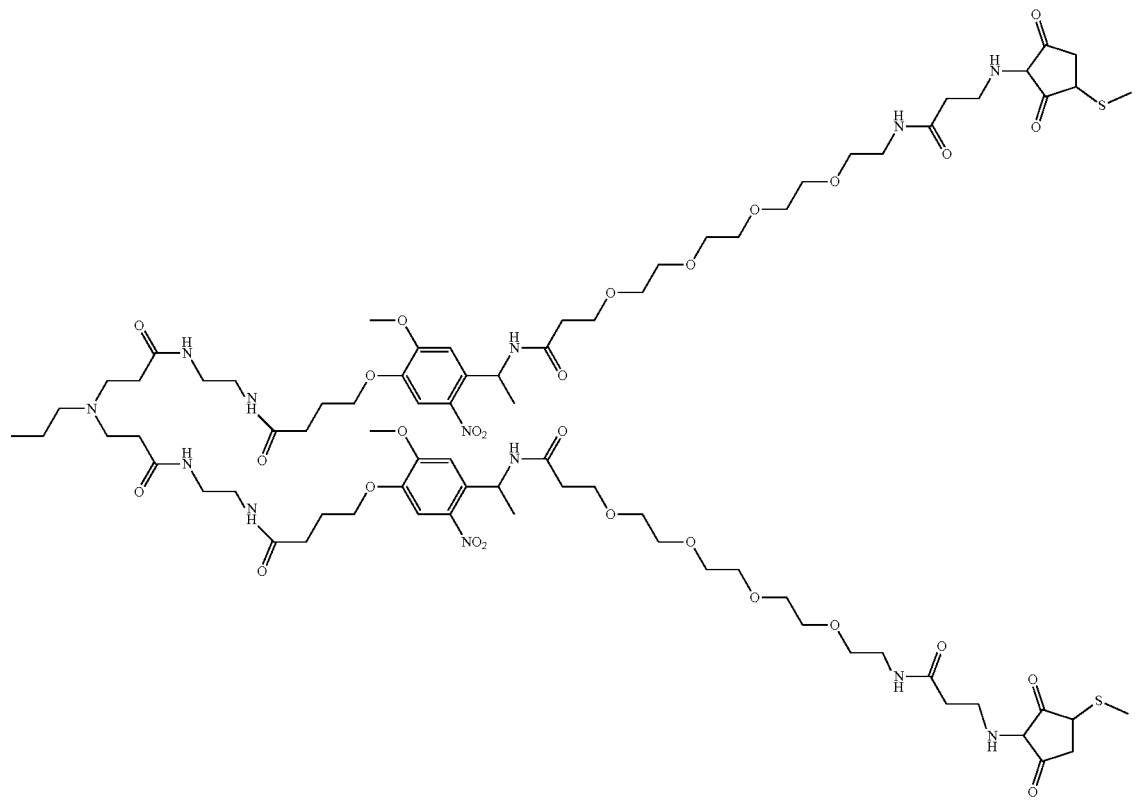

-continued (XXXIII)

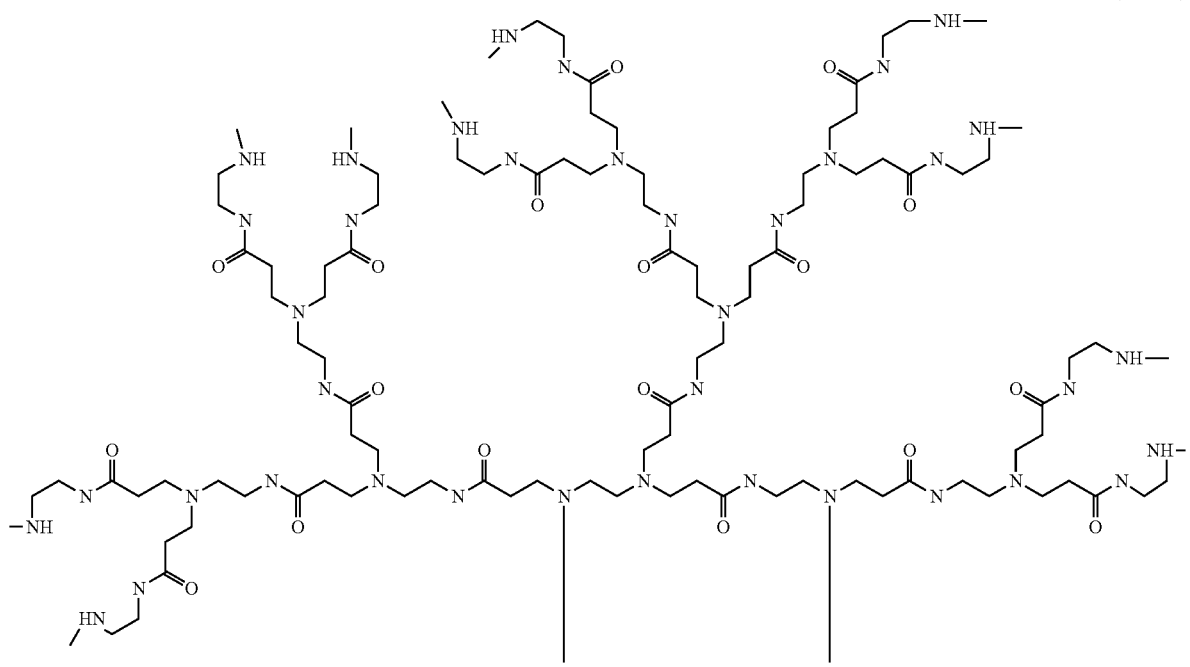

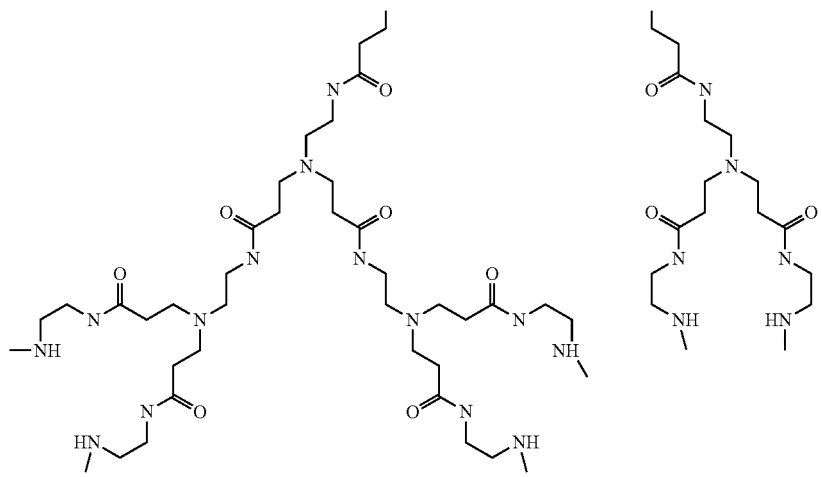

When $L_1$ and/or $L_2$ represent a R—(C=O)— group, wherein R represents a linear hydrocarbon chain containing from 11 to 23 carbon atoms, $L_1$ and/or $L_2$ represent groups derived from a fatty acid containing from 12 to 24 carbon atoms.

The statement "$L_1$ and $L_2$ represent an ester or an amide of fatty acids containing from 12 to 24 carbon atoms and of phosphatidyl ethanolamine" is understood to mean that they represent a group having the formula:

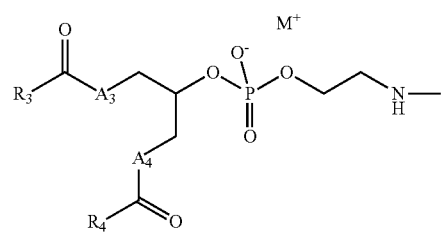

wherein
- $R_3$ and $R_4$ independently represent a linear hydrocarbon chain containing from 11 to 23 carbon atoms,
- $A_3$ and $A_4$ represent O or NH, and
- M represents H or a cation.

Preferably, $L_1$ and $L_2$ are identical and/or $X_1$ and $X_2$ are identical and/or $H_1$ and $H_2$ are identical. Surfactants having the formula (I) that are particularly preferred are those in which $L_1$ and $L_2$ are identical, $X_1$ and $X_2$ are identical, and $H_1$ and $H_2$ are identical. These surfactants are indeed symmetrical compounds and are thus generally easier to synthesise, and are therefore less expensive.

In one embodiment, in Formula (I) described here above, the $L_1$-$X_1$—$H_1$— and/or $L_2$-$X_2$—$H_2$— radicals consist of one of the groups having the following formulas (the $Y_1$ or $Y_2$ group being linked to the right of the formulas described here below):

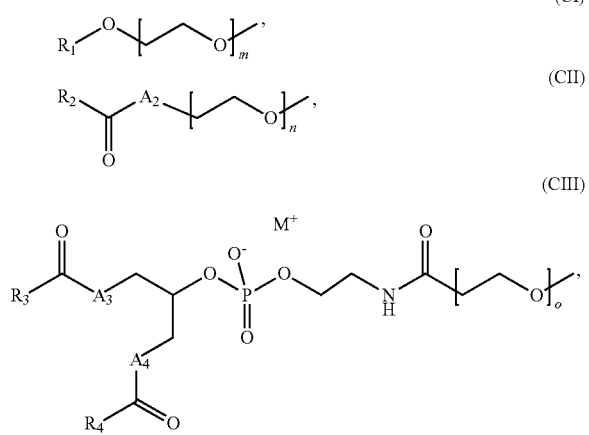

in which:
- $R_1$, $R_2$, $R_3$ and $R_4$ independently represent a linear hydrocarbon chain containing from 11 to 23 carbon atoms,
- $A_1$, $A_2$, $A_3$ and $A_4$ represent O or NH,
- m, n, o and p independently represent integers from 3 to 500, preferably from 20 to 200, and
- represents an integer from 20 to 120,
- M represents H or a cation.

The $L_1$-$X_1$—$H_1$— and/or $L_2$-$X_2$—$H_2$— radicals having the formula (CII) are preferred. Indeed, they are easy to prepare (in particular by means of formation of an ester or an amide between a fatty acid and a derivative of poly(ethylene glycol). In addition, a material including a surfactant containing a $L_1$-$X_1$—$H_1$— and/or $L_2$-$X_2$—$H_2$— radical having the formula (CII) may generally be prepared with a greater amount of this surfactant than a material including a surfactant containing a $L_1$-$X_1$—$H_1$— and/or $L_2$-$X_2$—$H_2$— radical having the formula (CIII). However, the higher the proportion of surfactant having the formula (I) contained in the material, the greater will the cohesion be between the droplets, and the greater will be the ability of the material to maintain its form and be resistant to dilution. Thus, these two properties can be further exacerbated for a material including a surfactant containing a $L_1$-$X_1$—$H_1$— and/or $L_2$-$X_2$—$H_2$— radical having the formula (CII).

The $L_1$-$X_1$—$H_1$— and/or $L_2$-$X_2$—$H_2$— radicals having the formula (CII) with $A_2$ representing NH are particularly preferred, because the surfactants containing such radicals allow preventing the escape of lipophilic agents of interest that may possibly be present outside the droplets of the material more effectively than the surfactants containing the $L_1$-$X_1$—$H_1$— and/or $L_2$-$X_2$—$H_2$— radicals having the formula (CII) with $A_2$ representing O.

In one embodiment, in Formula (I), v and w represent 1, $L_1$ and $L_2$ are independently R—(C=O)—, wherein R represents a linear hydrocarbon chain containing from 11 to 23 carbon atoms, $H_1$ and $H_2$ are independently poly(ethylene oxide) comprising from 3 to 500 ethylene oxide units, $X_1$ and $X_2$ represent —O— or —NH—, G consists of a G' group representing —S—S— (a group having the formula (XV) above) and $Y_1$ and $Y_2$ represent —$CH_2$—$CH_2$—NH—CO—$CH_2$—$CH_2$— (Alk-Z-Alk group as above with Alk representing —$CH_2$—$CH_2$— and Z represents —NH—(CO)—) and the surfactant of the material then has the following formula (I'):

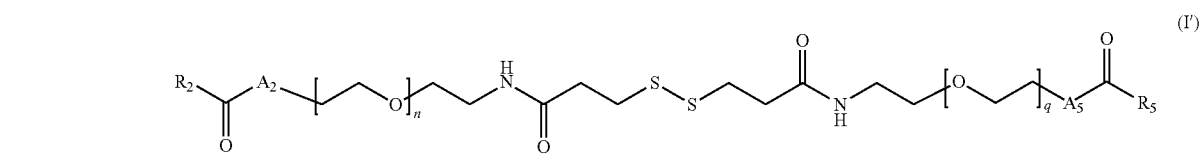

in which:
- $R_2$ and $R_5$ independently represent a linear hydrocarbon chain containing from 11 to 23 carbon atoms, preferably 17,
- $A_2$ and $A_5$ represent O or NH, preferably NH, and
- n and q independently represent integers from 3 to 500, preferably from 20 to 200.

In one embodiment, the $H_1$ and $H_2$ groups are independently selected from a poly(ethylene oxide) comprising more than 3 units of poly(ethylene oxide), or even more than 20 units, in particular more than 50 units (in the above described formulas, m, n, o, p and/or q are preferably greater than 3, or even 20, in particular more than 50).

In one embodiment, the G group of the surfactant having the formula (I) of the material includes a function that is cleavable, in particular chemically (when the surfactant having the formula (I) is placed in contact with a chemical compound capable of cleaving the function of the G group), electrochemically, at certain pHs (acid or alkaline pH), by enzymes, by light (visible light, infrared or ultraviolet light)

-continued

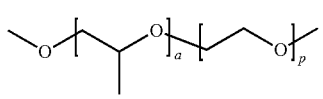

and/or beyond certain temperatures. Generally, the G group then comprises a G' group including a cleavable function.

For example:
- the β-ketoaminoester function of the G' group having the formula (XX) is cleavable at acidic pH (typically of around 5),
- the disulfide function of the G' group having the formula (XV) is cleavable by ultraviolet radiation, electrochemically, chemically (for example, by being placed in contact with a reducing agent such as tris(2-carboxyethyl)phosphine (TCEP) or dithiothreitol (DTT)), or by enzymes such as thioreductases,
- the amide function of the G' group having the formula (XI) is cleavable by enzymes such as proteases,
- the phosphate function of the G' group having the formula (XXII) is cleavable by enzymes such as phosphatases,
- the imine function of the G' group having the formula (XXI) and (XIII) are cleavable at acid pH or above certain temperatures,
- the cyclohexene ring of the G' group having the formula (XVII) is cleavable beyond certain temperatures (by retro Diels-Alder cleavage),
- the carbonate function of the G' group having the formula (XIX) and the carbamate function of the G group having the formula (XII) are cleavable at acidic pH or chemically (for example by reaction with a nucleophilic agent),
- the ortho nitrobenzyl function of the G' group having the formula (XXIV) is cleavable by the action of light at 365 nm.

The person skilled in the art, in the light of his general knowledge, knows the functions that are cleavable and the conditions under which that is so. He is in particular in a position to select the function of the G' group of the surfactant having the formula (I) in order for it to be cleavable under the conditions encountered in the desired application of the material according to the invention.

In one embodiment, cleavage of the cleavable function of the G group of the surfactant having the formula (I) of the material is reversible, that is to say that the function may possibly be re-formed so as to recreate covalent bonds between the droplets. The person skilled in the art knows the reversible chemical reactions and the conditions for cleavage and re-formation of bonds. Purely by way of illustration, for example, the disulfide function of the G' group having the formula (XV) may be cleaved by being brought in contact with a reducing agent and may be reformed by being brought in contact with an oxidising agent.

Amphiphilic Lipid

The material comprises an amphiphilic lipid as a surfactant which enables the formation of the droplets of the dispersed phase. The amphiphilic nature of the surfactant ensures the stabilisation of the droplets of oil within the continuous aqueous phase.

The amphiphilic lipids comprise a hydrophilic part and a lipophilic part. They are generally selected from among the compounds wherein the lipophilic part includes a linear or branched, saturated or unsaturated chain, having from 8 to 30 carbon atoms. They may be selected from among phospholipids, cholesterols, lysolipids, sphingomyelins, tocopherols (unesterified), glucolipids, stearylamines, cardiolipins of natural or synthetic origin; molecules composed of a fatty acid coupled to a hydrophilic group by an ether or ester function such as sorbitan esters like for example sorbitan monooleate and sorbitan monolaurate sold under the trade names Spana by the company Sigma; polymerised lipids; conjugated lipids with short polyethylene oxide (PEG) chains such as non-ionic surfactants sold under the trade names Tween® by the company ICI Americas, Inc. and Triton® by the company Union Carbide Corp; sugar esters such as mono- and di-laurate, mono- and di-palmitate, sucrose mono stearate and sucrose distearate; the said surfactants may be used alone or in mixtures.

Phospholipids are the particularly preferred amphiphilic lipids, in particular the phospholipids selected from among phosphatidyl choline, phosphatidyl ethanolamine, phosphatidyl serine, phosphatidyl glycerol, phosphatidyl inositol, either non-hydrogenated or hydrogenated phosphatidyl phosphatidic acid, notably sold by the company Lipoid.

Lecithin is the preferred amphiphilic lipid.

Typically the oily phase will comprise from 0.01% to 99% by weight, preferably from 5% to 75% by weight, in particular from 10% to 60%, and most particularly from 15% to 45% by weight of amphiphilic lipid.

The amount of amphiphilic lipid advantageously contributes to controlling the size of droplets of the dispersed phase of the material.

Solubilising Lipid

The material according to the invention may include a solubilising lipid, which in particular provides the ability to:
- increase the physical and chemical stability of the material, and
- where the material comprises a lipophilic agent of interest encapsulated within the droplets:
  - solubilise the lipophilic agent of interest, and
  - improve control of the release of the lipophilic agent of interest.

Preferably the solubilising lipid is solid at ambient temperature (20° C.).

The solubilising lipid may especially be composed of derivatives of glycerol, and in particular of glycerides obtained by esterification of glycerol with fatty acids, notably in the case where the amphiphilic lipid is a phospholipid.

The preferred solubilising lipids, in particular for phospholipids, are glycerides of fatty acids, especially saturated fatty acids, in particular saturated fatty acids containing from 8 to 18 carbon atoms, more preferably from 12 to 18 carbon atoms. Advantageously, the solubilising lipid consists of a complex mixture of various different glycerides. The term "complex mixture" is used to refer to a mixture of mono, di and triglycerides containing fatty chains of different lengths, the said lengths extending preferentially from C8 to C18, for example, in combination, the C8-, C10-, C12-, C14-, C16-, and C18 chains, or from C10 to C18, including, for example in combination, C10-, C12-, C14-, C16-, and C18 chains.

In one embodiment, the said fatty chains may contain one or more unsaturations.

Preferably, the solubilising lipid consists of a mixture of glycerides of saturated fatty acids comprising at least 10% by weight of C12 fatty acids, at least 5% by weight of C14 fatty acids, at least 5% by weight of C16 fatty acids and at least 5% by weight of C18 fatty acids.

Preferably the solubilising lipid consists of a mixture of glycerides of saturated fatty acids containing 0% to 20% by weight of C8 fatty acids, 0% to 20% by weight of C10 fatty acids, 10% to 70% by weight of C12 fatty acids, 5% to 30% by weight of C14 fatty acids, 5% to 30% % by weight of C16 fatty acids, and 5% to 30% by weight of C18 fatty acids.

The mixtures of solid semi-synthetic glycerides that are solid at ambient temperature, sold under the trade name Suppocire®NB by the company Gattefossé and approved for use in humans are particularly preferred solubilising lipids. The N type Suppocire® are obtained by direct esterification of fatty acids and glycerol. These are semi synthetic glycerides of C8 to C18 saturated fatty acids, of which the qualitative and quantitative composition is indicated in the table here below

TABLE

Fatty acid composition of Suppocire ® NB from Gattefossé

| Length of chains | [% by weight] |
|---|---|
| C8 | 0.1 to 0.9 |
| C10 | 0.1 to 0.9 |
| C12 | 25 to 50 |
| C14 | 10 to 24.9 |
| C16 | 10 to 24.9 |
| C18 | 10 to 24.9 |

The above noted solubilising lipids make it possible to obtain an advantageously stable material. Without intending to be bound to any particular theory, it is assumed that the aforementioned solubilising lipids make it possible to obtain within the material droplets having an amorphous core. The core thus obtained has a high internal viscosity without however exhibiting any crystallinity. However, crystallisation is detrimental to the stability of the material as it generally leads to an aggregation of the droplets and/or to expulsion of the lipophilic agent of interest, if present, to the exterior of the droplets. These physical properties greatly contribute to the physical stability of the material.

The amount of solubilising lipid may vary widely depending on the nature and the quantity of amphiphilic lipid present in the dispersed phase. Generally, the dispersed phase will comprise from 1% to 99% by weight, preferably from 5% to 80% by weight and most particularly from 30% to 75% by weight of solubilising lipid.

Oil

The dispersed phase of the material according to the invention may also include one or more oils.

The used oils preferably have a hydrophilic-lipophilic balance (HLB) of less than 10 and even more preferably comprised between 3 and 9. Advantageously, the oils are used without prior chemical or physical modification to the formation of the material.

Depending on the envisaged applications, the oils may be selected from the biocompatible oils, and in particular from oils of natural origin (plant or animal) or synthetic origin. Among these oils, mention may in particular be made of oils of natural plant origin among which are notably included oils from soybean, linseed, palm, peanut, olive, sesame, grape seed and sunflower; the synthetic oils among which are included in particular triglycerides, diglycerides and monoglycerides. These oils may be from first pressings, refined or inter-esterified.

The preferred oil is soybean oil.

Generally, if present, the oil will be contained in the dispersed phase in a proportion ranging from 1% to 80% by weight, preferably between 5% and 50% by weight and most particularly from 10% to 30% by weight relative to the total weight of the oily phase.

Aqueous Phase

The continuous aqueous phase of the material according to the invention is preferably constituted of water and/or a buffer such as a phosphate buffer, like for example PBS ("Phosphate Buffer Saline") or a salt solution, in particular of sodium chloride. Generally, the pH of the aqueous phase is in the range of the physiological pH.

According to one embodiment, the continuous phase further includes a thickening agent such as glycerol, a saccharide, oligosaccharide or polysaccharide, a gum or even a protein, preferably glycerol. Indeed, the use of a continuous phase of higher viscosity facilitates the emulsification and thereby provides the ability to reduce the time of sonication.

The aqueous phase advantageously includes from 0% to 50% by weight, preferably from 1% to 30% by weight and most preferably from 5% to 20% by weight of a thickening agent.

Quite obviously, the aqueous phase may further contain other additives such as dyes, stabilisers and preservatives in appropriate amounts.

Co-Surfactant

The material according to the invention may also comprise a co-surfactant. This co-surfactant is located partially in the continuous aqueous phase and partially in the droplets of the dispersed phase.

Preferably, the co-surfactant contains at least one chain composed of units of ethylene oxide or of ethylene oxide and propylene oxide. It may be selected in particular from among the conjugate compounds polyethylene glycol/phosphatidyl ethanolamine (PEG-PE), ethers of fatty acid and polyethylene glycol, esters of fatty acid and polyethylene glycol, and block copolymers of ethylene oxide and propylene oxide.

The polyalkoxylated chain of the co-surfactant comprises generally from 10 to 200, typically from 10 to 150, especially from 20 to 100, preferably from 30 to 80, units of ethylene oxide/propylene oxide. With less than 10 units, the material is not homogeneous because the dispersed phase includes polydisperse droplets, and does not allow for controlling the time of release of the lipophilic agent of interest if it is present. Beyond 200 units, on the one hand the emulsion is not homogeneous because the dispersed phase includes polydisperse droplets, and does not allow for the possibility of controlling the time of release of the lipophilic agent of interest.

By way of examples of co-surfactants, mention may be made in particular of the conjugate compounds based on polyethylene glycol/phosphatidyl ethanolamine (PEG-PE), ethers of fatty acid and polyethylene glycol such as the products sold under the trade name Brij® (for example Brij® 35, 58, 78 or 98) by the company ICI Americas Inc., esters of fatty acid and polyethylene glycol, such as the products sold under the trade names Myrj® by the company ICI Americas Inc. (for example Myrj s20, s40 or s100, previously referenced as 49, 52 or 59) and block copolymers of ethylene oxide and propylene oxide such as the products sold under the trade names Pluronic® by the company BASF AG (for example Pluronic® F68, F127, L64, L61, 10R4, 17R2, 17R4, 25R2 or 25R4) or the products sold under the trade name Synperonic® by the company Unichema Chemie BV (for example Synperonic® PE/F68, PE/L61 or PE/L64).

Preferably, the ratio of the mass of surfactant having the formula (I) over the mass of the ensemble (surfactant having the formula (I)/co-surfactant) is greater than or equal to 15%. It has indeed been observed that such materials are easier to prepare.

The aqueous phase generally includes from 0.01% to 50% by weight, preferably from 1% to 30% by weight and most particularly from 5% to 20% by weight of co-surfactant.

Generally, the mass fraction of the ensemble [optional co-surfactant/amphiphile lipid/surfactant having the formula (I)] relative to the total weight of the core of the droplets [optional oil/optional solubilising lipid/optional co surfactant/amphiphilic lipid/optional lipophilic agent of interest] is less than or equal to 2, preferably less than or equal to 1. This makes it possible to obtain a physically stable system that is not subject to the effects of destabilisation due to Ostwald ripening or coalescence (separation of the aqueous and oily phases).

Generally, the mass fraction of amphiphilic lipid relative to the weight of the co-surfactant is from 0.005% to 100%, notably from 0.01% to 50%, preferably from 0.1% to 30%. Indeed, below 0.005% and above 100%, the droplets of the dispersed phase are often not sufficiently stable and they coalesce within a few hours and it is often difficult to obtain droplets with a diameter of less than 200 nm.

Generally, the material does not include any additional surfactants: the only surfactants of the material are the amphiphilic lipid, the co-surfactant and the surfactant having the formula (I).

In one embodiment, the polyalkoxylated co-surfactant includes a grafted compound of interest. Typically, the compound of interest has been grafted through a chemical bond, generally a covalent bond, to the co-surfactant as defined here above. The grafting may be carried out prior to or after the formation of the emulsions used to prepare the material (emulsions 1 and 2 here below). The latter case may be recommended when the chemical reactions used are compatible with the stability of the emulsions, in particular in terms of pH. Preferably, the pH during the grafting reaction is comprised between 5 and 11.

Generally, this grafting has been carried out at one end of the polyalkoxylated chain or chains of the co-surfactant, and the compound of interest is thus located at the surface of the droplets of the dispersed phase of the material.

The compounds of interest may for example be:
  biological targeting ligands such as antibodies, peptides, saccharides, aptamers, oligonucleotides or compounds such as folic acid; during the release from the droplets of the material, this biological ligand will be recognised in a specific manner by certain cells (for example tumoral cells as for example described in the article of S. Achilefu, Technology in Cancer Research & Treatment, 2004, 3, 393-408) or by certain organs which it is desired to target, which provides the ability to control the localisation of the release of the optional lipophilic agent of interest;
  a stealth agent: an added entity in order to impart stealth to the material with regard to the immune system, to increase the circulation time thereof in the organism, and to slow down the elimination thereof.

Agent of Interest

In one embodiment, the material may include one or more agent(s) of interest.

The agent of interest may be of highly varied nature depending on the desired application of the material. Thus, the agent of interest may be:
  a chemical sensing agent ("scavenger" in English), that is to say a compound that is capable of reacting with a chemical compound that it is desired to eliminate from a medium. The chemical sensor incorporated into the material according to the invention is chosen based on the compound that it is desired to eliminate. For example, a chemical sensor can react with impurities and perhaps can thus be used in order to purify or decontaminate a medium. In another example, during a chemical reaction, a chemical sensor may be used to eliminate the products of a secondary reaction or excess reagent.
  a chemical detection agent, that is to say a chemical compound that is capable of emitting a signal when it is placed in contact with an analyte that it is desired to be detected and/or quantified. The chemical detector may be a fluorogenic detector (bringing into contact the fluorogenic detector with the analyte produces a detectable fluorescent emission) or a chromogenic detector (bringing into contact the chromogenic detector with the analyte produces a detectable change in colour). The analyte may be of any kind, for example a bacterium (such as in the patent application FR 2 954 911), a metal, a pollutant, etc. The chemical detector incorporated within the material according to the invention is selected based on the analyte that it is desired to detect. For purely illustrative purposes, in order to detect heavy metals, a quinoline derivative may be incorporated in the droplets of the material according to the invention as a fluorogenic detector (Da-Yu Wu et al., Dalton Trans., 2006, 3528-3533).
  a catalyst, such as a metallic or an organometallic catalyst.
  an optical agent such as a dye, a chromophore, a fluorophore, for example 1,1'-Dioctadecyl-3,3,3,3-tetramethylindodicarbocyanine perchlorate (DiD), 1,I-Dioctadecyl-3,3,3',3-tetramethylindotricarbocyanine iodide (DiR), indocyanine green (ICG), or even components having optoelectronic properties, such as saturants or optical absorbents).
  a phytosanitary or plant protection agent, such as a mineral substance (for example: copper sulphate) or organic substance (for example: carbamate such as carbofuran, furadan, etc), natural substance (for example: Bacillus thuringiensis Bt) or derived from chemical synthesis (for example: Glyphosate).
  a taste/odour masking agent, such as a flavour substance and/or fragrance or aroma substance, such as menthol or cinnamaldehyde, for pharmaceutical (galenic) use or agrifood application.
  a cosmetic agent.
  a therapeutic agent, such as an pharmaceutical active ingredient or a physical agent, such as a radioactive isotope or a photosensitiser.
    Therapeutic agents that may be included in the material according to the invention include in particular active ingredients acting via the chemical, physical or biological route. Thus, it may involve pharmaceutical active ingredients or biological agents such as DNA, proteins, peptides or antibodies or even agents that are useful for physical therapies such as compounds useful for thermotherapy, compounds useful for phototherapy that release singlet oxygen when they are excited by a light, and radioactive agents.

Among the pharmaceutical active ingredients that are of interest as therapeutic agents, mention may be made in particular of the agents used in the treatment of AIDS, agents used in the treatment of heart disease, analgesics, anesthetics, anorectics, anthelmintics, anti-allergic agents, antianginals, antiarrhythmics, anticholinergics, anticoagulants, antidepressants, antidiabetics, anti-diuretics, antiemetics, anticonvulsants, antifungals, antihistamines, antihypertensives, anti-inflammatories, anti-migraine agents, antimuscarinics, antimycobacterials, anticancer agents including antiparkinson agents, anti-thyroid agents, antivirals, astringents, blocking agents, blood products, blood substitutes, cardiac inotropic agents, cardiovascular agents, central nervous system agents, chelating agents chemotherapy agents, hematopoietic growth factors, corticosteroids, cough suppressants, dermatological agents, diuretics, dopaminergic agents, inhibitors of elastase, endocrine agents, ergot alkaloids, expectorants, gastrointestinal agents, genitourinary agents, the growth hormone releasing factor, growth hormones, hematological agents, hematopoietic agents, hemostatics, hormones, immunological agents, immunosuppressants, interleukins, interleukin analogues, lipid regulating agents, gonadotropin releasing hormone, muscle relaxants, narcotic antagonists, nutrients, nutritional agents, oncology therapies, organic nitrates, parasympathomimetic agents, prostaglandins, antibiotics, renal agents, respiratory agents, sedatives, sex hormones, stimulants, sympathomimetic agents, systemic anti-infectives, tacrolimus, thrombolytic agents, thyroid agents, treatments for attention disorders, vaccines, vasodilators, xanthines, cholesterol lowering agents, healing agents.

Among the active ingredients acting via the biological route, mention may be made of oligonucleotides, DNA, RNA, siRNA, microRNA's, peptides and proteins. Quite obviously, the therapeutic agents can be formulated directly in their active form or in the form of a prodrug.

Among the physical agents, mention may be made in particular of radioisotopes, and photosensitisers.

Among the photosensitisers, mention may be made in particular of those belonging to the class of tetrapyrroles such as porphyrins, bacteriochlorins, phthalocyanines, chlorins, purpurins, porphycenes, pheophorbides, or even those belonging to the class of texaphyrins or hypericins. Mention may also be made of derivatives of 5-aminolevulinic acid and the ester derivatives thereof, these components being known as metabolic precursors of Protoporphyrin IX. Among the first generation photosensitisers, mention may be made of hemato porphyrin and a mixture of hemato porphyrin derivatives (HpD) (sold under the trade name Photofrin® by Axcan Pharma). Among the second generation photo-sensitisers, mention may be made of meta-tetra-hydroxyphenyl chlorin (mTHPC; trade name Foscan Biolitec AG) and the Benzoporphyrin derivative monoacid ring A (BPD-MA sold under the trade mark Visudyne® by QLT and Novartis Opthalmics). Formulations of second generation photosensitisers which combine with these photosensitisers a molecule (lipid, peptide, sugar, etc) qualified as a transporter that makes possible the selective routing and delivery thereof in the tumour tissue are called third generation photosensitisers.

Furthermore, the oily phase can, in addition to the therapeutic agent, also include an imaging agent, in particular for MRI (Magnetic Resonance Imaging), PET (Positron Emission Tomography), SPECT (Single Photon Emission Computed Tomography), ultrasound echography, radiography, x ray tomography and optical imaging (fluorescence, bioluminescence, diffusion, etc). These agents can be used to track and trace the position of the droplets (and thus of the therapeutic agent) after administration of the material to the patient.

The quantities of the agent of interest are dependent upon the intended application as well as upon the nature of the agents.

However, when the agents of interests are therapeutic agents, it would generally be sought to formulate the material with a maximum concentration of the therapeutic agent, in order to limit the volume and/or duration of application, in particular the volume and/or duration of administration to the patient.

However, it has been found that the presence of the solubilising lipid in the oily phase provides the ability to incorporate a fairly significant amount of the lipophilic agent of interest therein. The solubilising lipid indeed facilitates the incorporation of the lipophilic agents of interest into the core of the droplets. Amphiphilic agents of interest are mainly incorporated into the membrane of the droplets.

The material according to the invention will most often contain a quantity from 0.001% to 30% by weight, preferably from 0.01% to 20% by weight, and even more preferably from 0.1% to 10% by weight of the agent of interest.

The agent of interest may be hydrophilic (it would then be located in the aqueous continuous phase of the material) or lipophilic (it would then be encapsulated within the droplets that form the dispersed phase of the material or be located at the interface of the aqueous and oily phases on the surface of the droplets, depending on its amphiphilic or lipophilic affinity).

In one embodiment, the material includes at least one hydrophilic agent of interest and at least one lipophilic agent of interest. For example, the material comprises at least one hydrophilic therapeutic agent and at least one lipophilic therapeutic agent.

Other Properties of the Material

On account of its formulation, the material according to the invention is stable and offers an excellent degree of storage stability (greater than 5 months or than 8 months).

In addition, the material may be formulated in a manner such as to ensure that the surface of the dispersed phase has a low zeta potential, ideally comprised between −25 mV and +25 mV, or even between −20 mV and +20 mV, and in particular between −10 mV and +10 mV, or even zero.

Indeed, the polyalkoxylated chains of the co-surfactant and the surfactant having the formula (I), that are hydrated and uncharged, covering the surface of the droplets, serve to screen the charges carried by the amphiphilic lipids at the solid surface of the droplets. The condition found to be brought about is therefore a case of steric stabilisation of the droplets, and not an electrostatic stabilisation thereof. The zeta potential is a key parameter that has significant effect on the interactions with biological media. The droplets that possess a highly positive surface charge, that is to say greater than 25 mV are generally more cytotoxic than droplets with negative or neutral zeta potential.

Furthermore, a low zeta potential has the advantage of limiting the nonspecific recognition of the droplets by macrophages when the material is dispersed, in particular in viva In contrast to emulsions whose stability is based on electrostatic effects, and which have a high zeta potential and can be spontaneously stable, the emulsions described in the context of this invention require a supply of energy in order to be formed, for example by means of sonication. The emulsion thus obtained is then metastable and comprises droplets whose charge is low or zero.

Preferably, the pH of the material is comprised between 5.5 and 8.5 and preferably between 6 and 7.5. A pH within these ranges is compatible with the use of an appropriate aqueous buffer adapted to the pH of a physiological medium.

[Method of Preparation]

According to a second object, the invention relates to a method for preparing the material defined here above, comprising bringing into contact:
  an emulsion 1 comprising a continuous aqueous phase and a dispersed phase, dispersed in the form of droplets containing an amphiphilic lipid and a surfactant having the following formula (LI):

$$L_1-X_1-H_1-Y_1-G_1 \quad (LI),$$

with an emulsion 2 comprising a continuous aqueous phase and a dispersed phase, dispersed in the form of droplets containing an amphiphilic lipid and a surfactant having the following formula (LII):

$$G_2-Y_2-H_2-X_2-L_2 \quad (LII)$$

wherein $L_1$, $X_1$, $H_1$, $Y_1$, $L_2$, $X_2$, $H_2$ and $Y_2$ are as defined here above, and $G_1$ and $G_2$ are groups that are capable of reacting in order to form the G group as defined here above, under conditions that allow for the reaction of the surfactants having the formulas (LI) and (LII) in order to form the surfactant having the formula (I) as defined here above, whereby covalent bonds between the droplets of the dispersed phase are formed.

According to a preferred embodiment of the invention, the reaction of G1 and G2 in order to form the G group is carried out by irradiation of the mixture formed by the emulsion 1 and the emulsion 2 by means of a light radiation.

When the G group comprises a single G' group, the $G_1$ and $G_2$ groups are typically groups that are capable of reacting with each other so as to form the G group.

When the G group comprises several G' groups, generally the emulsions 1 and 2 are placed into contact with a compound that is capable of reacting with the surfactants having the formulas (LI) and (LII) in order to form the G group. This compound typically comprises at least v functions $G'_1$ that are capable of reacting with the $G_1$ group and w functions $G'_2$ that are capable of reacting with the $G_2$ group.

Thus, in the embodiment in which the G group has the formula -G'-$Y_3$-G'- as defined here above, the method for preparing the material typically comprises bringing into contact:
  an emulsion 1 as defined here above,
  and an emulsion 2 as defined here above,
  with a compound having the formula $G'_1$-$Y_3$-$G'_2$ in which $Y_3$ is as defined here above, $G'_1$ is a group that is capable of reacting with $G_1$ in order to form the first G' group as defined here above and $G'_2$ is a group that is capable of reacting with $G_2$ in order to form the second G' group as defined here above (being of the same or different nature as the first G' group),
under conditions that allow for the reaction of the surfactants having the formulas (LI) and (LII) and the compound having the formula $G'_1$-$Y_3$-$G'_2$ in order to form the surfactant having the formula (I) in which the G group has the formula -G'-$Y_3$-G'- as defined here above, whereby covalent bonds between the droplets of the dispersed phase are formed.

In similar fashion, in the embodiment defined here above wherein the G group is a dendrimer comprising (v+w) G' groups, the method for preparing the material typically comprises bringing into contact:
  an emulsion 1 as defined here above,
  and an emulsion 2 as defined here above,
  with a dendrimer having the formula $(G'_1)_v$-$Y_4$-$(G'_2)_w$ in which v and w are as defined here above, $G'_1$ is independently a group that is capable of reacting with $G_1$ in order to form a G' group as defined here above and $G'_2$ is independently a group that is capable of reacting with $G_2$ in order to form a G' group as defined here above (each G' group being of the same or different nature as the other G' groups) and $Y_4$ is the skeleton of a dendrimer,
under conditions that allow for the reaction of the surfactants having the formulas (LI) and (LII) and the dendrimer having the formula $(G'_1)_v$-$Y_4$-$(G'_2)_w$ in order to form the surfactant having the formula (I) in which the G group is a dendrimer comprising (v+w) G' groups, whereby covalent bonds between the droplets of the dispersed phase are formed.

For example, in order to form a G group having the formula (XXX), (XXXI), (XXXII) and (XXXIII), the compound having the formula $(G'_1)_v$-$Y_4$-$(G'_2)_w$ may respectively have one of the following formulas (XXX'), (XXXI'), (XXXII') and (XXXIII'):

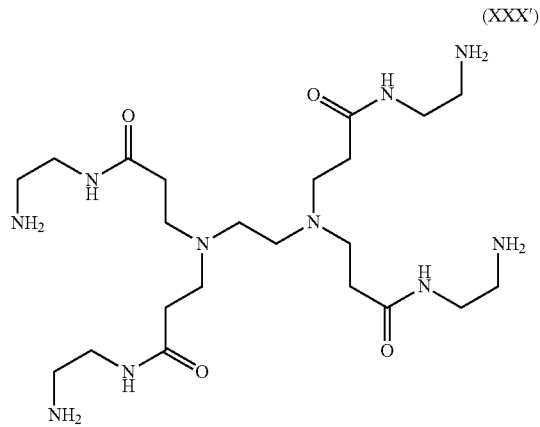 [SMILES: NCCNC(=O)CCN(CCC(=O)NCCN)CCN(CCC(=O)NCCN)CCC(=O)NCCN]

(XXX')

(wherein G'$_1$ and G'$_2$-represent NH$_2$ and v and w represent 2),
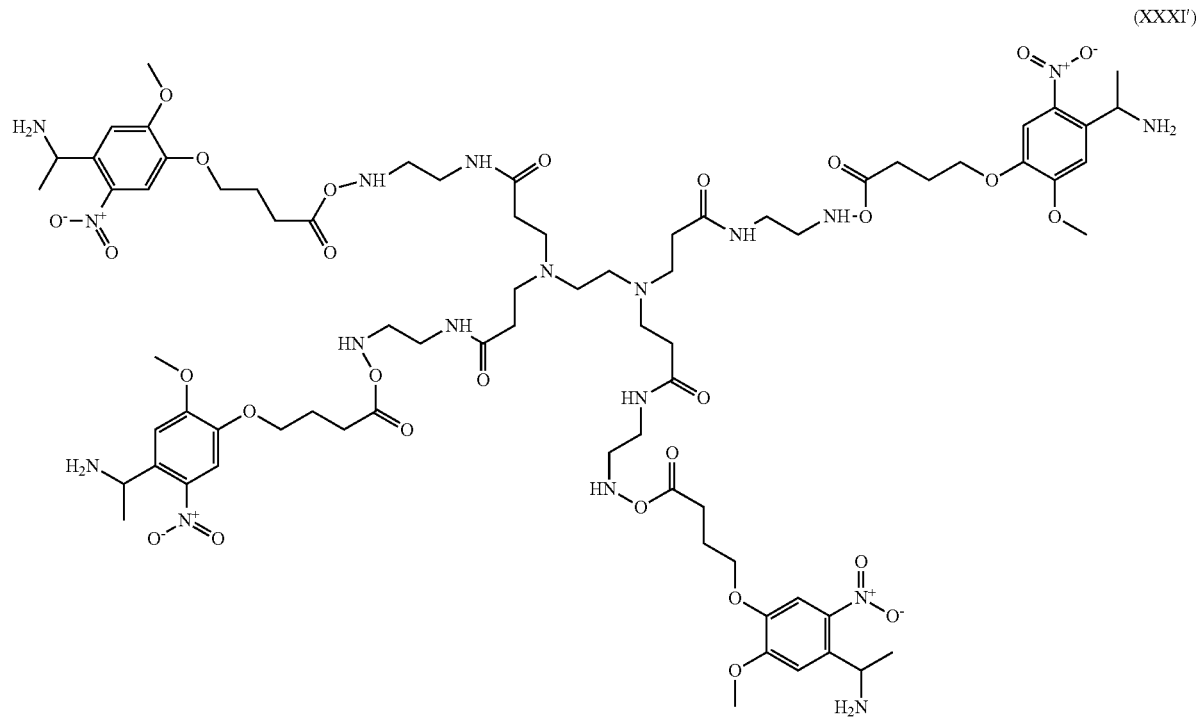 [SMILES: COc1cc(C(C)N)c([N+](=O)[O-])cc1OCCCC(=O)ONCCNC(=O)CCN(CCC(=O)NCCNOC(=O)CCCOc1cc([N+](=O)[O-])c(C(C)N)cc1OC)CCN(CCC(=O)NCCNOC(=O)CCCOc1cc([N+](=O)[O-])c(C(C)N)cc1OC)CCC(=O)NCCNOC(=O)CCCOc1cc([N+](=O)[O-])c(C(C)N)cc1OC]
(XXXI')
(wherein G'$_1$ and G'$_2$-represent NH$_2$ and v and w represent 2),
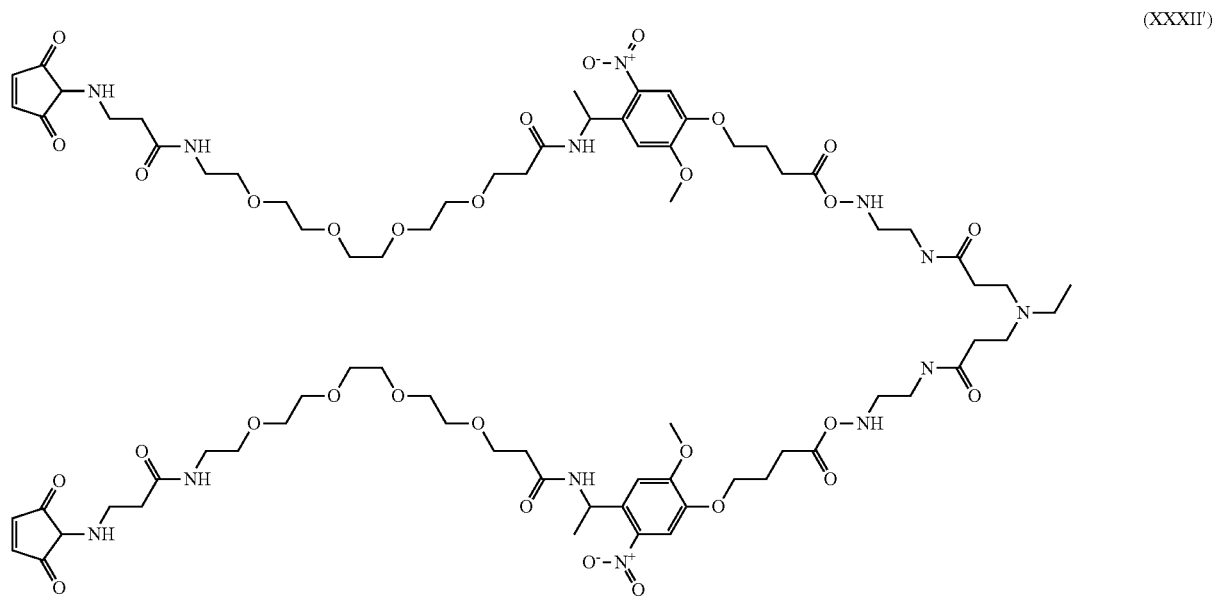
(XXXII')

-continued
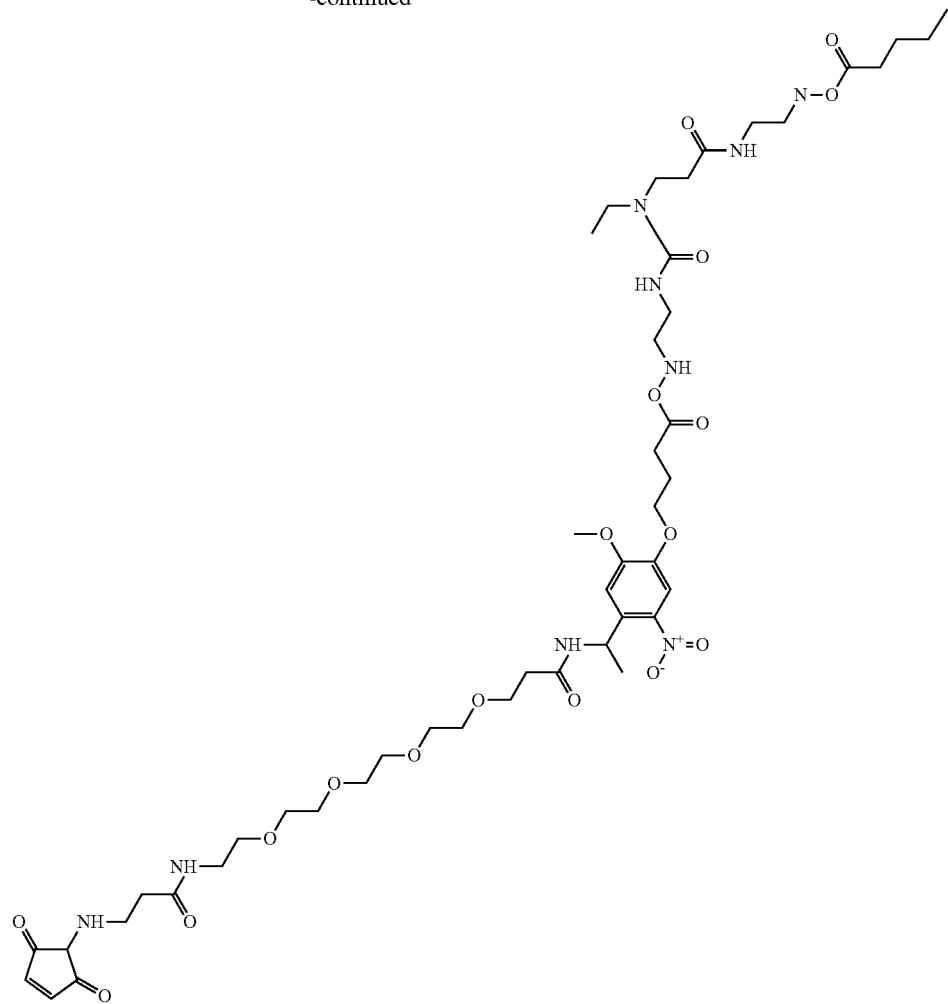
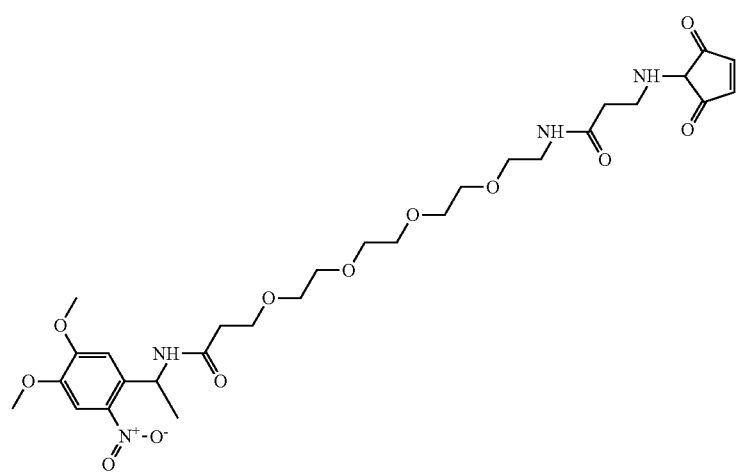 [SMILES: COc1cc(C(C)NC(=O)CCOCCOCCOCCOCCNC(=O)CCNC2C(=O)C=CC2=O)c([N+](=O)[O-])cc1OC]

(wherein G'₁ and G'₂-represent
and v and w represent 2),
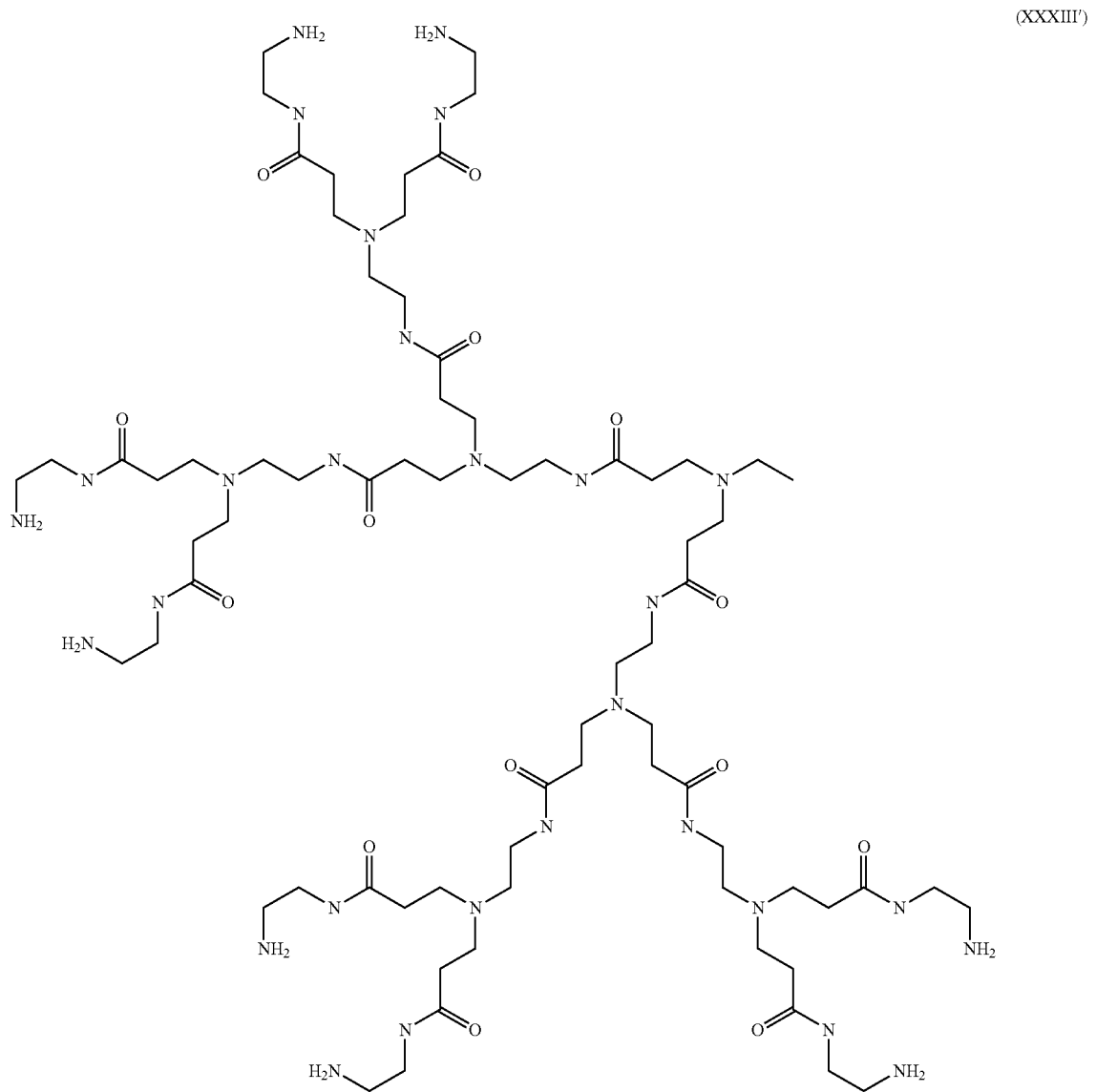 [SMILES: CCN(CCC(=O)NCCN(CCC(=O)NCCN(CCC(=O)NCCN)CCC(=O)NCCN)CCC(=O)NCCN(CCC(=O)NCCN)CCC(=O)NCCN)CCC(=O)NCCN(CCC(=O)NCCN(CCC(=O)NCCN)CCC(=O)NCCN)CCC(=O)NCCN(CCC(=O)NCCN)CCC(=O)NCCN]
(XXXIII')

-continued

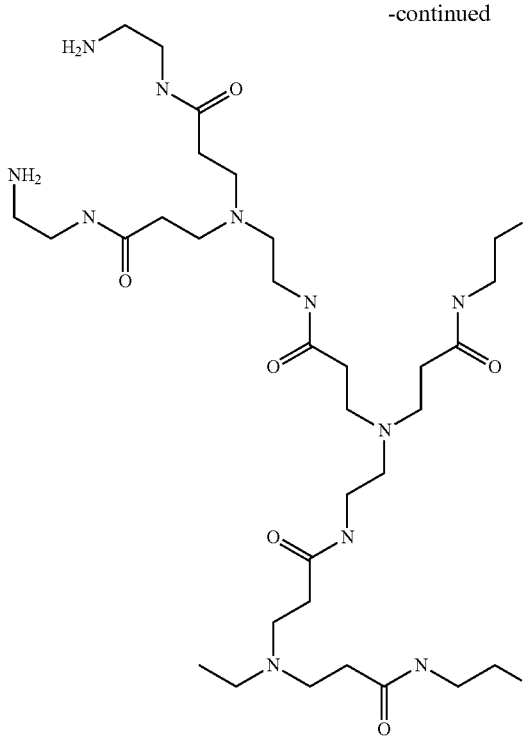
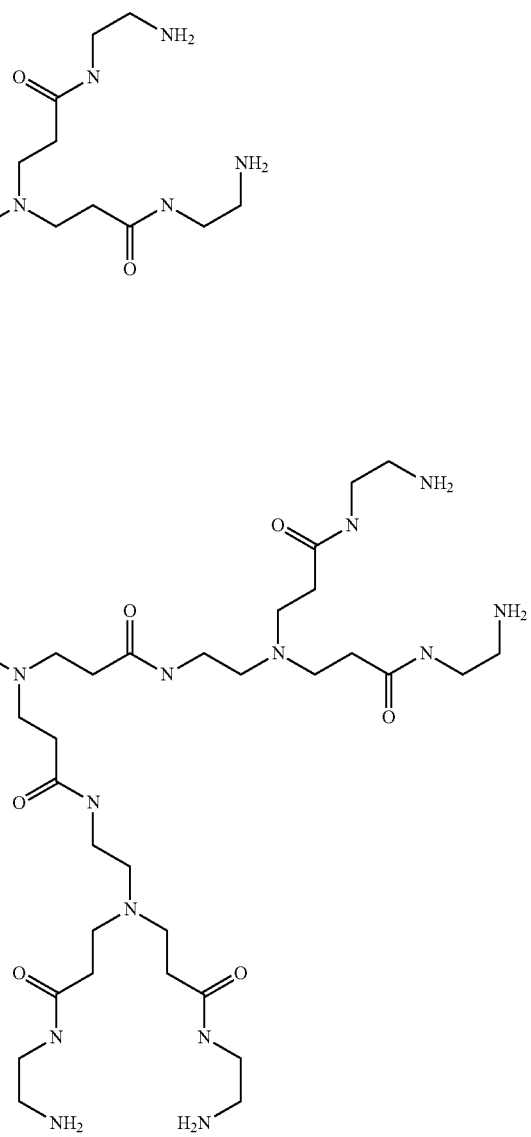

(wherein G'₁ et G'₂-represent NH₂ and v and w represent 8).

Formation of the Surfactant Having the Formula (I) by Reaction Between the Surfactants Having the Formulas (LI) and (LII)

In the light of their general knowledge in chemistry, the person skilled in the art is in a position to select the nature of the G'₁, G'₂, Y₃, Y₄, G₁ and G₂ groups to be used in order to form the G group, as well as the conditions that would allow for the reaction to occur. The usual reactions in organic chemistry may be followed, in particular those described in "Comprehensive Organic Transformations: A Guide to Functional Group Preparations" by Richard C. Larock published by John Wiley & Sons Inc, and the references that are cited therein. Thus, the examples of G₁ and G₂ groups cited here below are intended by way of illustration and are not limiting.

Typically, when the G group consists of a G' group, the G₁ and G₂ groups of the surfactants having the formulas (LI) and (LII) may for example be chosen as follows:

G₁ represents a thiol (—SH) and G₂ represents:
either a maleimide, a surfactant having the formula (I) in which G comprises a G' group representing a group having the formula (XIV) wherein A₁₀₂ represents N then being formed,
or a vinyl sulfone, a surfactant having the formula (I) in which G comprises a G' group representing a group having the formula (XVI) being then formed,
or a group —SS-pyridinyl or —SH, a surfactant having the formula (I) in which G comprises a G' group representing a group having the formula (XV) being then formed, G₁ represents a hydroxyl and G₂ represents —COOH or an activated ester, a surfactant having the formula (I) in which G comprises a G' group representing a group having the formula (XXIII) being then formed, G₁ represents an amine —NH₂ and G₂ represents —COOH or an activated ester, a surfactant having the formula (I) in which G comprises a G' group representing a group having the formula (XI) then being formed, G₁ represents a hydroxyl and G₂ represents an activated carbonate, a surfactant having the formula (I) in which G comprises a G' group representing a group having the formula (XIX) then being formed, $G_1$ represents an amine —$NH_2$ and $G_2$ represents an activated carbonate, a surfactant having the formula (I) in which G comprises a G' group representing a group having the formula (XII) being then formed, $G_1$ represents an amine $NH_2$ and $G_2$ represents an aldehyde CHO, a surfactant having the formula (I) in which G comprises a G' group representing a group having the formula (XXI) being then formed, $G_1$ represents a hydrazide having the formula —(C=O)—NH—$NH_2$ and $G_2$ represents a group —(C=O)—$R10_2$, a surfactant having the formula (I) in which G comprises a G' group representing a group having the formula (XIII) being then formed, $G_1$ represents an alkyne and $G_2$ represents an azide, a surfactant having the formula (I) in which G comprises a G' group representing a group having the formula (XVIII) being then formed, $G_1$ represents a cyclooctyne and $G_2$ represents an azide, a surfactant having the formula (I) in which G comprises a G' group representing a group having the formula (XVIII') then being formed, $G_1$ represents a furan and $G_2$ represents a maleimide, a surfactant having the formula (I) in which G comprises a G' group representing a group having the formula (XVII) being then formed, $G_1$ represents an aldehyde and $G_2$ represents an amine, a surfactant having the formula (I) in which G comprises a G' group representing a group having the formula (XXI) being then formed, $G_1$ represents a phosphate having the formula —O—P(=O)$(OH)_2$ and $G_2$ represents a hydroxyl, a surfactant having the formula (I) in which G comprises a G' group representing a group having the formula (XXII) then being formed, $G_1$ represents a good leaving group LG and $G_2$ represents a group having the following formula

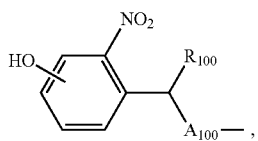

a surfactant having the formula (I) in which G comprises a G' group representing a group having the formula (XXIV) wherein $A_{101}$ represents 0 then being formed, $G_1$ represents a hydroxyl or an amine —$NH_2$ and $G_2$ represents a group having the following formula

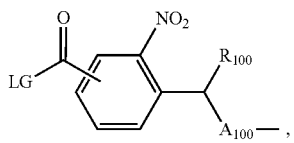

a surfactant having the formula (I) in which G comprises a G' group representing a group having the formula (XXIV) wherein $A_{101}$ represents respectively —O—(CO)— or —NH—(CO) being then formed, $G_1$ represents a good leaving group LG and $G_2$ represents a hydroxyl, a surfactant having the formula (I) in which G comprises a G' group representing a group having the formula (XXV) being then formed, $G_1$ represents a good leaving group LG and $G_2$ represents an amine —$NH_2$, a surfactant having the formula (I) in which G comprises a G' group representing a group having the formula (XXVI) being then formed, $G_1$ represents an oxyamine —O—$NH_2$ and $G_2$ represents an aldehyde, a surfactant having the formula (I) in which G comprises a G' group representing a group having the formula (XXVII) being then formed.

When the G group comprises a plurality of G' groups, the selection of groups reacting together: $G'_1$ and $G_1$ on the one hand and $G'_2$ and $G_2$ on the other hand, may be carried out in the same manner, by replacing the $G_1$ or $G_2$ groups in the examples mentioned above with $G'_1$ or $G'_2$.

Emulsions 1 and/or 2 Comprising a Surfactant Having the Formula (LI) and (LII) where $L_1$-$X_1$—$H_1$— and/or $L_2$-$X_2$—$H_2$— has (have) the Formula (CII) Mentioned Above According to another object, the invention relates to a surfactant having the following formula (L):

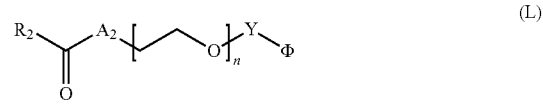

in which:
$R_2$ represents a linear hydrocarbon chain containing from 11 to 23 carbon atoms, preferably 17,
$A_2$ represents O or NH, preferably NH,
n represents an integer from 3 to 500, preferably from 20 to 200,
$Y_2$ represents a linking group (preferably one of the groups $Y_2$ mentioned here above), and
φ represents a functional group that is capable of binding to an agent of interest.

The invention also relates to an emulsion (referred to as emulsion 3) comprising a continuous aqueous phase and a dispersed phase, dispersed in the form of droplets containing an amphiphilic lipid, a surfactant having the following formula (L), optionally a solubilising lipid and optionally a co-surfactant (in particular the amphiphilic lipid/solubilising lipid/co-surfactant as defined here above).

The droplets of these emulsions 3 advantageously present φ groups that may be functionalised on the surface. It is therefore possible to graft the agents of interest (biological or therapeutic agents, fluorophoric or chromophoric agents, for example) on the surface of these droplets.

In one embodiment, the φ group is a $G_1$ or $G_2$ group as defined here above and the emulsion 3 corresponds to the emulsion 1 or 2 defined here above. When the material according to the invention is formed based on an emulsion 1 and an emulsion 2 comprising surfactants having the formula (LI) and (LII) corresponding to the formula (L), the radicals $L_1$-$X_1$—$H_1$— and $L_2$-$X_2$—$H_2$— of the surfactant having the formula (I) of the material correspond to the formula (IIC) as defined here above.

The surfactants having the formula (L) are advantageously easy to prepare (in particular by the formation of an ester or an amide between a fatty acid and a derivative of poly(ethylene glycol)).

In addition, an emulsion can generally be prepared with a greater amount of the surfactant having the formula (L) than of a surfactant type that is an ester or amide of fatty acids containing from 12 to 24 carbon atoms and of phosphatidyl ethanolamine (for example DSPE-PEG). As a consequence, the emulsion comprising a surfactant having the formula (L) advantageously comprises at the surface more of the groups φ that may be functionalised, and it is therefore possible to graft more of the agents of interest at the surface of the droplets.

Furthermore, it has evidently been demonstrated that the surfactant having the formula (L) used in an emulsion leaks out of the droplets to a lesser degree than a surfactant type that is an ester or amide of fatty acids containing from 12 to 24 carbon atoms and of phosphatidyl ethanolamine. This anti leakage effect is more significant for the surfactants having the formula (L) in which $A_2$ represents NH in comparison with those in which $A_2$ represents O. In addition, the emulsions comprising the surfactants in which $A_2$ represents NH are generally more stable than those comprising the surfactants in which $A_2$ represents O.

Formation of the Emulsions 1 and 2

The emulsions 1 and 2 as described may quite easily be prepared by means of dispersion of suitable quantities of oily phase and aqueous phase under the effect of a shearing action, typically by a process comprising the steps consisting of:
  (i) preparing the oily phase comprising of an amphiphilic lipid,
  (ii) preparing an aqueous phase comprising of a surfactant having the formula (LI) or (LII),
  (iii) dispersing the oily phase in the aqueous phase under the action of a shearing process that is sufficient to form an emulsion; and
  (iv) recovering the emulsion thus formed.

In this method, first of all the different oily constituents are mixed in order to prepare an oily premix for the dispersed phase of the emulsion. The mixing of the various different oily constituent substances may be optionally facilitated by bringing about the dissolution of one of the constituents or of the complete mixture in an appropriate organic solvent and subsequent evaporation of the solvent, in order to obtain a homogeneous oily premix for the dispersed phase. The choice of organic solvent depends on the solubility of the constituent substances. The solvents employed may be, for example methanol, ethanol, chloroform, dichloromethane, hexane, cyclohexane, dimethyl sulfoxide (DMSO), dimethylformamide (DMF) or even toluene. In the event a material for the administration of therapeutic agents is involved, use is made preferably of organic solvents that are volatile and/or non-toxic to humans. Furthermore, it is preferable to carry out preparation of the pre-mix at a temperature at which all of the ingredients are liquid.

Advantageously, the oily phase is dispersed in the aqueous phase in the liquid state. If one of the phases solidifies at ambient temperature, it is preferable to perform preparation of the mixture with one or preferably the two phases heated to a temperature greater than or equal to the melting temperature, with the two phases being heated to a temperature preferably lower than 80° C., and more preferably lower than 70° C., and even more preferably lower than 60° C.

The emulsification under the effect of shearing is preferably carried out by making use of a sonicator or a microfluidiser. Preferably, the aqueous phase and then the oily phase are introduced in the desired proportions into a suitable cylindrical vessel and the sonicator is then dipped into the medium and turned on and operated for a sufficient period of time in order to obtain an emulsion, which is usually a few minutes.

The emulsions 1 and 2 are generally nano emulsions. By means of the above process, a homogeneous nano emulsion is obtained in which the average diameter of the droplets is greater than 20 nm and less than 200 nm, in particular from 50 nm to 120 nm.

Preferably, the zeta potential of the emulsion is less than 25 mV in absolute value, that is to say, between −25 mV and 25 mV.

Prior to the preparation of the material according to the invention, the emulsions 1 and/or 2 may be diluted and/or sterilised, for example by filtration or dialysis. This step provides the ability to eliminate any optional aggregates that may have formed during the process of preparation of the emulsions.

The emulsions 1 and 2 thus obtained are ready to be used, after dilution as may be necessary. Quite obviously, it is possible to prepare the material according to the invention by accordingly implementing the process for an emulsion 1 and 2 that may be similar or identical.

The material according to the invention can be prepared regardless of the proportion of the continuous aqueous phase of the emulsions 1 and 2, which is advantageous in terms of cost of preparation because it is possible to prepare the material based on emulsions 1 and 2 wherein the proportion of phase that is dispersed is low. The ratio between the dispersed phase and the aqueous phase may thus vary to a large extent in the emulsions 1 and 2. The dispersed phase of the emulsions 1 and 2 (optional oil/optional solubilising lipid/amphiphilic lipid/optional co-surfactant/optional lipophilic agent of interest/surfactant having the formula (LI) or (LII)) represent generally between 0.1% and 90% by weight relative to the total weight of the emulsion, that is to say, relative to the weight of the continuous aqueous phase and the dispersed oily phase.

According to the reactions involved in the formation of the surfactant having the formula (I), the formation of the material according to the invention may take place in the presence of a cross-linker, by changing of the pH, the action of light or some other means.

In practice, beyond a certain total proportion of aqueous phase upon bringing into contact the emulsions 1 and 2 (which varies from one material to another, in particular according to the nature and the proportions of the various components of the material), it may be noted that there is formation on the one hand, of a material comprising a dispersed phase dispersed in the form of droplets in a continuous aqueous phase, and on the other hand, an aqueous phase that is essentially, generally completely, free of droplets.

[Uses]

The material according to the invention has various applications that are highly varied.

According to a third object, the invention relates to the use of the material as defined here above as a membrane or as a coating.

Advantageously, the material according to the invention may be prepared from biocompatible constituent components and hence be biocompatible. Thus, it may for example be used as a coating for an object or a non biocompatible material intended to be implanted in the body of a human or an animal, such as a prosthesis, an implant or an implantable electrode. The invention therefore also relates to a prosthesis, an implant or an implantable electrode coated by the material according to the invention.

Use of the Material Including a Surfactant Having the Formula (I) Wherein the G Group Includes a Cleavable Function According to a fourth object, the invention relates to the use of the material including a surfactant having the formula (I) wherein the G group includes a cleavable function such as defined here above, as a valve.

Thus, when a material as defined here above is introduced into a closed environment (pipe, tube, capillary), it may stop or modify (generally slow down) the flow of a fluid, preferably a liquid.

If the material is placed under appropriate conditions that allow for the cleaving of the cleavable function of the G group of the surfactant having the formula (I) (for example by bringing into contact a chemical compound or an enzyme capable of cleaving the function of the G group, or in electrochemical conditions, with conditions related to pH, light or temperature that enable this cleavage, as explained here above), the covalent bonds between the droplets of the material according to the invention are cleaved. Thus, the droplets are no longer bound to each other and the material disaggregates, which has the consequential effect of increasing the flow of fluid. Preferably, the fluid whose flow is modified or stopped by the material according to the invention used as a valve, comprises or is constituted of an aqueous phase.

When the reaction of cleavage of the cleavable function of the G group of the surfactant having the formula (I) is reversible, after the said function has been cleaved, by placing the material under conditions that make possible the re-formation of the cleavable function of the G group of the surfactant having the formula (I) (and thus the re-formation of the covalent bonds between the droplets), it is possible to close the valve. It is then possible to open and close the valve again.

According to a fifth object, the invention also relates to the use of the material including a surfactant having the formula (I) wherein the G group includes a cleavable function as defined here above, as a mask for preparing biochips. Indeed, the material according to the invention is then a coating that is destructible (by means of cleavage of the said function) and optionally eventually reformable (by means of reformation of the said function) and suitable for such use. Use may be made for example of the methods described in Nie, Z H, Kumacheva, E, Patterning Surfaces with Functional Polymers, Nature Materials 2008, 7 (4), 277-290; or Hoffmann, J et al, Photopatterning of Thermally Sensitive Hydrogels Useful for Microactuators. Sensors and Actuators, A: Physical, 1999, 77 (2), 139-144 by using the material according to the invention in place of the materials described therein.

Use of the Material Comprising an Agent of Interest

According to a sixth object, the invention relates to the use of the material comprising an agent of interest as defined here above, as a chemical detector. Indeed, when the agent of interest is a chemical detection agent, the material according to the invention can be used to detect and/or quantify the presence of a chemical compound (analyte, pollutant, metal, etc).

According to a seventh object, the invention relates to the use of the material comprising an agent of interest as defined here above, as a chemical sensor. When the agent of interest is a chemical sensing agent, the material according to the invention can be used as a chemical sensor, in particular for purifying a medium or as a scavenger (chemical sensing agent contained in the material that reacts with the chemical compound that it is desired to eliminate (for example a pollutant, or during a chemical reaction, a product of a secondary reaction or an excess of reagent)).

According to an eighth object, the invention relates to the use of the material comprising an agent of interest as defined here above, for the delivery of the agent of interest, in particular the delivery ex vivo, in vivo or in vitro of agents of interest. Mention may be made in particular of the delivery of an optical agent, a phytosanitary or plant protection agent, a taste/odour masking agent, or a cosmetic agent. The case of the delivery of a therapeutic agent is described here below.

When the material according to the invention comprises a plurality of agents of interest, the invention relates to the use thereof for the delivery of these agents interest where delivery may be combined, simultaneous, or carried out separately at different times.

In the embodiment wherein the material comprises a hydrophilic agent of interest and a lipophilic agent of interest, the invention relates to the use thereof for the delivery of the hydrophilic agent of interest and the lipophilic agent of interest, where delivery thereof may be combined, simultaneous, or carried out separately at different times.

According to a ninth object, the invention relates to the use of the material comprising a catalyst type agent of interest as defined here above, as a catalyst.

Use of the Material Comprising a Therapeutic Agent

According to a tenth object, the invention relates to a material comprising a therapeutic agent for the use thereof for treating or preventing a disease. Indeed, the material may be used for the administration of at least one therapeutic agent to a human or an animal. The invention also relates to the material comprising a therapeutic agent used as a medicament, and to a method of therapeutic treatment consisting of the administration to a human or an animal in need thereof of an effective amount of the material comprising a therapeutic agent for treating or preventing a disease.

Since the material according to the invention may be prepared exclusively from constituent components approved for use in humans or animals, it is particularly advantageous for a parenteral route of administration. However, it is also possible to consider the administration thereof by other routes, including oral or topical routes.

The techniques described in the published paper by Hoffman, The Origins and evolution of "controlled" drug delivery systems, Journal Controlled release 132 (2008) 153-163, may in particular be used, by replacing the materials described therein with the material according to the invention.

For example, the material may be administered by making use of a syringe or a transdermal patch (known as a "patch"), this formulation is thus particularly suitable because the material has an adhesive nature.

Use of the Material Comprising a Hydrophilic Therapeutic Agent and a Lipophilic Therapeutic Agent According to an eleventh object, the invention relates to the material comprising at least one hydrophilic therapeutic agent and at least one lipophilic therapeutic agent for use thereof for the administration of at least one hydrophilic therapeutic agent and at least one lipophilic therapeutic agent to a human or an animal in order to treat or prevent a disease.

Indeed, the droplets, and in particular the nano droplets, charged with therapeutic agents constitute a solution that is ideal for overcoming the low degree of selectivity of medicinal products, in particular anticancer medicinal products, by making possible by means of the passive targeting and/or active targeting of the cancerous tissues, and thus providing the ability to reduce the severe side effects.

Certain treatments require the administration of multiple therapeutic agents, at times having different rates of solubility, which then involves multiple administration, which is a source of discomfort and a significant loss of time for patients. In addition, it is often desirable for the various different therapeutic agents to not all be released at the same time, or even not in the same location.

The development of formulations that make possible the delivery of multiple therapeutic agents is thus desirable.

The material according to the invention provides the ability to deliver in one single administration/application two or more therapeutic agents, with different release times. At lipophilic therapeutic agent is released at a time $t_{lipophilic}$, that may be identical to or different from $t_{hydrophilic}$.

Indeed, the hydrophilic therapeutic agent is located essentially in the continuous aqueous phase of the material. It is trapped between the droplets of the dispersed phase. When the material is administered, it comes in contact with the physiological fluids (blood, plasma, etc) that are exchanged with the continuous aqueous phase of the material, that thereby releases the hydrophilic therapeutic agent. The time of release of the hydrophilic therapeutic agent $t_{hydrophilic}$ is related to the time of exchange between the continuous aqueous phase of the material and the physiological fluids, to the time of diffusion of the hydrophilic therapeutic agent through the material and sometimes to the time of release of the droplets $t_{droplet}$ when the surfactant having the formula (I) includes functions that are capable of being cleaved in the physiological medium (with the cleavage of these functions then leading to the cleaving of the covalent bonds between the droplets and to the disaggregation of the three dimensional network of the material).

In addition, the lipophilic therapeutic agent is essentially located in the dispersed phase of the material, either in the interior of the droplets, or on the surface of the droplets. The time of release of the lipophilic therapeutic agent $t_{lipophilic}$ is related to the time of diffusion of the lipophilic therapeutic agent to the exterior of the droplets, to the time of degradation of the droplets and sometimes to the time of release of the droplets $t_{droplet}$.

The locations of release of the hydrophilic therapeutic agents $L_{hydrophilic}$ and the lipophilic therapeutic agents $L_{lipophilic}$ may also be different. In particular, if the surfactant having the formula (I) includes functions that are capable of being cleaved in the physiological medium when the material disaggregates at the site where it has been administered, the hydrophilic therapeutic agent is then released at the location of administration and the droplets that are released from the material are carried away by the physiological fluid (blood, plasma), to another site of the subject, wherein the lipophilic therapeutic agent will then be released.

Thus, by adapting the composition of the material according to the invention (nature of the constituent components, mass fraction of the constituent components, size of droplets, etc), based on the physical and chemical properties of the agents, as explained here below, it is advantageously possible to modify these times of release $t_{hydrophilic}$ and $t_{lipophilic}$ as well as the locations $L_{hydrophilic}$ and $L_{lipophilic}$.

Most certainly, if the material includes more than one hydrophilic therapeutic agent and/or more than one lipophilic therapeutic agent, it is possible to appropriately adapt the composition of the material so as to adjust the times of release of each agent, and to ensure that these latter differ from each other. It would be possible in particular to act on the parameters of the composition of the material that influence the release of the hydrophilic agents of interest or the lipophilic agents of interest in order to ensure that $t_{hydrophilic\ 1}$ differs from $t_{hydrophilic\ 2}$ and/or that $t_{lipophilic\ 1}$ differs from $t_{lipophilic\ 2}$ as explained here below. The different locations of release of the agents may also be influenced and made to differ from each other.

The time of release of the hydrophilic therapeutic agent $t_{hydrophilic}$ depends on the composition of the material, in particular:
- on the mass fraction of the dispersed phase relative to the total weight of the material;
- on the number of alkoxylated units of the alkoxylated co-surfactant (and thus on the length of the alkoxylated chain of the alkoxylated co-surfactant);
- on the diameter of the droplets;
- on the nature of the surfactant having the formula (I).

The time of release of the lipophilic therapeutic agent $t_{lipophilic}$ is related to the time of diffusion of the lipophilic therapeutic agent to the exterior of the droplet and to the time of release of the droplets $t_{droplet}$. The time of release of the lipophilic therapeutic agent $t_{lipophilic}$ depends:
- on the mean diameter of the droplets, as described in particular in Williams, Y. et al. Small (2009); 5(22): 2581-8, Choi, H S et al. Nanoletters (2009) 9(6): 2354-9 and Massignani, M et al. Small. (2009) 5(21): 2424-32. The droplets of the material according to the invention are advantageously monodisperse in order to provide for a homogenous release over time of the lipophilic therapeutic agent.
- on the nature of the components of the oily phase, in particular on the solubilising lipid;
- on the physical and chemical characteristics of the lipophilic therapeutic agent (Nel, A E et al. Nature Materials 8 (2009) pp 543-557), in particular on its log P, which affects the location of the lipophilic therapeutic agent within the interior or on the surface of the droplet. A highly lipophilic therapeutic agent remains within the droplet and is released only when it is degraded through chemical degradation (by hydrolysis of the components of the droplets following a resultant significant increase or decrease of the medium, for example if the droplets get internalised within the interior of the cells by passing through the lysosomes) or through enzymatic degradation by lipases (Olbrich, C et al. International Journal of Pharmaceutics 237 (2002) pp 119-128 and Olbrich, C International Journal of Pharmaceutics 180 (1999) pp 31-39).

Generally, the release time of the hydrophilic therapeutic agent $t_{hydrophilic}$ is less than the release time of the lipophilic therapeutic agent $t_{lipophilic}$.

The location of the release of the hydrophilic therapeutic agent $L_{hydrophilic}$ is generally the location of administration of the material.

The location of the release of the lipophilic therapeutic agent $L_{lipophilic}$ is either the location of administration (in this case, $L_{hydrophilic}$ and $L_{lipophilic}$ are generally identical) or another site in the body of the human/animal subject, in particular when the droplets released from the material are carried away by the physiological fluid (interstitial fluid, lymph fluid, blood) to another site. Quite obviously, the location of the release of the lipophilic therapeutic agent also depends on the physical and chemical properties:

on the zone of administration of the material, in particular on the density of tissues and on the presence or absence of physiological barriers, and on the nature and the physical and chemical properties of the lipophilic therapeutic agent itself. Thus, when more than one lipophilic therapeutic agent is used in the material, each lipophilic therapeutic agent has a location of release that is specific to itself.

It is possible in particular, to modulate $L_{Lipophilic}$ by using in the material a polyalkoxylated co-surfactant comprising a grafted biological targeting ligand, which will enable the possibility of the droplets, and therefore the lipophilic therapeutic agent, to be directed to the desired target.

A number of embodiments of the use as a medicinal product of the material according to the invention comprising a hydrophilic therapeutic agent and a lipophilic therapeutic agent may be envisaged.

For example, one of the therapeutic agents may be a pharmaceutical active ingredient for the treatment of the disease being targetted, and the other may be a therapeutic agent that provides the ability to reduce the side effects, particularly those associated with the said pharmaceutical active ingredient.

A material according to the invention in which the hydrophilic therapeutic agent is a wound healing, antibacterial or anti inflammatory agent and the lipophilic therapeutic agent is an anti cancer agent, may in particular be used for the treatment post-resection of a tumour. This material is applied after a tumour resection operation on the site of resection of the tumour.

The healing, antibacterial or anti-inflammatory hydrophilic therapeutic agent is rapidly released in order to decrease the side effects of the resection and to promote the healing process.

The anti cancer lipophilic therapeutic agent is released later, generally during the first hours following the application of the material, and treats the clusters of remaining tumoral cells which have not been excised. It is actually often difficult to completely clear out the whole of the tumour during resection. The material thus provides for a comprehensive treatment of the tumoral area.

The droplets comprising the anti cancer lipophilic agents of the dispersed phase may also reach and join in with the lymphatic and blood circulation and act to treat the possible cancer cells that may be circulating in the circulatory system and serve as the source of metastases.

In particular, the co-surfactant of the material may include a biological targeting ligand for targeting the cancer cells in order to be able to more efficiently target the cancer cells.

Furthermore, a material according to the invention in which the hydrophilic therapeutic agent is an agent stimulating the immune system and the lipophilic therapeutic agent is an anti cancer agent, may notably be used for treatment of a tumour after cryogenic treatments.

Cryogenic treatment for tumour consists of the injection of a cryogenic liquid into a tumour by means of a syringe. The tumoral cells are killed with this treatment and remain inside the body of the treated subject.

The aforementioned material may increase the efficacy of the treatment. The hydrophilic agent that stimulates the immune system is rapidly released in order to activate the immune system and the lipophilic anti cancer agent is released later on, and acts to enable the elimination of the tumour cells that are still alive. There again, the droplets comprising the anti cancer lipophilic agent of the dispersed phase may reach and join in with the lymphatic and blood circulation and act to treat the possible cancer cells that may be circulating in the circulatory system and serve as the source of metastases. In addition, the co-surfactant of the material may include a biological targeting ligand for targeting the cancer cells in order to be able to more efficiently target the cancer cells.

The invention shall be described in more detail by means of examples and accompanying figures, which show the following:

DESCRIPTION OF PREFERRED EMBODIMENTS

Examples

Example 1

Figure 1:
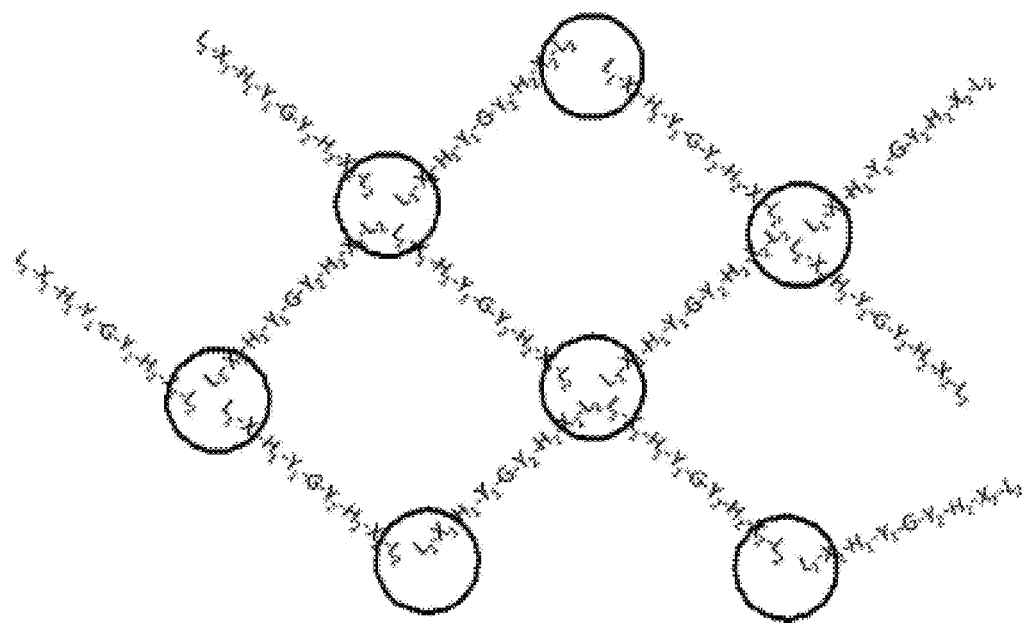
FIG. 1 shows a diagram illustrating the positioning of the surfactant having the formula (I) in which v and w represent 1 and the droplets of the material according to the invention.
Figure 2:
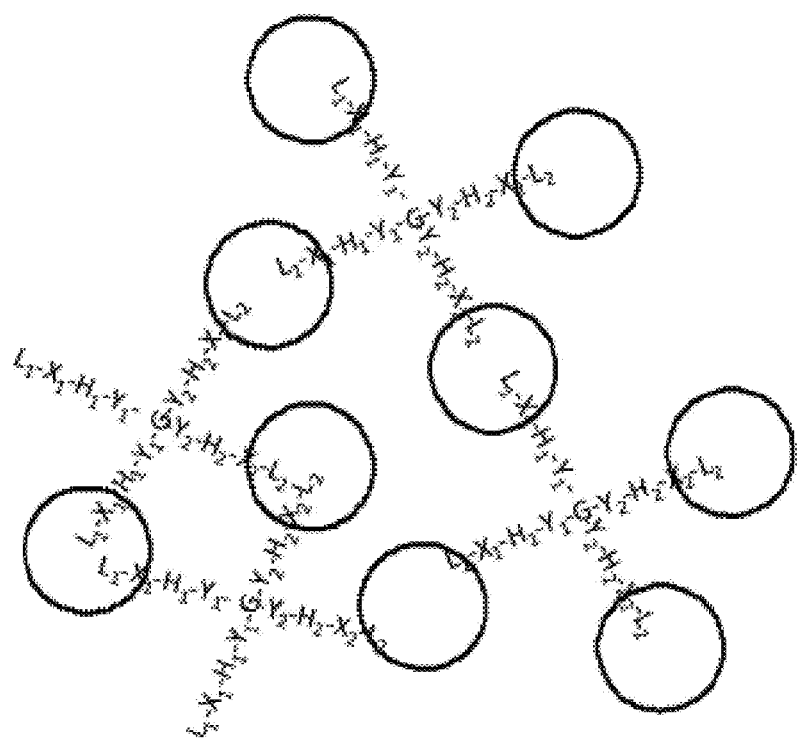
FIG. 2 shows a diagram illustrating the positioning of the surfactant having the formula (I) in which and v and w represent 2 and the droplets of the material according to the invention.

Preparation of a Material Including a Surfactant Having the Formula (I) Including a G Group Comprising a Reversible Cleavable Function Preparation of a Surfactant Having the Formula (LII)
A surfactant having the formula (LII) wherein:
$L_2$ is fatty acid containing 18 carbon atoms (stearic acid);
$H_2$ is a poly(ethylene oxide) comprising 100 units of ethylene oxide;
$G_2$ represents a group —S—S-pyridinyl;
$X_2$ represents —NH—;
$Y_2$ represents —$CH_2$—$CH_2$—NH—CO—$CH_2$—$CH_2$—
was prepared by following the reaction scheme as follows:

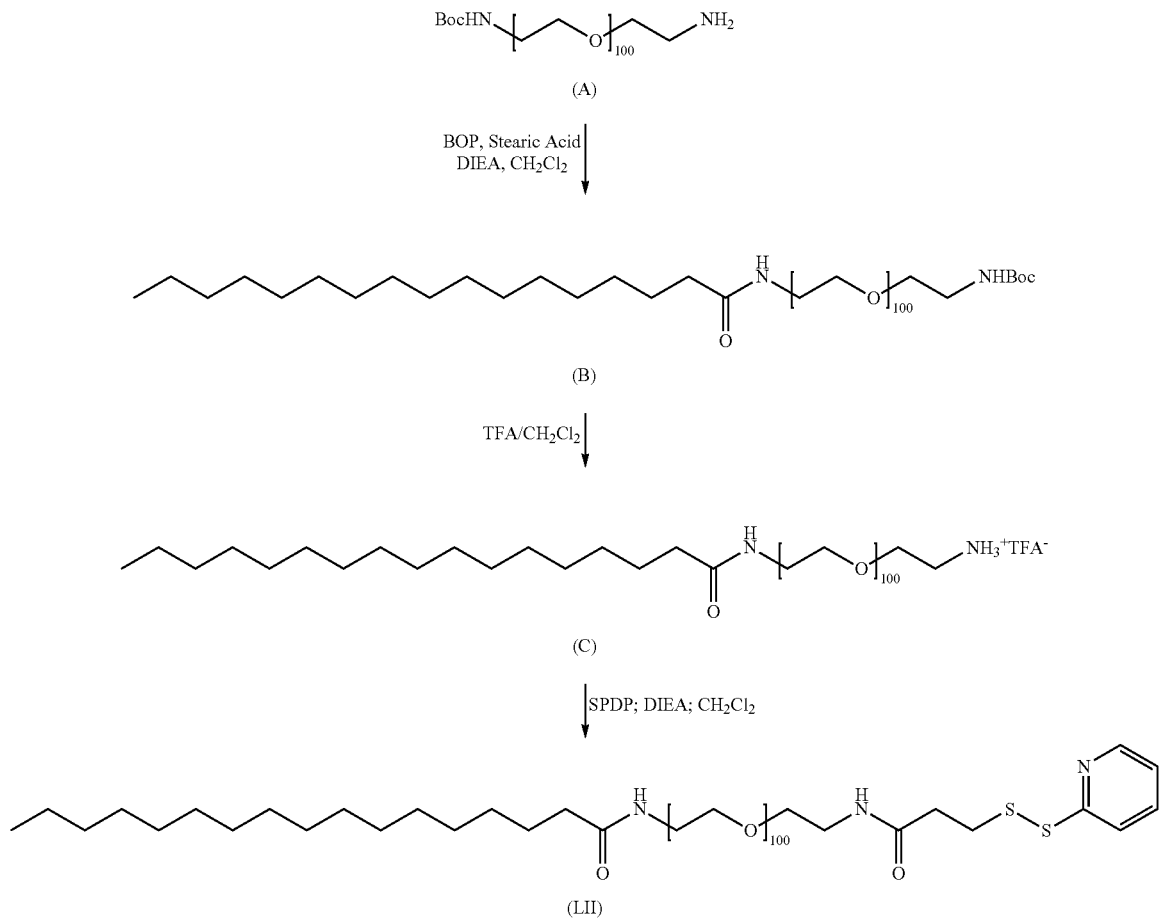

Synthesis of the Compound (B)

The stearic acid (2 g; 0.6 mmol) and Benzotriazole-1-yl-oxy-tris-(dimethylamino)-phosphonium hexafluorophosphate (BOP) (265.2 mg, 0.6 mmol) were dissolved in $CH_2Cl_2$ (15 mL). After 10 minutes of stirring, BocNH-PEG100-$NH_2$ (MW: 4928, 2 g, 0.4 mmol) (compound (A)) and diisopropylethylamine (DIEA) (104.5 mL, 0.6 mmol) were added to the reaction medium. The disappearance of the starting amine was verified by means of thin layer chromatography (TLC) ($CH_2Cl_2$/MeOH). After stirring for 2 hours, the product was precipitated in cold ether, dissolved in a little water and then dialysed against Milli Q water (cut off 1000). The solution was then recovered and the water was removed either by means of evaporation (ethanol as azeotrope) or by means of lyophilisation, in order to provide 1.5 g of compound (B) (white powder), that is a yield of 70%.

TLC ($CH_2Cl_2$/MeOH 9/1): Rf=0.5

$^1$H NMR (300 MHz; CDCl3): d: 0.87 (t; J=6.5 Hz; 3H; C$\underline{H}_3$—$CH_2$); 1.24 (m; 28H; 14C$\underline{H}_2$); 1.44 (s; 9H; C(C$\underline{H}_3$)$_3$); 1.67 (quin; 2H; C$\underline{H}_2$—$CH_2$—CONH); 2.42 (t; J=7.5 Hz; 2H; C$\underline{H}_2$—CONH); 3.3 (t; J=5.0 Hz; 2H; BocNH—C$\underline{H}_2$); 3.45-3.8 (m; 362H; ×C$\underline{H}_2$(PEG). $CH_2$CONH—C$\underline{H}_2$)

Synthesis of the Compound (C)

The compound (B) (1.5 g, 0.29 mmol) was dissolved in 10 mL of dichloromethane and 4 mL of trifluoroacetic acid (TFA). The conversion of compound (C) was monitored by TLC (ninhydrin developer). After stirring for 1 hour, the solvent was evaporated by means of coevaporation with toluene (which eliminates the TFA). The product was dried under vacuum in order to provide 1.3 g of compound (C) (white powder), that is a yield of 86.7%.

TLC ($CH_2Cl_2$/MeOH 9/1): Rf=0.27

$^1$H NMR (300 MHz; CDCl3): d: 0.87 (t; J=6.5 Hz; 3H; C$\underline{H}_3$—$CH_2$); 1.24 (m; 28H; 14C$\underline{H}_2$); 1.60 (quin; 2H; $CH_2$—$CH_2$—CONH); 2.15 (t; J=7.5 Hz; 2H; C$\underline{H}_2$—CONH); 3.17

(bt; 2H; C$\underline{H}_2$—NH$_3^+$); 3.4 (m; 2H; CH$_2$CONH—C$\underline{H}_2$); 3.5-3.8 (m; 360H; xC$\underline{H}_2$(PEG)); 6.14 (bs; 1H; N$\underline{H}$CO); 7.9 (bs; 2H; N$\underline{H}_2$/N$\underline{H}_3^+$)

Synthesis of the Surfactant (LII)

Under argon, the compound (C) (0.5 g, 0.1 mmol) and diisopropylethylamine, DIEA (52 mL; 0.3 mmol) were dissolved in dichloromethane (10 mL). After 5 minutes of stirring Succinimidyl 3-(2-pyridyldithio)propionate (SPDP) (93 mg, 0.3 mmol) was added into the reaction medium. The disappearance of the amine was monitored by TLC (CH$_2$Cl$_2$/MeOH 9/1). After 1 hour of reaction, the product was precipitated twice in ether in order to provide after filtration 400 mg of surfactant (LII) (yellowish powder) that is a yield of 76%

TLC (CH$_2$Cl$_2$/MeOH 9/1): Rf=0.42

1H NMR (300 MHz; CDCl3): d: 0.88 (t; J=6.5 Hz; 3H; C$\underline{H}_3$—CH$_2$); 1.25 (m; 28H; 14C$\underline{H}_2$); 1.63 (quin; 2H; C$\underline{H}_2$—CH$_2$—CONH); 2.17 (t; J=7.5 Hz; 2H; C$\underline{H}_2$—CONH); 2.62 (t; J=7 Hz; 2H; C$\underline{H}_2$—SS); 3.09 (t; J=7 Hz; 2H; NHCO—C$\underline{H}_2$—CH$_2$—SS); 3.42 (m; 2H; C$\underline{H}_2$—NHCO); 3.48-3.8 (m; 360H; xC$\underline{H}_2$(PEG); C$\underline{H}_2$—NHCO); 6.11 (bt; 1H; NH); 6.79 (bt; 1H; NH); 7.11 (m; 1H; CHpyr); 7.67 (m; 2H; 2CHpyr); 8.49 (m; 1H; CHpyr)

Preparation of Emulsions 2 Comprising a Surfactant Having the Formula (LII)

The emulsions 2 were prepared by following the procedures described in the document WO 2010/018223 with the compositions shown in the Table 1, the complete dissolution of Myrj S40 and the surfactant having the formula (LII) with the need to heat the solution to 55° C. and by mixing and then emulsifying the aqueous and oily phases by means of sonication in accordance with the parameters described in the Table 2.

TABLE 1

Compositions of the Emulsions 2

| | Supplier | Emulsion 2 (20%) | Emulsion 2 (15%) | Emulsion 2 (10%) | Emulsion 2 (5%) |
|---|---|---|---|---|---|
| Soybean Oil (mg) | CRODA | | | 68 | |
| Suppocire ® NB (mg) | Gattefossé | | | 272 | |
| Lecithin (mg) | Lipoïd | | | 65 | |
| PBS Water 1X (mL) | — | | | 2.5 | |
| Myrj S40 (mg) | CRODA | 276 | 293 | 310 | 328 |
| surfactant (LII) (mg) | — | 69 | 52 | 35 | 17 |
| m (surfactant (LII))/ [m (surfactant (LII) + m (Myrj S40)) * (%) | — | 20 | 15 | 10 | 5 |
| % dispersed phase | | | | 23 | |
| DiI (mg) | | | | 4 | |

* Ratio of the mass of surfactant having the formula (LII) over the mass of the ensemble (surfactant having the formula (LII)/Myrj S40) (in %). The mass of the ensemble (surfactant having the formula (LII)/Myrj S40) is 345 mg for all the emulsions.

TABLE 2

| Sonication Parameters used | | | | |
|---|---|---|---|---|
| Volume of the batch | Probe (φ) | Power Pmax | Sonication Time | Pulse on/off |
| 3.25 mL | 3 mm | 28% | 5 min | 10 s/30 s |

In order to enable better visual observation of the stability and the formation of the material subsequently formed, the droplets were stained by incorporation of a fluorophore, namely 3,3-dioctadecylindocarbocyanine (DiI) (4 mg/emulsion)).

Preparation of Emulsions 1 Comprising a Surfactant Having the Formula (LI)

The emulsions 1 comprising a surfactant having the formula (LI) of the following formula:

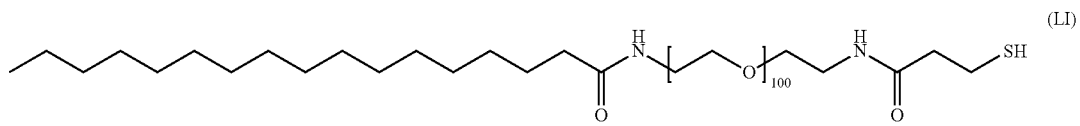

was obtained from the emulasion 2 prepared here above.

The thiol group of the surfactant (LI) was obtained by deprotection of the —S—S-pyridinyl functions with a reducing agent dithiothreitol (DTT).

For example, for the emulsion 1 (20%) obtained from the emulsion 2 (20%) mentioned above, 1.5 mL were taken of the emulsion 2 (20%) to which was added 23 mg of DTT (which is 20 molar equivalents/SSpyr). The reaction was then left to be stirred (moving stir plate) for 2 hours Preparation of the Material According to the Invention from the Emulsions 1 and 2

The emulsions 1 and 2 prepared above were purified by means of dialysis against PBS 1× (MW Cut off 12000-14000 Da, 500 mL; 24 hours).

The size of droplets of the emulsions was determined through measurement by dynamic light scattering, DLS (Zeta Sizer Nano ZS, Malvern). The emulsions have a similar size distribution with sizes of droplet of 65 nm with a polydispersity index of 0.112.

The emulsions have optionally been diluted by the addition of aqueous phase, in order to obtain dispersed oily phase in percentages of 1%, 5%, 15% or 23%.

In order to form the material according to the invention, the emulsions 1 and 2 having:
- the same proportion of dispersed phase, and
- ratios of the mass of surfactant having the formula (LII) over the mass of the ensemble (surfactant having the formula (LII)/Myrj S40), and of the mass of surfactant having the formula (LI) over the mass of the ensemble (surfactant having the formula (LI)/Myrj S40), which are identical, have been used.

An equivalent volume of emulsions 1 and 2 was mixed, the solution was then stirred and a homogeneous material formed rapidly after 2 to 4 minutes of stirring. A disulfide bond was formed between the surfactants having the formula (LI) of the emulsion 1 and (LII) of the emulsion 2 in order to form the surfactant having the following formula (I):

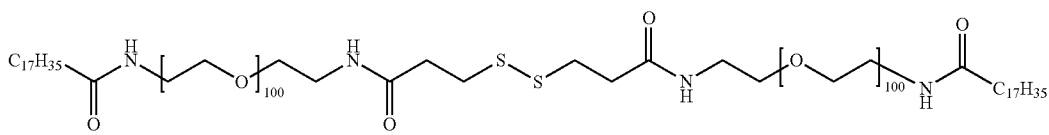

This surfactant having the formula (I) (wherein G represents —SS—) ensures the covalent bonding between the droplets of the material formed.

Several tests were carried out with various different percentages of the dispersed oily phase (1%, 5%, 15% or 23%).

Figure 3:
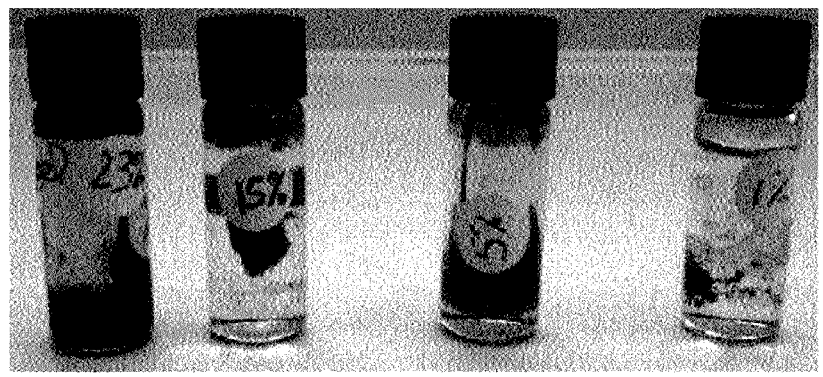
FIG. 3 shows photographs of the materials described in the Example 1 obtained with the emulsions 1 and 2 and comprising the dispersed oily phase of 1%, 5%, 15% or 23%.

The appended FIG. 3 shows four pictures of the materials obtained with the emulsions 1 and 2 and comprising dispersed oily phases of 1%, 5%, 15% or 23%. No matter what the proportions of dispersed phases of the emulsions 1 and 2 are, the material is formed rapidly.

Where the dispersed phase is greater than 15%, upon bringing about contacting of the two emulsions, the procedure carried out was as follows in order to obtain a homogenous and uniform material:

Vortexing

Heating in order to re-fluidify

Vortexing

Heating in order to re-fluidify

Vortexing

Letting stand

Influence of the Ratio m (Surfactant (LII))/[m (Surfactant (LII)+m (Myrj S40))

Tests for preparation of the material according to the invention were carried out based on emulsions having ratios m (surfactant (LII))/[m (surfactant (LII)+m (Myrj S40)) that were different (the ratios of the mass of surfactant having the formula (LII) over the mass of the ensemble (surfactant having the formula (LII)/Myrj S40) of the emulsion 2, and of the mass of surfactant having the formula (LI) over the mass of the ensemble (surfactant having the formula (LI)/Myrj S40) of the emulsion 1 being always identical) in order to obtain materials having a ratio m (surfactant (I))/[m (surfactant (I)+m (Myrj S40)) that are different, namely 5%, 10%, 15% and 20% as mentioned in the Table 1. The material is formed more easily when the said ratio is greater than or equal to 15%.

Preparation of the Material According to the Invention from Emulsions 1 and 2 Comprising Droplets of Larger Size (125 nm)

The preparation of an emulsion 2 as described here above was reproduced with the same components, but by ensuring varying of the proportions thereof as indicated in the following Table 3 and with identical sonication parameters.

TABLE 3

Compositions of the Emulsion 2 (20%) bis

| | Emulsion 2 (20%) bis |
|---|---|
| Soybean Oil (mg) | 150 |
| Suppocire ® NB (mg) | 450 |
| Lecithin (mg) | 45 |
| PBS Water 1 X (mL) | 2.39 |
| Myrj S40 (mg) | 172 |
| surfactant (LII) (mg) | 43 |
| m (surfactant (LII))/ [m (surfactant (LII) + m (Myrj S40)) * (%) | 20 |
| DiI (mg) | 4 |

The size of droplets of the emulsion 2 (20%) bis obtained was measured by means of DLS (Zeta Sizer Nano ZS, Malvern). They have a size distribution with a mean of 125 nm and a polydispersity index of 0.13.

There again, the emulsion 1 (20%) bis comprising a surfactant having the formula (LI) of the following formula:

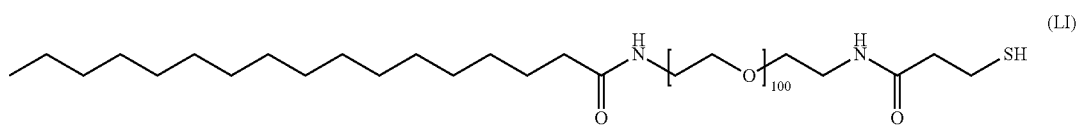

was obtained from the emulsion 2 (20%) bis prepared here above as follows:

1.625 mL was taken of the emulsion 2 (20%) bis to which was added 16 mg of DTT (that is 22 molar eq/SSpyr) in order to form the emulsion 1 (20%) bis comprising the surfactant having the formula (LI). The reaction was left to be stirred (moving stir plate) for a period of 15 hours.

Thereafter, the emulsion 1 (20%) bis and the emulsion 2 (20%) bis were set to be dialysed against PBS 1×2 times (MW Cut off 12000-14 000 Da; 500 mL; 24 hours). The material was then prepared from the emulsion 1 (20%) bis and the emulsion 2 (20%) bis by following the same protocol as described here above.

This experiment shows that it is possible to prepare a material comprising droplets of different sizes.

Example 2

Test of Resistance to Dilution of the Material Based on Example 1

The material described in the Example 1 prepared from emulsions 1 and 2 both of which having 23% of dispersed phase and in which m (compound (I))/[m (compound (I)+m (Myrj S40))]=20% was recovered with a spatula, then transferred to a pill container, thereafter 1 mL of an aqueous solution of PBS (1×) was added thereto.

The resistance to dilution of the material is total, the material retains its structure even after dilution. The density of the material is less than that of water (the float material). If a strong agitation (that is to say at 3000 rpm/min on a vortex device Vortex Top-Mix 3, Fischer Scientific) is applied, the material gets fragmented into small pieces and then ends up getting re-constituted through the process of creaming after a period of about 6 hours.

Example 3

Tests of Stability the Material Based on Example 1

Figure 4:
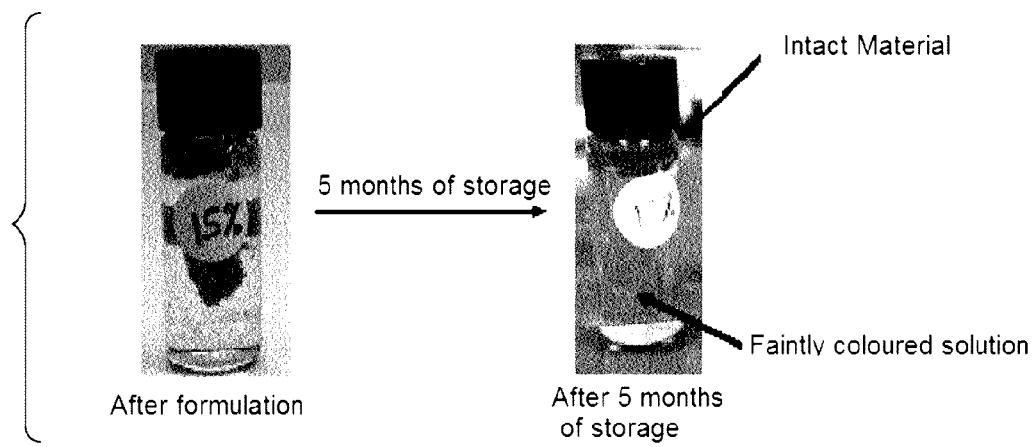
FIG. 4 shows photographs of a mixture (material in the Example 1 and aqueous solution of Phosphate Buffer Saline—PBS) immediately after the addition of PBS, and after 5 months of storage.

The material described in Example 1 prepared from emulsions 1 and 2 both of which having 23% of dispersed phase and in which m (compound (I))/[m (compound (I)+m (Myrj S40))]=20% was recovered with a spatula, then transferred to a pill bottle, thereafter 1 mL of an aqueous solution of PBS (1×) was added thereto. Subsequently, the mixture obtained was stored for a period of 5 months at ambient temperature (25° C.). the photographs included in the FIG. 4 show that the colouration of the PBS solution remained faint even after 5 months of storage, which demonstrates that the droplets of the material remain bonded to each other and that the material according to the invention is stable.

The test had been repeated by replacing the aqueous solution of PBS with physiological serum (foetal calf serum) (Sigma Aldrich). The material remains intact in this medium for a period of 16 hours at 37° C. or 50° C., which demonstrates the stability thereof in physiological media.

Example 4

Cleavage of the G Group of the Surfactant Having the Formula (I) of the Material Described in Example 1

The material described in the Example 1 prepared from emulsions 1 and 2 both of which having 23% of dispersed phase and in which m (compound (I))/[m (compound (I)+m (Myrj S40))]=20% was used.

The disulfide group of the surfactant having the formula (I) of the material was cleaved with a disulfide bond reducing agent, dithiothreitol or Cleland's reagent.

Then 10 mg of DTT (dithiothreitol or Cleland's reagent) was added in order to reduce the intra-particle disulphide bonds over the entire material. The occurrence then observed was the immediate dissolution of the material, that is to say a disaggregation of the droplets which were distributed throughout the entirety of the aqueous phase of the medium. The size of the droplets present in the solution once the cleavage of the disulfide bonds had taken place, is identical to that of the droplets of the emulsions 1 and 2 (prior to creation of the covalent disulfide bonds.)

Figure 5:
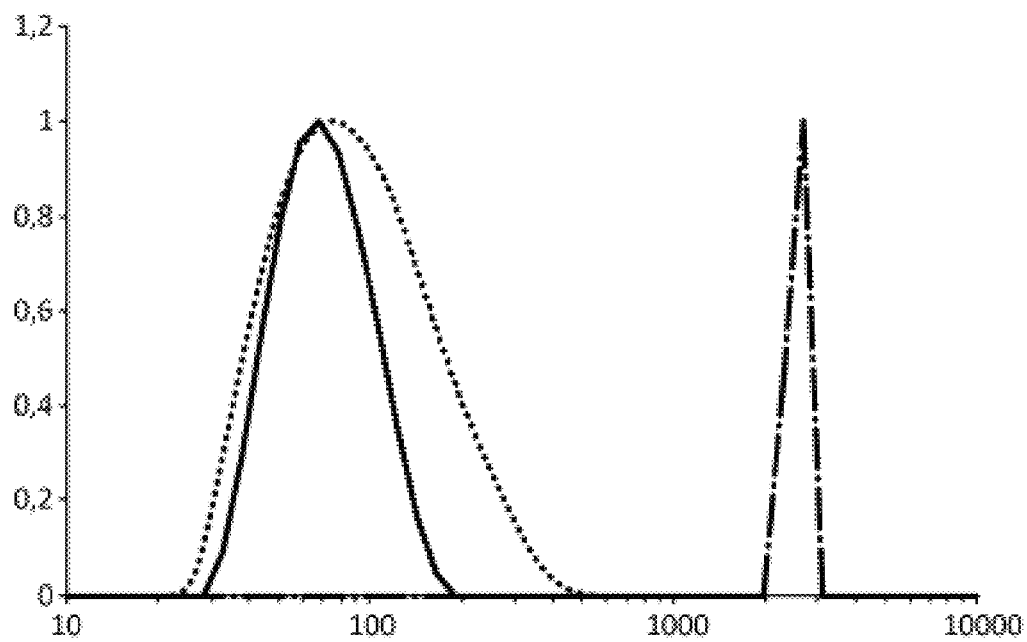
FIG. 5 shows the results of analysis by DLS (Dynamic Light Scattering), that is, the normalised intensity in % as a function of the size in nm, of the emulsion 1 (solid line) of the material according to the invention (solid line/dotted broken line) and of the emulsion obtained after cleavage of the disulfide function of the material (dotted line).

The colloidal nature of the emulsion thus obtained was verified by means of DLS (dynamic light scattering) (Zeta Sizer Nano ZS, Malvern). The size of the suspended droplets is substantially the same for the emulsion 1 and for the emulsion obtained after cleavage of the disulfide function of the material, whereas the size of the suspended aggregates (clusters of the droplets forming the material) is much greater (FIG. 5).

Example 5

Emulsions Comprising a Surfactant Having the Formula (L)

Demonstration of Evidence of the Ability to Introduce More of the Surfactants Having the Formula (L) in an Emulsion than Surfactants of the DSPE-PEG Type Preparation of a Surfactant Having the Formula (L) Wherein $R_2$ Represents $C_{17}H_{35}$, $A_2$ Represents O, n Represents 100 and φ Represents a Succinimidyl Group A surfactant having the formula (L) wherein $R_2$ represents $C_{17}H_{35}$, $A_2$ represents O, n represents 100 and φ represents a succinimidyl group

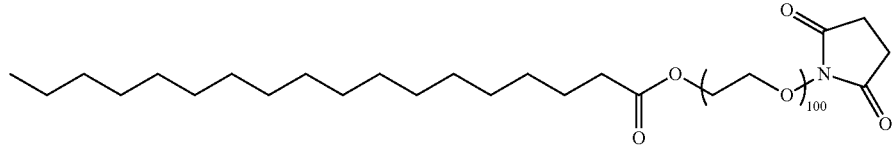

was prepared by following the reaction scheme as follows:

In an anhydrous flask and under argon, Myrj S59 (2.345 g, 0.5 mmol) was dissolved in dry dioxane (15 mL) with heating so as to obtain a clear solution. Then, the reaction medium was brought back to ambient temperature (25° C.), before the addition of disuccinimidyl carbonate (0.77 g; 3 mmol) dissolved in dry acetone (3 mL). The 4-dimethylaminopyridine (0.37 g; 3 mmol), that was previously dissolved in dry acetone (3 mL) was then added slowly and under the effect of stirring to the reaction medium. The reaction was monitored by using TLC ($CH_3Cl/MeOH$) 5/1. After a period of 5 hours under the effect of stirring at ambient temperature, the product was precipitated in cold diethyl ether (100 mL), and the solid thus obtained was centrifuged in order to be isolated, then redissolved in acetone, precipitated again, and this was repeated several times. The expected surfactant having the formula (L) was dried under vacuum, so as to be obtained in the form of a white powder (72% yield).

$^1$H NMR (300 MHz; MeOD): d: 0.87 (t; J=6.5 Hz; 3H; C$\underline{H}_3$—CH$_2$); 1.25 (m; 28H; 14C$\underline{H}_2$); 1.61 (quin; J=7.5 Hz; 2H; C$\underline{H}_2$—CH$_2$—COO); 2.32 (t; J=7.5 Hz; 2H; C$\underline{H}_2$—COO); 2.85 (s, 4H, CH$_2$ NHS); 3.57-3.95 (m; 362H; ×C$\underline{H}_2$(PEG); 4.22 (t; J=5 Hz; 2H; C$\underline{H}_2$—OOC—CH$_2$)

Preparation of an Emulsion 3 Comprising the Surfactant Having the Formula (L) and an Emulsion Comprising a Surfactant Derived from DSPE-PEG (by Way of a Comparison)

The emulsions in which the droplets comprise on the surface the group that may be functionalised N-hydroxysuccinimide (NHS) ester were prepared These emulsions comprise either the surfactant having the formula (L) as prepared here above (molecular weight of about 5000 g mol$^{-1}$), or a surfactant derived from DSPE-PEG-NHS (molecular weight: 3400 g mol$^{-1}$) and they were prepared by following the procedures described in the document WO 2010/018223 with the compositions respectively indicated in the Tables 4 and 5.

by agents of interest having an amino group ($NH_2$). In the example here below, a —$NH_2$ Fluorophore (5-FAM cadaverine) was coupled to the surface of the droplets.

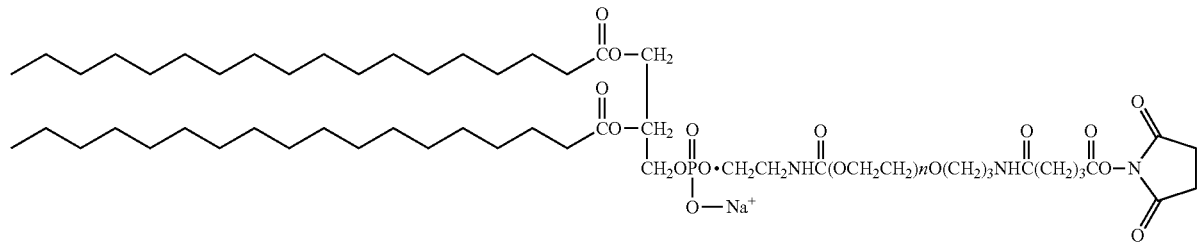

DSPE-PEG-NHS (with n=75) from NOF (molecular weight: 3400 g $mol^{-1}$)

TABLE 4

Composition of the emulsion 3 comprising a surfactant having the formula (L)

| | % of surfactant having the formula (L) by mass/total mass of the emulsion | | | | |
|---|---|---|---|---|---|
| | 4.5% | 8.0% | 12.0% | 15.0% | 30.0% |
| Purified Soybean Oil (mg) | 85 | 85 | 85 | 85 | 85 |
| Suppocire NC (mg) | 255 | 255 | 255 | 255 | 255 |
| Lecithin Lipoid s75 (mg) | 65 | 65 | 65 | 65 | 65 |
| Myrj 52 (mg) | 314.8 | 291.4 | 264.5 | 244.4 | 184.1 |
| surfactant having the formula (L) (mg) | 71.3 | 126.8 | 190.1 | 237.7 | 380.3 |
| PBS (μL) | 1208.9 | 1176.9 | 1140.3 | 1112.9 | 1030.6 |

TABLE 5

Composition of the Comparative Emulsion Comprising DSPE-PEG-NHS

| | % of DSPE-PEG-NHS by mass/total mass of the emulsion | |
|---|---|---|
| | 3.0% | 4.5% |
| Purified Soybean Oil (mg) | 85 | 85 |
| Suppocire NC (mg) | 255 | 255 |
| Lecithin Lipoid s75 (mg) | 65 | 65 |
| Myrj 52 (mg) | 322.4 | 314.8 |
| DSPE-PEG-NHS (mg) | 44.1 | 58.8 |
| PBS (μL) | 771.5 | 778.6 |

The preparation of emulsions comprising the surfactant having the formula (L) was possible for all the mass percentages of surfactant having the formula (L) tested (up to 30% by mass of surfactant/total mass tested). In contrast, the preparation of emulsions comprising DSPE-PEG-NHS was not possible beyond 4.5% by mass of DSPE-PEG-NHS because the medium became too viscous to be formulated.

It is therefore possible to prepare an emulsion with more of the surfactant having the formula (L) than the surfactant DSPE-PEG-NHS. Thus, the droplets of an emulsion prepared with the surfactant having the formula (L) have more NHS functions on the surface.

Grafting of an Agent of Interest on the Surface of the Emulsions Prepared Above

The droplets of the emulsions as prepared here above have on the surface NHS groups that may be functionalised For each of the emulsions, volumes of emulsions were used such that the number of NHS function per liter of emulsion was 4 μmol, that is to say, a volume of emulsion as follows:

TABLE 6

Volume of Emulsion used for the Functionalisation by 5-FAM Cadaverine

| % of surfactant having the formula (L) by mass/total mass of the emulsion | Volume of emulsion used (μL) |
|---|---|
| 4.5 | 864.8 |
| 8 | 488.5 |
| 12 | 324.9 |
| 15 | 260 |

The volume of emulsion indicated in the Table 6 here above was mixed with 3.85 mg of 1-Ethyl-3-(3-dimethylaminopropyl)carbodiimide, EDC (5 eq. that is 20 μmol) and 10.86 mg of sulfo-NHS (50 μmol) for 15 minutes at ambient temperature, protected from light (pH=6). 15 .μL of 5-FAM cadaverine at 0.40 μM, that is 6 μMoles (1.5 eq at pH=7.4) were added for 2 hours at ambient temperature, protected from light (sample).

Blank control samples were prepared by replicating these experiments by mixing the volume of emulsion indicated in the Table 6 here above with 3.85 mg of EDC (5 eq. that is 20 μmol) and 10.86 mg of sulfo-NHS (50 μmol) for 15 minutes at ambient temperature, protected from light (pH=6). (No further addition of 5-FAM cadaverine)

The experiment was also replicated with the emulsion prepared from the surfactant DSPE-PEG-NHS.

The emulsions obtained were dialysed against PBS 1× sterile (membrane Da=12 400) for a period of 16 hours (with change of the dialysis water 2×).

The amount of 5-FAM cadaverine grafted to the surface of the droplets was then assayed by absorbance spectrophotometry (Cary 300, Varian) and confirmed by means of spectrofluorimetry (LS50B, Perkin-Elmer). The possible signal of diffusion of nanoparticles was corrected by subtracting it from the negative blank control samples incubated under the same conditions but without 5-FAM-cadaverine. The grafting yields (ratio between the number of fluorophores grafted to the surface and the number of NHS functions introduced) are summarised in the Table 7.

TABLE 7 yields of grafting of the 5-FAM cadaverine on the functionalised emulsions comprising either a surfactant DSPE-PEG-NHS, or a surfactant having the formula (L)

| Size of Droplets (nm) | Surfactant | % of surfactant by mass/ total mass of the emulsion | Grafting Yield (%) |
|---|---|---|---|
| 50 | DSPE-PEG-NHS | 4.5 | 10 |
| 50 | surfactant having | 4.5 | 10 |
| 50 | the formula (L) | 8 | 57 |
| 50 | | 12 | 51 |
| 50 | | 15 | 58 |

By using the emulsions comprising a surfactant having the formula (L) including more of surface NHS functions (% of surfactant by mass/higher total mass of the emulsion), a better grafting yield was obtained. The number of 5-FAM-cadaverine (fluorophore-agent of interest) grafted in a covalent manner to the surface of the droplets is thus greater when the surfactant having the formula (L) is used.

Comparison of Leakage of Surfactants Having the Formula L where $A_2$ Represents NH or O The emulsions comprising surfactants having the formula (L) where $A_2$ represents NH or O and grafted with fluorescein isothiocyanate (FITC) (Agent of interest) were prepared.

Preparation of a Surfactant Having the Formula (L) Wherein $R_2$ Represents $C_{17}H_{35}$, $A_2$ Represents O, n Represents 100 and φ Represents an Amino Group on which Fluorescein Isothiocyanate, FITC has been Grafted The following reaction scheme was followed:

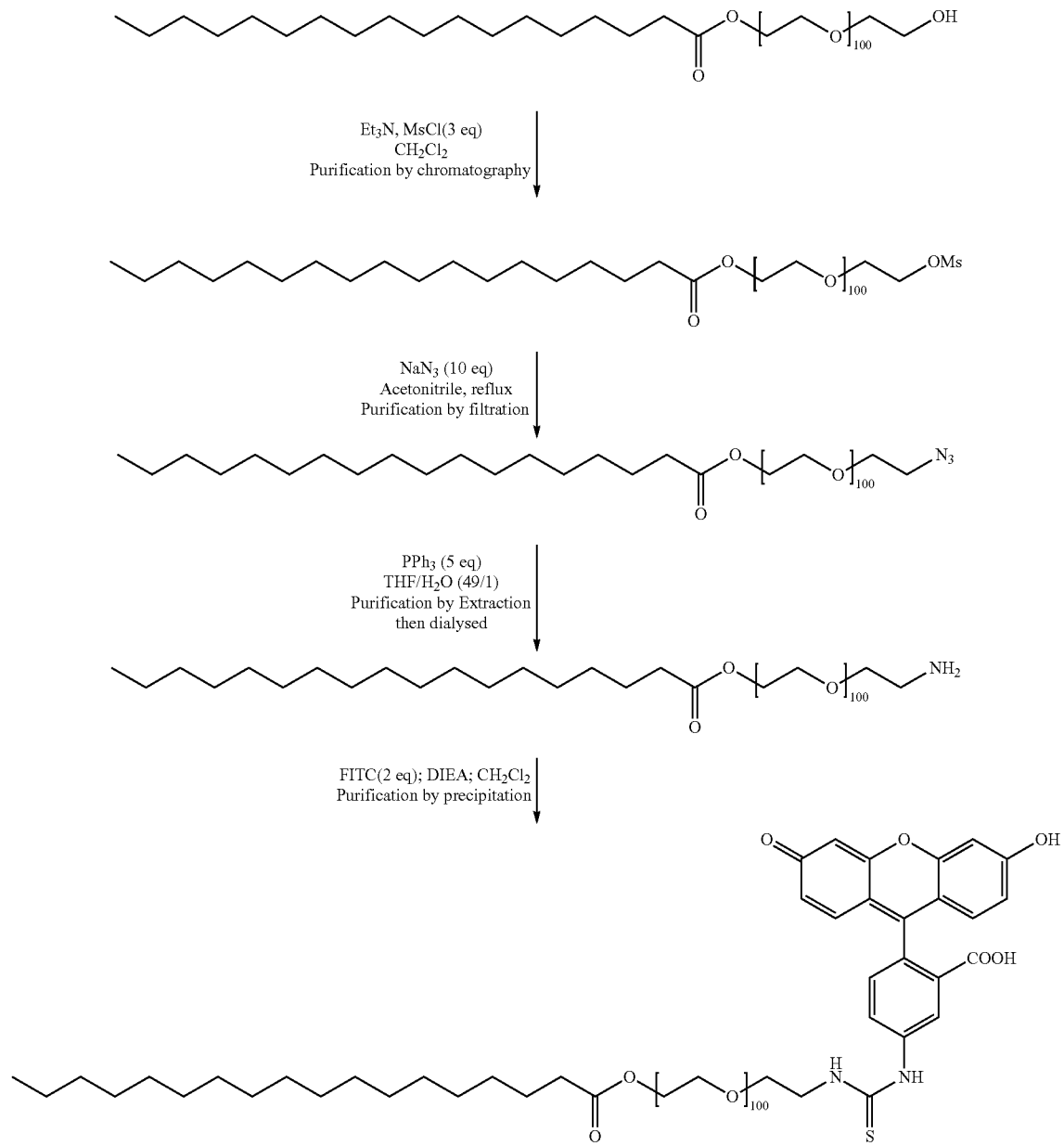

Synthesis of

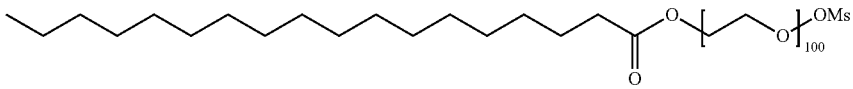

Under argon Myrj S100 anhydrous (10 g; 1.98 mmol) and triethylamine (0.8 mL; 5.94 mmol) was dissolved in dichloromethane stabilised on amylene and anhydrous (50 mL). After 5 minutes under stirring, the temperature was lowered to 0° C. and then mesyl chloride (0.46 mL; 5.94 mmol) was added to the reaction medium. After a period of 24 hours at ambient temperature, the excess amount of mesyl chloride was cold quenched with ethanol. After 5 minutes of stirring, the solvent was evaporated under vacuum. The product was then chromatographed on a silica column with a gradient of dichloromethane/methanol (9.5/0.5 to 9/1) as eluent, in order to obtain a white solid with a yield of 23%.

1H NMR (300 MHz; CDCl3): d: 0.84 (t; J=6.5 Hz; 3H; C$\underline{H_3}$—CH$_2$); 1.21 (m; 28H; 14C$\underline{H_2}$); 1.57 (quin; J=7.5 Hz; 2H; C$\underline{H_2}$—CH$_2$—COO); 2.28 (t; J=7.5 Hz; 2H; C$\underline{H_2}$—COO); 3.04 (s; 3H; C$\underline{H_3}$—S); 3.6-3.8 (m; 360H; × C$\underline{H_2}$(PEG)); 4.18 (t; J=5 Hz; 2H; C$\underline{H_2}$—OOC—CH$_2$); 4.33 (m; 2H; C$\underline{H_2}$—OMs)

Synthesis of

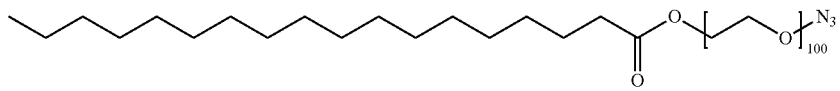

The compound from the previous step (2.33 g, 0.45 mmol) and sodium azide (0.29 g, 4.54 mmol) were caused to be suspended in acetonitrile (23.3 mL). The mixture was brought to 85° C. and maintained for a period of 2 days. The solvent was evaporated, the reaction mixture was dissolved in dichloromethane and the NaN$_3$ in suspension was filtered. The dichloromethane was evaporated under vacuum in order to obtain the desired compound in the form of a white powder (93% yield).

1H NMR (300 MHz; CDCl3): d: 0.88 (t; J=6.5 Hz; 3H; C$\underline{H_3}$—CH$_2$); 1.25 (m; 28H; 14C$\underline{H_2}$); 1.6 (quin; J=7.5 Hz; 2H; C$\underline{H_2}$—CH$_2$—COO); 2.32 (t; J=7.5 Hz; 2H; C$\underline{H_2}$—COO); 3.4 (m; 2H; C$\underline{H_2}$—N$_3$); 3.6-3.8 (m; 360H; ×C$\underline{H_2}$(PEG)); 4.22 (t; J=5 Hz; 2H; C$\underline{H_2}$—OOC—CH$_2$)

Synthesis of

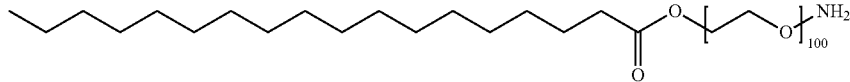

The compound from the previous step (2.15 g, 0.42 mmol) and triphenylphosphine (560 mg, 2.12 mmol) were dissolved in tetrahydrofuran, THF (20 mL). After 10 minutes of stirring, 0.4 mL of water was added to the reaction medium. During the course of the reaction, the appearance of the amine was monitored by TLC (CH$_2$Cl$_2$/MeOH 9/1) with ninhydrin as a developer. After a period of 2 days under stirring, the solvent was evaporated and the product was taken up in hexane and extracted with methanol. The methanol phases were combined and evaporated to dryness. The product was taken up in water, dialysed (pH 6-7) and then lyophilised in order to obtain the expected compound in the form of a white powder (90% yield).

TLC (CH$_2$Cl$_2$/MeOH 9/1): Rf=0.27

1H NMR (300 MHz; CDCl3): d: 0.88 (t; J=6.5 Hz; 3H; C$\underline{H_3}$—CH$_2$); 1.25 (m; 28H; 14C$\underline{H_2}$); 1.6 (quin; J=7.5 Hz; 2H; C$\underline{H_2}$—CH$_2$—COO); 2.32 (t; J=7.5 Hz; 2H; CH$_2$—OOC); 2.88 (t. J=5 Hz; 2H; C$\underline{H_2}$—NH$_2$); 3.53 (t; J=5 Hz; 2H; OC$\underline{H_2}$—CH$_2$—NH$_2$); 3.6-3.8 (m; 360H; ×C$\underline{H_2}$(PEG)); 4.22 (t; J=5 Hz; 2H; C$\underline{H_2}$—OOC—CH$_2$)

Synthesis of

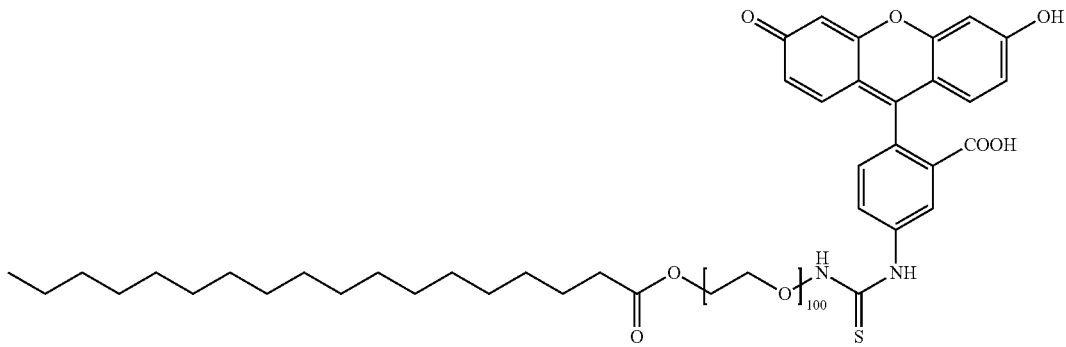

In an anhydrous flask and under argon, the compound from the previous step (100 mg, 0.02 mmol) was dissolved in dichloromethane (2 mL) and dimethylformamide, DMF (0.1 mL). After 3 minutes under stirring, the fluorescein isothiocyanate, FITC (isomer 1 at 90%) (15.4 mg; 0.04 mmol) and diisopropylethylamine, DIEA (7 mL; 0.04 mmol) were added therein. The reaction was monitored by TLC ($CH_2Cl_2$/MeOH/AcOH) 9/1/0.1. After a period of 10 minutes under stirring, the solvent was evaporated under vacuum, the product was precipitated in ether and the solid thus obtained was washed with ethyl acetate. The expected compound was obtained in the form of a yellow powder (76% yield).

TLC ($CH_2Cl_2$/MeOH 9/1): Rf=0.37

$^1$H NMR (300 MHz; MeOD): d: 0.91 (t; J=6.5 Hz; 3H; C$\underline{H}_3$—CH$_2$); 1.30 (m; 28H; 14C$\underline{H}_2$); 1.62 (quin; J=7.5 Hz; 2H; C$\underline{H}_2$—CH$_2$—COO); 2.35 (t; J=7.5 Hz; 2H; C$\underline{H}_2$—COO); 3.55-3.9 (m; 362H; ×C$\underline{H}_2$(PEG); C$\underline{H}_2$—NHFITC); 4.22 (t; J=5 Hz; 2H; C$\underline{H}_2$—OOC—CH$_2$); 6.6 (dd; J=2 Hz; J=8.5 Hz; 2H; 2CH$_{aromatic}$); 6.7 (d; J=2 Hz; 2H; 2CH$_{aromatic}$); 6.82 (d; J=8.5 Hz; 2H; 2CH$_{aromatic}$); 7.2 (d; J=8 Hz. 1H; $_{aromatic}$ CH); 7.86 (d; J=8 Hz. 1H; $_{aromatic}$ C$\underline{H}$); 8.21 (s; 1H; $_{aromatic}$ C$\underline{H}$)

Preparation of a Surfactant Having the Formula (L) Wherein $R_2$ Represents $C_{17}H_{35}$, $A_2$ Represents NH, n Represents 100 and φ Represents an Amino Group on which Fluorescein Isothiocyanate, FITC has been Grafted The synthesis was carried out using the compound (C) from the Example 1 having the formula according to the following reaction scheme:

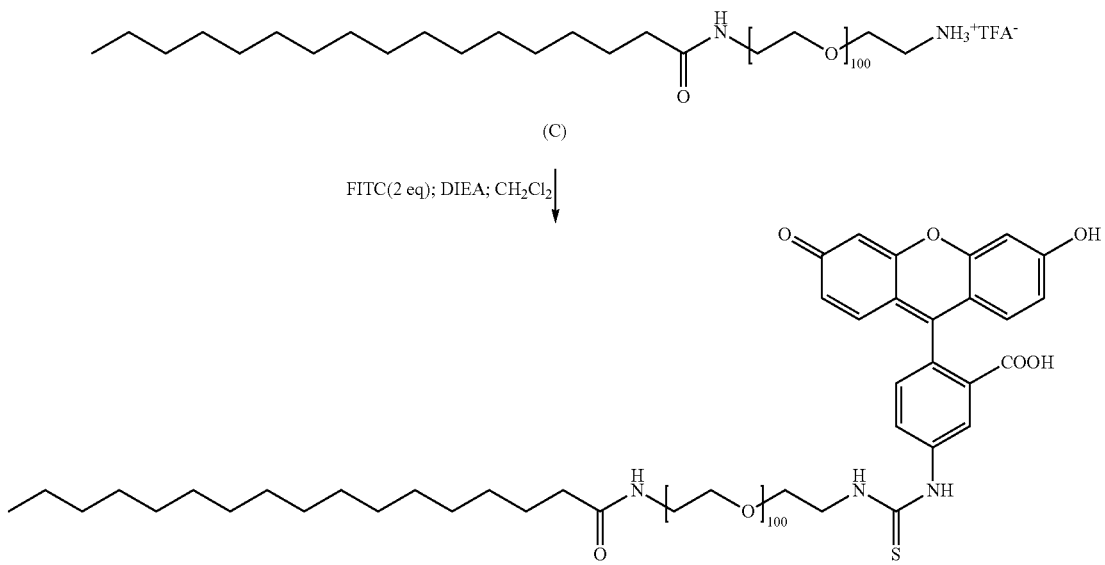

In an anhydrous flask and under argon, the compound (C) (250 mg; 0.05 mmol) was dissolved in dichloromethane (5 mL) and dimethylformamide, DMF (0.2 mL). After 3 minutes under stirring, the fluorescein isothiocyanate, FITC (isomer 1 to 90%) (30 mg; 0.075 mmol) and diisopropylethylamine, DIEA (25 mL, 0.15 mmol) were added therein. The reaction was monitored by TLC ($CH_2Cl_2$/MeOH/AcOH) 9/1/0.1. After a period of 10 minutes under stirring, the solvent was evaporated under vacuum, the product was precipitated in ether and the solid thus obtained was washed with ethyl acetate. The solid was taken up in water at pH 7. After dialysis (pore 1000 Da), the solution of the expected compound was lyophilised and the expected compound (200 mg) was obtained in the form of an orange powder (yield 76%).

TLC (CH$_2$Cl$_2$/MeOH 9/1): Rf=0.37

$^1$H NMR (300 MHz; MeOD): d: 0.91 (t; J=6.5 Hz; 3H; CH$_3$—CH$_2$); 1.31 (m; 28H; 14CH$_2$); 1.62 (quin; J=7.5 Hz; 2H; CH$_2$—CH$_2$—CONH); 2.2 (t; J=7.5 Hz; 2H; CH$_2$—CONH); 3.41 (m; 2H; CH$_2$—NHCO); 3.55-3.9 (m; 364H; xCH$_2$(PEG); CH$_2$—NH-FITC); 6.56 (m; J=9 Hz; J=2.5 Hz; 4H; 4CH$_{aromatic}$); 7.15 (d; J=9 Hz; 2H; 2CH$_{aromatic}$); 7.2 (d; J=8.5 Hz; 1H; $_{aromatic}$CH); 7.76 (dd; J=8.5 Hz; J=2.5 Hz; 1H; $_{aroma}$CH); 7.87 (d; J=2.5 Hz; 1H; $_{aromatic}$CH)

Preparation of Emulsions or 3 Comprising Either the Surfactant Having the Formula (L) Wherein A$_2$ Represents NH or the Surfactant Having the Formula (L) Wherein A$_2$ Represents O The emulsions 3 functionalised by the group FITC comprising the components indicated in the Table 8 here below were prepared by following the procedures described in the document WO 2010/018223.

TABLE 8

Composition of Emulsion 3 A$_2$ = NH and Emulsion 3 A$_2$ = O

|  | Emulsion 3 A$_2$ = NH | Emulsion 3 A$_2$ = O |
|---|---|---|
| Purified Soybean Oil (mg) | 85 | 85 |
| Suppocire NC (mg) | 255 | 255 |
| Lecithin Lipoid s75 (mg) | 65 | 65 |
| Myrj S40 (mg) | 328 | 328 |
| PBS (uL) | 771.5 | 778.6 |
| C$_{17}$H$_{35}$—CO—NH—[(CH$_2$)$_2$—O]$_{100}$—(CH$_2$)$_2$—NH-FITC (mg) | 17 | — |
| C$_{17}$H$_{35}$—CO—O—[(CH$_2$)$_2$—O]$_{100}$—(CH$_2$)$_2$—NH-FITC (mg) | — | 17 |

Emulsions comprising droplets of diameter 50 nm were obtained in each case.

Leakage of the Surfactants Out of the Droplets of the Emulsions 3 Formed

Figure 6:
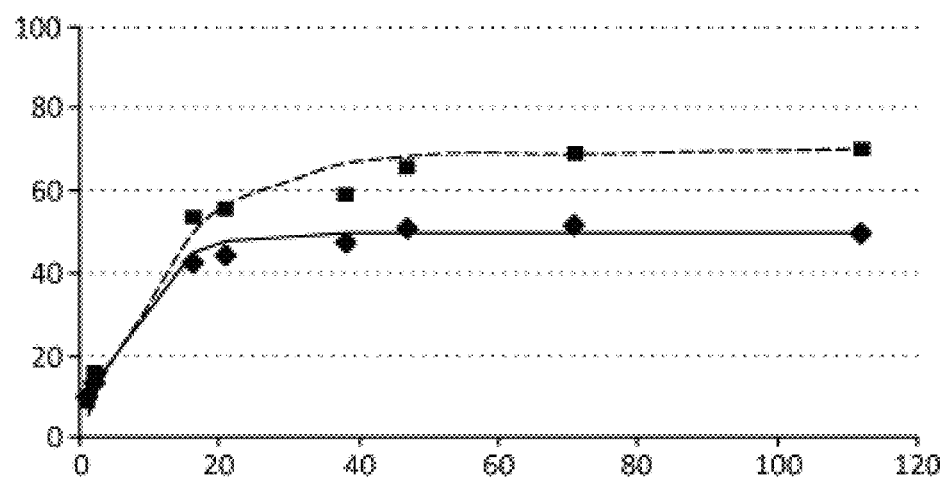
FIG. 6 shows the percentage loss of surfactant $C_{17}H_{35}$—CO—NH—$[(CH_2)_2$—$O]_{100}$—$(CH_2)_2$—NH-FITC outside of the droplets of the emulsion 3 $A_2$=NH (diamonds, solid line) or of surfactant $C_{17}H_{35}$—CO—O—$[(CH_2)_2$—$O]_{100}$—$(CH_2)_2$—NH-FITC outside of the droplets of the emulsion 3 $A_2$=O (squares, dotted line) as a function of time in hours.

Analysis was carried out of the desorption of the surfactants during a dialysis period of 48 hours. The surfactants were quantified in the dialysate by measuring the absorbance at 490 nm (the surfactants in the dialysate correspond to those that have leaked out of droplets). The conditions of dialysis were as follows: 400 mL of emulsion 3 at 20% (w/w) in a "Quick dialyser", then set to be dialysed in 400 mL of PBS. The dialysis lasted for a period of 120 hours. The leakage of surfactant (C$_{17}$H$_{35}$—CO—NH—[(CH$_2$)$_2$—O]$_{100}$—(CH$_2$)$_2$—NH-FITC or C$_{17}$H$_{35}$—CO—O—[(CH$_2$)$_2$—O]$_{100}$—(CH$_2$)$_2$—NH-FITC) was monitored by regularly taking a 300 ml sample of the dialysate. The results have been illustrated in the FIG. 6.

Thus, after a 48 hour period of dialysis, it was found that 50% of the surfactant C$_{17}$H$_{35}$—CO—NH—[(CH$_2$)$_2$—O]$_{100}$—(CH$_2$)$_2$—NH-FITC had leaked out of the droplets of the emulsion 3 A$_2$=NH, whereas 70% of the surfactant C$_{17}$H$_{35}$CO—O—[(CH$_2$)$_2$O]$_{100}$—(CH$_2$)$_2$NH-FITC had leaked out of the droplets of the emulsion 3 A$_2$=O. The surfactant with A$_2$=NH thus desorbs less of the droplets than the surfactant with A$_2$=O.

Example 6

An Emulsion Comprising a Material Including a Surfactant Having the Formula (I) Comprising a G Group Including an Irreversible Cleavable Function In this example use is made in the implementation of a homo-bifunctional compound to form the surfactant having the formula (I) that enables the generation of the covalent bonds between the droplets.

The droplets bearing at their surface a reactive primary amine function are brought to be reacted with a dialdehyde compound, glutaraldehyde, so as to form a Schiff base (imine), which is then reduced (reductive amination). The secondary amine formed then forms an irreversible covalent bond between the droplets.

More specifically, the reaction that is brought into play is of the type illustrated in the diagram here below:

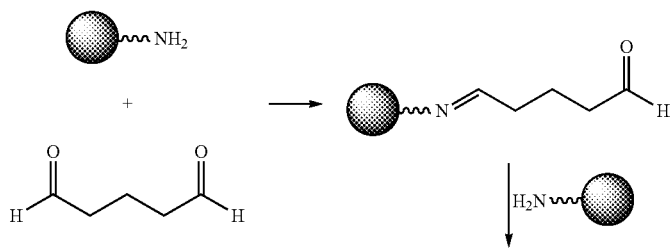

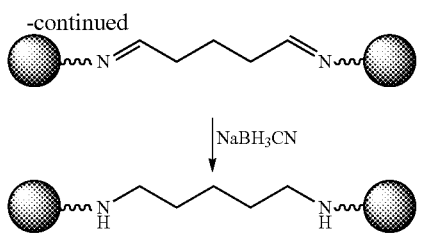

An emulsion comprising droplets bearing at their surface a terminal primary amine group was prepared by following the operational procedure as in Example 1, with the components for the oily phase and aqueous phase, as detailed in the Table 9 here below. After purification, the emulsion LNP-NH2 obtained comprised 11% w/w of the dispersed phase.

To 1 mL of the emulsion thus obtained was added 0.28 .μL of 50% glutaraldehyde in water and these were allowed to react at ambient temperature for a period of 1 hour. Thereafter, 1 ml of emulsion was once again added therein and was then allowed to react for a period of 12 hours before adding 282 μL of sodium cyanoborohydride in 10 mM solution (NaCNBH$_3$)

The formation in the reaction mixture of aggregates visible to the naked eye was observed. These aggregates may be isolated by gently pipetting from the tube the reaction mixture containing the droplets that were unreacted. A gel is obtained on the walls of the tube.

When the gel formed was brought to be contacted again with fresh phosphate buffer (Phosphate Buffered Saline PBS 1×), there was no dissolution due to the dilution observed, which serves as evidence demonstrating the existence of a chemical gel. If this gel is subjected to intense agitation, for example by means of vortexing, it is observed that the gel disintegrates into fine aggregates only to be reformed, after a period of rest of 1 hour and:30 min, on the surface of the buffer solution.

TABLE 9

Composition of the emulsion LNP-NH2
Mass (mg)

| Lipid Phase | | | Aqueous Phase | | |
|---|---|---|---|---|---|
| Purified Soybean Oil | Wax Suppocire NC | Lecithin Lipoid s75 | Myrj ® S40 | SA-PEG(100)-NH$_2$ (Compound C as in Example 1) | PBS 1X |
| 68 | 272 | 65 | 312 | 33 | 771.5 |

Example 7

Formation of a Gel from an Emulsion LNP-NH$_2$ LNP-SH and a Sulfo-SMCC Cross-Linker In this example, use is made in the implementation of a cross-linker (Succinimidyl 4-(N-maleimidomethyl)cyclohexane-1-carboxylate, sulfo-SMCC) in order to generate a covalent bond between the droplets bearing the groups —NH$_2$ (LNP-NH2) on their surface and others bearing the groups —SH on their surface (LNP-SH) and to form a gel.

The reactions that are brought into play are illustrated in the diagram here below.

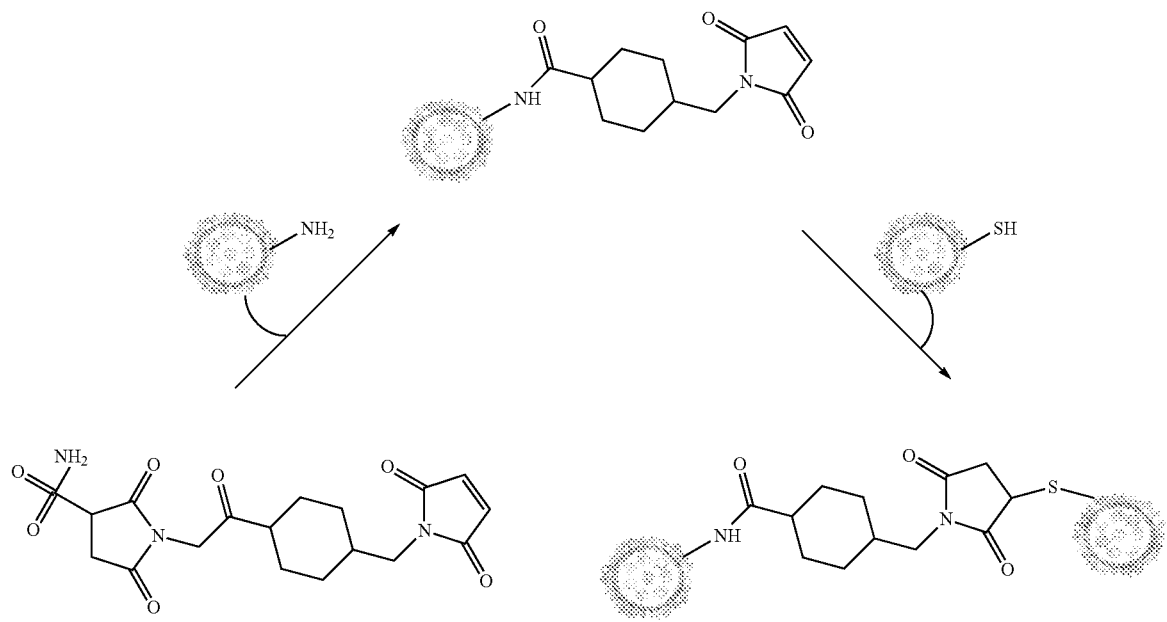

A. Preparation of an Emulsion of LNP-SH

The oily phase was prepared as in Example 1, by using the ingredients and proportions indicated in the Table 10 here below. A small amount of dichloromethane was added to improve the solubility in the oily phase, it was evaporated thereafter. A fluorophore (DiD) was added to the premix (80 ul, 10 mM in ethanol) in order to enable improved subsequent visual observation of the droplets.

TABLE 10A

Composition of the Emulsion LNP-SH
Mass (mg)

| Lipid Phase | | | Aqueous Phase | | |
|---|---|---|---|---|---|
| Purified Soybean Oil | Wax Suppocire NC | Lecithin Lipoid s75 | Myrj ® S40 | $SA_{CONH}PEG100$-SSpyr | PBS 1X |
| 68 | 272 | 65 | 276 | 69 | 2500 |

The aqueous phase was prepared as in Example 1, by using the ingredients and proportions set forth in the Table 10A here below. The surfactant $SA_{CONH}PEG100$-S-S-Pyr (surfactant LII in the Example 1) was added in an amount of up to 20% by mass relative to the total mass of surfactant LII. For the dissolution of surfactants, the mixture was heated to 55° C.

The emulsion was prepared by adding the aqueous phase obtained in the flask containing the oily phase (still hot at 45° C.), and then sonicating the mixture to 50° C. under the conditions indicated in the Table 2 above, but with a power Pmax of 30%.

Thereafter, 46 mg of DTT (dithiothreitol, that is 20 molar eq) was added to the suspension of LNP- SS-PYR and then the particle dispersion was stirred for a period of two hours on a moving stir plate so as to reduce the S—S-PYR functions in thiol form (—SH).

Finally, the LNP-SH were dialysed 2 times against PBS 1× (MW Cut off 12000-14000 Da; 500 mL; 24 hours). After dialysis, the LNP-SH droplets were filtered on filters of 0.2 μm.

B. Preparation of an Emulsion LNP-NH$_2$

The oily phase was prepared as previously described here above for the emulsion LNP-SH, using the same ingredients and proportions.

The aqueous phase was prepared as in Example 1, by using the ingredients and proportions set forth in the Table 10B here below. The surfactant $SA_{CONH}PEG100$-NH$_3^+$ TFA$^-$ (surfactant C in the Example 1) was added in an amount of up to 20% by mass relative to the total mass of surfactant C. For the dissolution of surfactants, the mixture was heated to 55° C.

TABLE 10B

Composition of the Emulsion LNP-NH2
Mass (mg)

| Lipid Phase | | | Aqueous Phase | | |
|---|---|---|---|---|---|
| Purified Soybean Oil | Wax Suppocire NC | Lecithin Lipoid s75 | Myrj ® S40 | $SA_{CONH}PEG100$-NH3$^+$TFA | PBS 1X |
| 85 | 272 | 65 | 276 | 69 | 2500 |

The emulsion was prepared by adding the aqueous phase obtained in the flask containing the oily phase (still hot at 45° C.), and then sonicating the mixture to 50° C. under the conditions indicated in the previous example.

The emulsion LNP-NH$_2$ thus obtained was dialysed 2 times against PBS 1× (MW Cut off 12000-14000 Da; 500 mL; 24 hours). After dialysis, the LNP-NH2 droplets were filtered on filters of 0.2 microns.

A solution of Sulfo-SMCC (Succinimidyl 4-(N-maleimidomethyl)cyclohexane-1-carboxylate, Pierce, 0.87 mL, 4.58 mM, 4 μmol) was added to the dispersion of LNP-NH$_3^+$TFA$^-$ (0.1 mL, 0.4 μmol of amine functions). The mixture was stirred for a period of 3 hours on a moving stir plate. Then, purification by size exclusion column (Disposable PD-10, GE Healthcare) was carried out in order to eliminate the excess sulfo-SMCC. After purification by column, the fractions containing the droplets were collected.

C. Preparation of a Gel from LNP-SH et LNP-NH$_2$

In order to prepare the gel, the emulsion LNP-NH$_2$ obtained above was added to the emulsion LNP-SH (0.1 mL, 0.4 μmol of thiol functions). After reaction over a period of 2 hours with stirring, it was noted that there was formation of aggregates of gel that are insoluble water. groups

Example 8

Formation of Gel from LNP-SS-Pyr and Crosslinker SH-PEG-SH

An emulsion was prepared containing the surfactant $SA_{CONH}PEG_{100}$-SPDP (surfactant LII in the Example 1) with the composition indicated in the Table 11 here below, according to the protocol indicated in the previous example.

The emulsion obtained was purified by dialysis (molecular weight cut offs MWCO 12-14 kDa) against PBS and diluted in a manner so as to obtain a mass fraction of droplets of 20%.

TABLE 11

Composition of the Emulsion LNP-SPDP
Mass (mg)

| Lipid Phase | | | Aqueous Phase | | |
|---|---|---|---|---|---|
| Purified Soybean Oil | Wax Suppocire NC | Lecithin Lipoid s75 | Myrj ® S40 | $SA_{CONH}PEG_{100}$-SPDP (Compound LII as in Example 1) | PBS 1X |
| 150 | 450 | 45 | 172 | 43 | 1140 |

Figure 7:
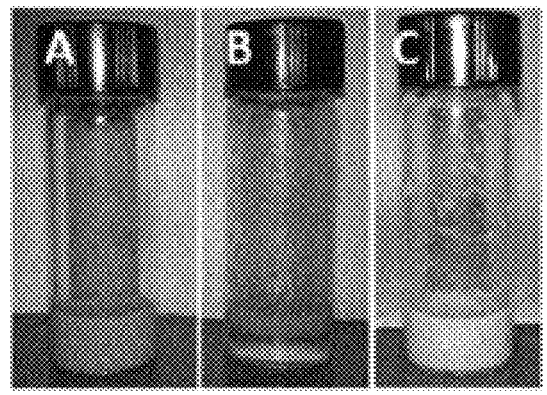
FIG. 7 shows photographs of the materials described in the Example 7: A) the emulsion of droplets of LNP-SPDP [lipid based nanoparticles—N-succinimidyl-3(2-pyridyldithio)propionate]; B) the gel formed after addition of PEG dithiol [poly(ethylene glycol) dithiol]; C) suspension of droplets of LNP-SH obtained after addition of DTT (Dithiothreitol).

A quantity of 500 .μL of this emulsion (100 mg of dispersed droplets) was brought to be reacted with 0.9 mg of poly(ethylene glycol) dithiol (average molecular weight 1000 Da) at ambient temperature with a thiol/SPDP ratio of 1:1 under moderate stirring. A gel began to form within a few minutes after the mixing of the reactants. The gel formed was destroyed by addition of an excess amount of DTT (dithiothreitol) in order to provide the droplets dispersed in the aqueous buffer. The photographs in FIG. 7 illustrate the changes in appearance of the initial LNP-SPDP formulation (FIG. 7A) after addition of PEG dithio (FIG. 7B) and after addition of DTT (FIG. 7C).

The study of the size of particles in the gel and then after destruction provides evidence demonstrating that the process did not alter the morphology of the droplets (see Table 12 here below).

TABLE 12

| Physical and Chemical Properties | | |
|---|---|---|
| | Hydrodynamic Diameter (nm) | Pdl |
| LNP-SPDP (before gelling) | 128 ± 2 | 0.114 ± 0.001 |
| LNP-SH (after gelling) | 135 ± 2 | 0.097 ± 0.013 |

The principle of the formation and destruction of the gel is shown schematically in the schematic diagrams A and B here below.

Schematic Diagram A: Formation of the Gel

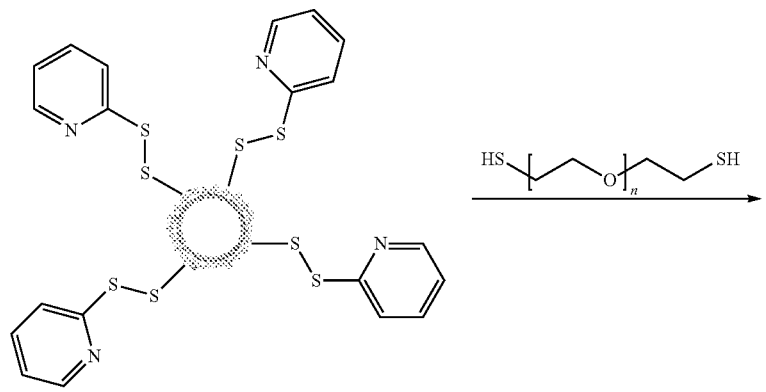

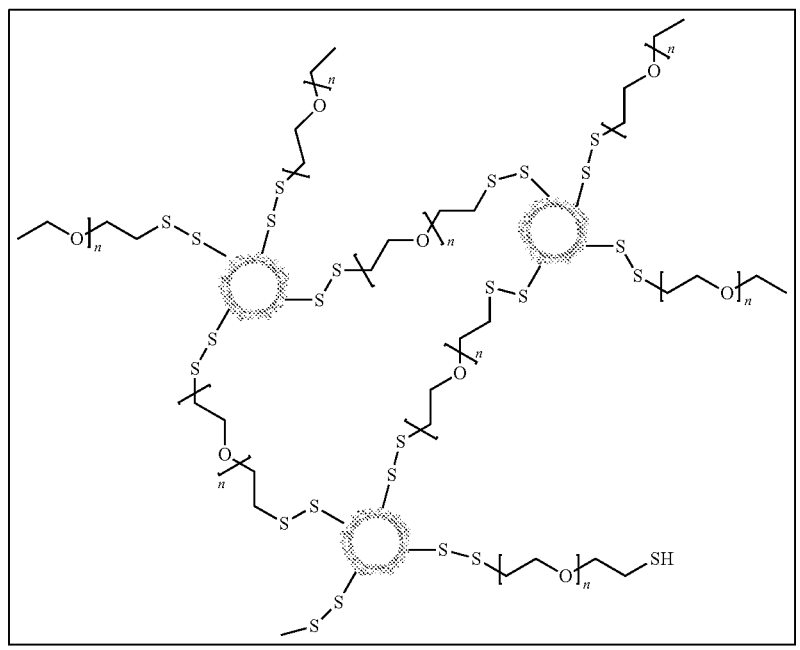

Schematic Diagram B: Destruction of the Gel

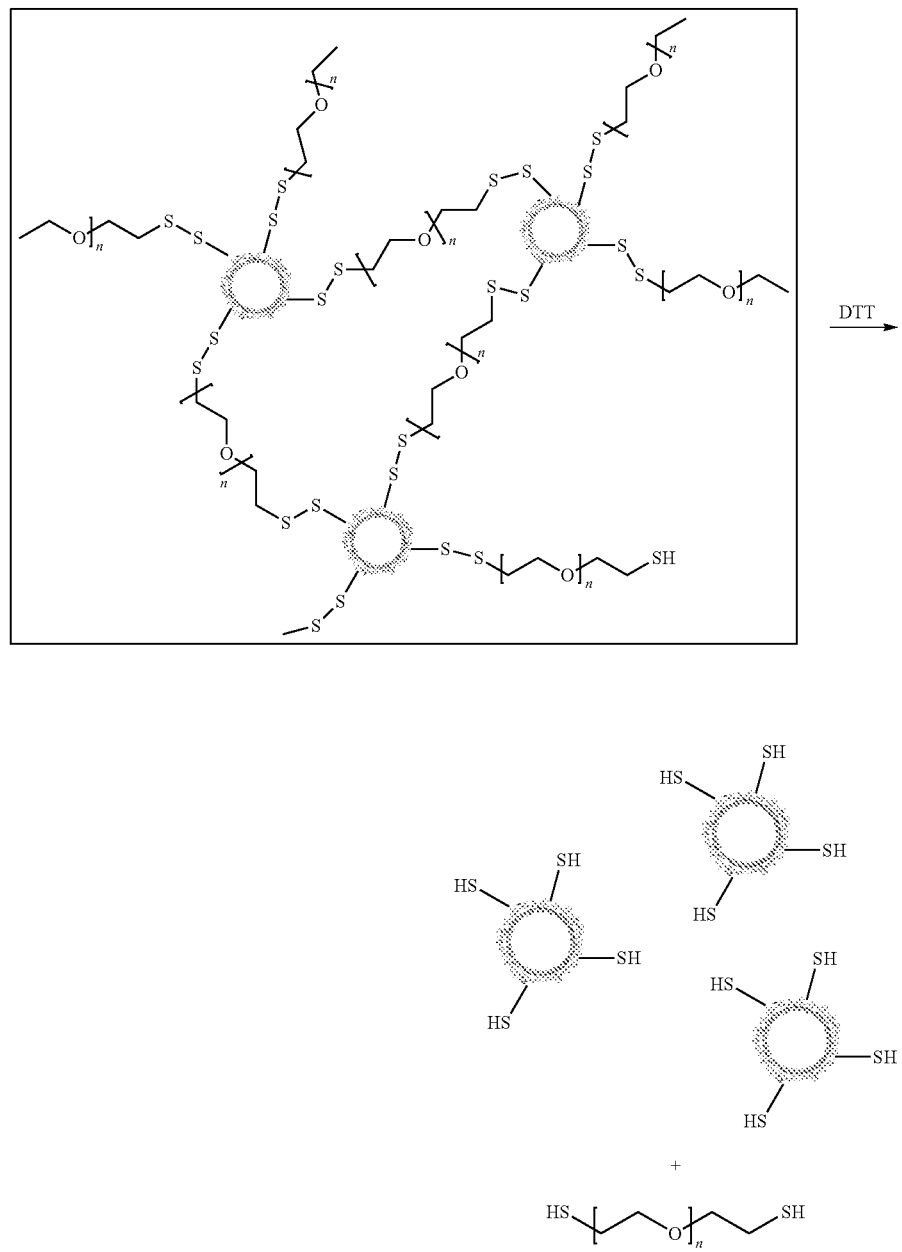

Example 9

Formation of Gels by Irradiation

A. Preparation of an Emulsion of LNP-SH

The oily phase was prepared as in Example 1, by using the ingredients and proportions indicated in the Table 12 here below. A small amount of dichloromethane was added to improve the solubility in the oily phase, it was evaporated thereafter. A fluorophore (DiD) was added to the premix (80 ul, 10 mM in ethanol) in order to enable improved subsequent visual observation of the particles.

The aqueous phase was prepared as in Example 1, by using the ingredients and proportions set forth in the Table 12 here below. The surfactant $SA_{CONH}PEG100\text{-}S\text{—}S\text{-}Pyr$ (surfactant LII in the Example 1) was added in an amount of up to 20% by mass relative to the total mass of surfactant LII. For the dissolution of surfactants, the mixture was heated to 55° C.

The emulsion was prepared by adding the aqueous phase obtained in the flask containing the oily phase (still hot at 45° C.), and then sonicating the mixture to 50° C. under the conditions indicated in the Table 2 above, but with a power Pmax of 30%.

Finally, the LNP-SH were dialysed 2 times against PBS 1× (MW Cut off 12000-14000 Da; 500 mL; 24 hours). After dialysis, the LNP-SH droplets were filtered on filters of 0.2 µm.

TABLE 13

Composition of the Emulsion LNP-SH Mass (mg)

| Lipid Phase | | | Aqueous Phase | | |
|---|---|---|---|---|---|
| Purified Soybean Oil | Wax Suppocire NC | Lecithin Lipid s75 | Myrj ® S40 | $SA_{CONH}PEG_{100}$-SSPyr (Compound LII as in Example 1) | PBS 1X |
| 68 | 272 | 65 | 276 | 69 | 2500 |

B. Preparation of a Gel Under the Action of Light

From the emulsion of LNP-SH obtained here above (weight percentage 23%) 1 mL thereof was introduced into a bottle. Then, the sample was irradiated at 365 nm with a power of 15 mW (OSRAM, HBO 750MA lamp).

Figure 8:
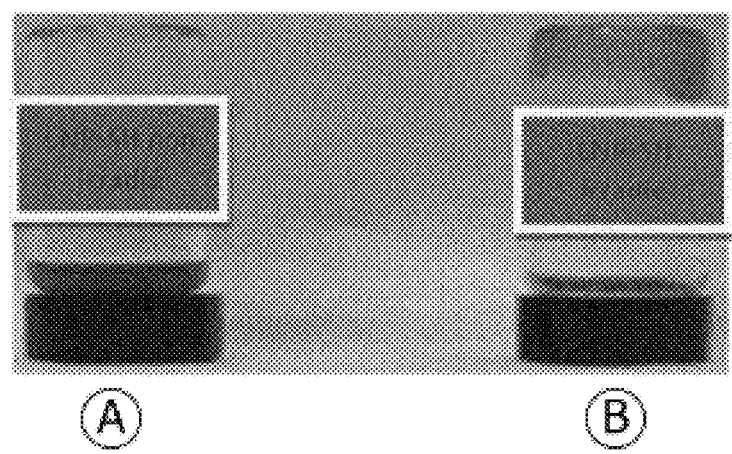
FIG. 8 shows photographs of the materials described in the Example 9 before and after irradiation.

After irradiation period of 1 hour 30 min, it was noted that there was formation of an insoluble chemical gel in the buffer PBS 1× (FIG. 8).

The mechanism of gelation is attributed to the irradiation of the thiol functions at the surface of the droplets, leading to the formation of the radicals —S° on the surface of the LNP, which are capable of leading to the formation of disulphide bonds binding the droplets to one another.

In order to ascertain whether this gelation is due to the presence of the thiol functions on the surface of the lipid droplets, the example was repeated but by replacing the LNP-SH droplets with standard droplets (LNP with terminal —OH functions and not—SSPyr functions). After irradiation period of 1 hour 30 min, it was noted that there was neither any formation of gel nor any change in viscosity.

Furthermore, it was noted that the gel is destroyed when the disulfide bonds are reduced. Indeed, when the photo-formed LNP-S-S-LNP gels were brought to be reacted with the DTT (dithiothreitol, 10 equivalents relative to the number of SH functions), it was noted that the gel returns to a liquid state after two minutes of agitation.

C. Rheological Measurements

In order to study the evolution of the formation of the chemical gel during the irradiation time period, use was made of an oscillating rheometer (AR2000 EX, TA Instruments) enabling the measuring of the modulus of viscosity and modulus of elasticity of the sample, at an oscillation frequency of 1 Hz, during irradiation thereof (360 nm, power of 60 mW/cm$^2$), by depositing 300 µL of LNP-SH emulsion on the Quartz surface above the UV lamp.

During the irradiation time period, an increase was observed both in the modulus of viscosity (G ") and the modulus of elasticity (G'), this being indicative of the gelation. After 80 minutes of irradiation, it was noted that G' has become greater than G", and delta, defined as the tangent (delta)=G'/G", has become less than 45° C., which indicates the transforming of a viscoelastic liquid into a viscoelastic solid.

The same experiment performed with the emulsion of LNP droplets bearing terminal hydroxyl functions (LNP-myrj s100) makes it possible to verify that no changes in rheological properties have occurred during the irradiation process.

m

Example 10

Formation of Gels from SA-PEG-ONHPOC

A. Synthesis of the Surfactant $SA_{CONH}PEG100NHCO$—ONH—POC

This is a polyethylene glycol type surfactant (100 units) bound at one end to a fatty chain (C18) via an amide function and at the other end to another amide function bound to the oxyamine function protected by a protecting group NPPOC (2-(2-nitrophenyl)propyloxycarbonyl).

Its structure (product 3) and its synthesis process diagram are detailed here below.

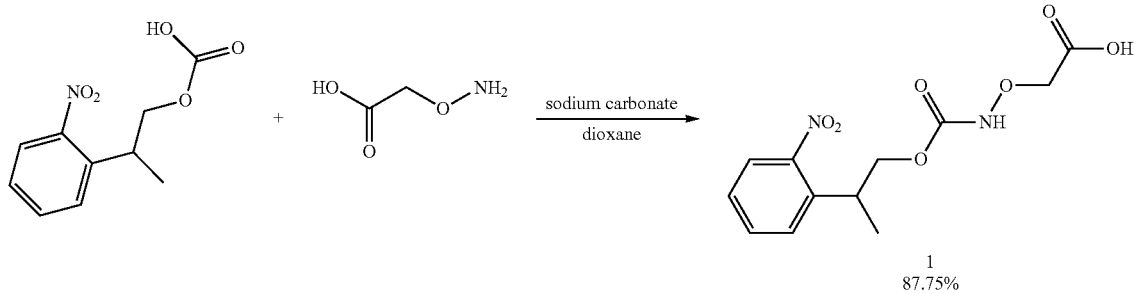

1
87.75%

Dicyclohexylcarbodiimide (DCC), Dichloromethane

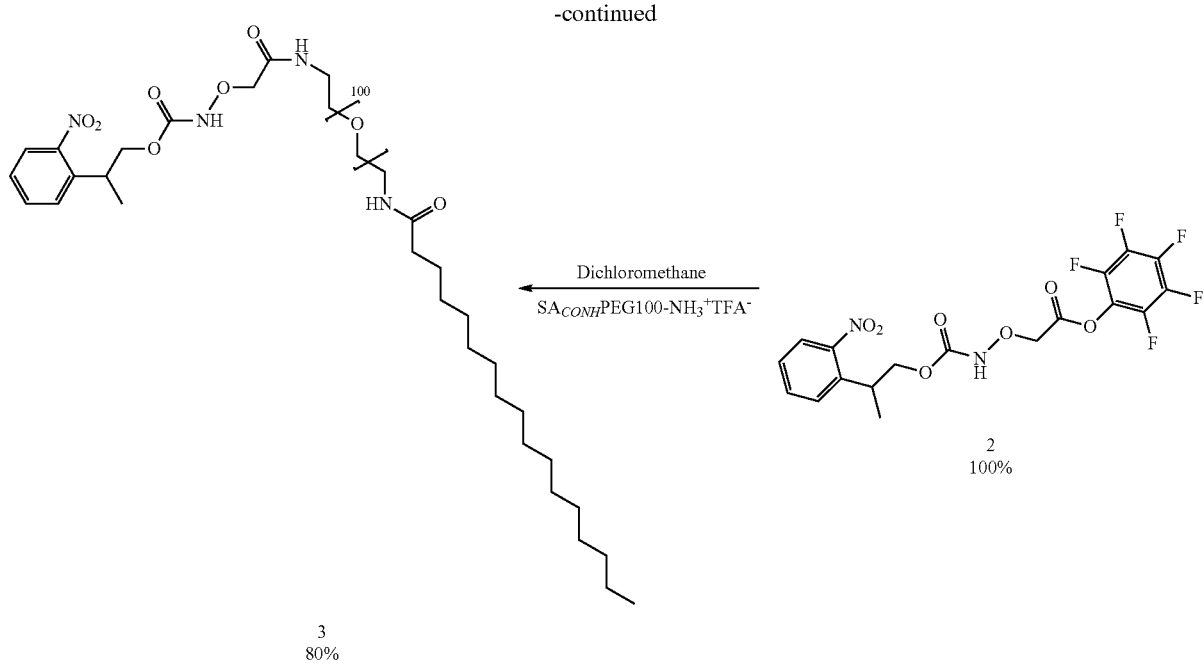

3
80%

Synthesis of the Product 1

Carboxymethoxylamine hydrochloride (1 g, 4.57 mmol) was dissolved in an aqueous solution of sodium carbonate 10% (25 mL). The solution was cooled to 0° C., and a solution of 2-(2-Nitrophenyl)propyl chloroformate (NPPOC—Cl) (2.20 g, 9.1 mmol) was added, drop by drop, into the dioxane (20 mL). The stirring was maintained for a period of 3 hours at ambient temperature. The reaction medium was then evaporated to dryness. To the residue obtained, water (250 mL) was added and the aqueous phase was then washed with diethyl ether (200 mL). The aqueous phase was acidified with an aqueous 1N hydrochloric acid solution to pH 3 and extracted with dichloromethane (3×250 mL). Finally, the organic phases were combined and dried over anhydrous sodium sulfate, and evaporated.

The crude product was purified by means of chromatography on silica gel (dichloromethane then dichloromethane/methanol 97/3, v/v). The product 1 was obtained in the form of a white powder (1.17 g, 3.9 mmol, 87.75%).

$^1$H-NMR (200 MHz, CDCl$_3$): δ ppm 1.34 (3H, d, C$\underline{H}_3$); 3.5 (1H, m, C$\underline{H}$); 3.76 (2H, d, C$\underline{H}_2$O); 4.37 (s, 2H, COCH$_2$O); 7.3-7.6 (4$\underline{H}_4$, m); 8.8 (1H, s, COO$\underline{H}$).

Synthesis of the Product 2

The product 1 (1.17 g, 3.9 mmol) was dissolved in dichloromethane (5 mL) and then pentafluorophenol (906.5 mg, 4.63 mmol) was added, followed by the adding drop by drop of a solution of dicyclohexylcarbodiimide DCC (877.26 mg, 4.63 mmol) into the dichloromethane. The mixture was stirred for a period of 4 hours and then filtered. After evaporation, the product 2 was obtained in the form of a yellow oil (1.8 g, 4.63 mmol, 100%).

$^1$H-NMR (200 MHz, CDCl$_3$): δ ppm 1.34 (3H, d, C$\underline{H}_3$); 3.5 (1H, m, C$\underline{H}$); 3.76 (2H, d, C$\underline{H}_2$O); 4.37 (s, 2H, COCH$_2$O); 7.3-7.6 (4$_{aromaticH}$, m).

Synthesis of the Product 3

Under argon, the SA$_{CONH}$PEG100-NH$_3$$^+$TFA$^-$ (surfactant C in the Example 1, 519.14 mg; 0.1 mmol) and the diisopropylethylamine, DIEA (25 .µL, 0.2 mmol) were dissolved in dichloromethane (10 mL). After 5 minutes of stirring, the product 2 (50.54 mg, 0.13 mmol) was added to the reaction medium. After a reaction period of 2 hours, the solvent was evaporated. The crude product was purified by dialysis in distilled water (MW Cut off 1000 Da; 2 L; 48 hours). Finally, the product 3 was lyophilised in order to bring about the production of a white powder (428.53 mg, 0.08 mmol, 80%).

$^1$H-NMR (200 MHz, CDCl$_3$): δ ppm 0.88 (3H, t, CH$_3$); 1.25 (28H, m, 14 CH2); 1.34 (3H, d, C$\underline{H}_3$); 1.89 (2H, m, CH$_2$—CH$_2$—CONH); 2.17 (2H, t, CH2-CONH); 3.34 (2H, m, CH2-NH$_3$$^+$); 3.4 (1H, m, C$\underline{H}$); 3.5-3.70 (400H, m, CH$_2$ PEG); 3.76 (2H, d, C$\underline{H}_2$O); 4.37 (s, 2H, COC$\underline{H}_2$O); 617 (1H, s, NH); 7.3-7.6 (4$_{AromaticH}$, m).

B. Preparation of the Emulsion of LNP-ONH-POC

The oily phase was prepared as in Example 1, by using the ingredients and proportions indicated in the Table 14 here below. A small amount of dichloromethane was added to improve the solubility in the oily phase, it was evaporated thereafter. A fluorophore (DiD) was added to the premix (80 ul, 10 mM in ethanol) in order to enable improved subsequent visual observation of the particles.

The aqueous phase was prepared as in Example 1, by using the ingredients and proportions set forth in the Table 12 here below. The surfactant SA$_{CONH}$PEG100NHCO—ONH—POC was added in an amount of up to 20% by mass relative to the total mass of PEGylated surfactant. For the dissolution of surfactants, the mixture was heated to 55° C.

The emulsion was prepared by adding the aqueous phase obtained in the flask containing the oily phase (still hot at 45° C.), and then sonicating the mixture to 50° C. under the conditions indicated in the Table 2 above, but with a power Pmax of 30%.

Finally, the droplets were dialysed 2 times against PBS 1× (MW Cut off 12000-14000 Da; 500 mL; 24 hours). After dialysis, the droplets were filtered on filters of 0.2 µm.

TABLE 14

Composition of the emulsion with NPPOC group surfactant
Mass (mg)

| Lipid Phase | | | Aqueous Phase | | |
|---|---|---|---|---|---|
| Purified Soybean Oil | Wax Suppocire NC | Lecithin Lipoid s75 | Myrj ® S40 | $SA_{CONH}PEG_{100}$-NCOONH-POC | PBS 1X |
| 68 | 272 | 65 | 275 | 70 | 2500 |

C. Characterisation

The size and charge of the LNP- ONHPOC were measured by DLS (quasi-elastic light scattering) by a Nanosizer (Malvern Zetasizer).

TABLE 15

Characterisation of droplets

| | Mean diameter | Polydispersity index | Zeta potential (mV) in water | Zeta Potential (mv) in PBS 0.1x |
|---|---|---|---|---|
| 3.25 mL | 54 | 0.119 | −3.51 | −3.3 |

D. Demonstrating Evidence of the ONH-POC Functions on the Surface of the LNP

In order to clearly demonstrate evidence of the presence of oxyamine functions protected on the surface of the LNP, a sample (0.6 mL, 3.96 mM, 2.38 µmol of —ONH—POC functions) was introduced into a flask, and then a few drops of NaOH were added therein in order to make the medium more basic (pH 9), which promotes the deprotection of the oxyamines under irradiation.

The size and the zeta potential of the particles were measured after irradiation so as to determine the effect of pH and of the light on the particles. The results are provided in the Table 16 here below.

It was found that the photo-deprotection of the —ONHPOC functions was achieved without significantly altering the size and surface charge of the nanoparticles.

TABLE 16

Size and zeta potential after deprotection of the oxyamine functions

| | Mean Diameter (nm) | Polydispersity index | Zeta Potential (mv) |
|---|---|---|---|
| SACONH-PEG100-ONHPPOC pH 7.4 | 54 | 0.119 | −3.3 |
| SACONH-PEG100-ONHPPOC pH 9; hv 10 min | 55 | 0.161 | −1.9 |

As the oxyamine functions (O—$NH_2$) react very quickly with the aldehyde functions, evidence of the formation of the —$ONH_2$ functions was demonstrated by means of reaction with the fluorescein-aldehyde having the formula given below (6.6 mM, 1.08 mL, 7.13 µmol).

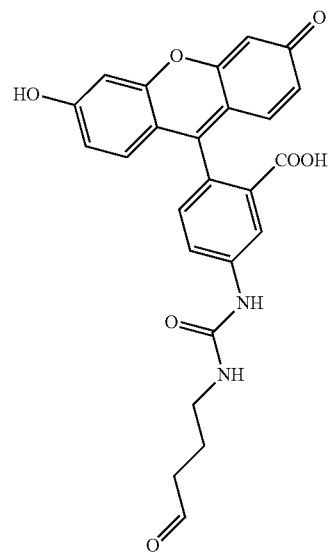 [SMILES: O=CCCCNC(=O)Nc1ccc(-c2c3ccc(=O)cc-3oc3cc(O)ccc23)c(C(=O)O)c1]

The two reagents were placed into contact with each other for 2 hour with stirring on a moving stir plate and protected from light. Then, purification by size exclusion column (Sephadex G-25 Medium, GE Healthcare) was performed in order to get rid of all the fluorescein molecules that have not reacted with the LNP-$ONH_2$ The elution fractions collected were analysed by fluorescence spectroscopy on a Tecan plate reader (Tecan Infinite M1000). Assays were performed in two wavelength ranges: 1) with excitation at 490 nm and collecting of the emission at 520 nm (signals due to the fluorescein of the fluorescein-CHO reagent); 2) with excitation at 640 nm and collecting of the emission at 690 nm (signals due to the DiD included in the core of the particles).

The protocol was repeated with an emulsion of LNP-Myrj S100 not bearing ONH-POC functions on their surface. Furthermore, the LNP-ONHPOC that were not irradiated and therefore not deprotected were brought to be reacted with the fluorescein-aldehyde in the same proportions as before. Finally, the protocol was repeated after having inhibited the oxyamine functions (—$ONH_2$) that were deprotected with acetone before putting them in contact with fluorescein-aldehyde.

It may be noted from the elution profiles obtained with the two types of droplets that —ONH-POC functions present on the surface of the droplets, that are irradiated and thus deprotected in order to access the O—$NH_2$ functions, were able to react with the aldehyde function of the aldehyde fluorescein fluorophore (co-elution of the fluorescein—grafted to the surface of the nanoparticles and of the DiD included within their core). However, no reactivity with respect to the fluorescein-aldehyde has been detected for the negative controls.

E. Gelling of the LNP-ONHPOC after Photo-Deprotection and Addition of Glutaraldehyde A quantity of 0.6 mL of the formulation of LNP-ONHPOC (3.66 mmol) as obtained here above was deprotected in the presence of NaOH (pH 9) by irradiation for 10 minutes at 365 nm (15 mW, OSRAM HBO 750MA lamp).

To this solution were added 2 .µL of a solution of glutaraldehyde 50% in water (that is 22 µmol and 10 equivalents of aldehyde functions relative to the —ONHPOC functions deprotected in —$ONH_2$). A change in colour—from blue to red- and the formation of a gel were noted.

The mechanism of the supposed gelation is illustrated in the diagram here below.

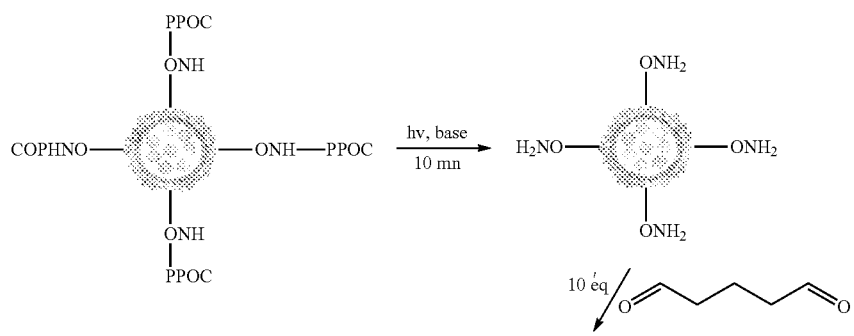

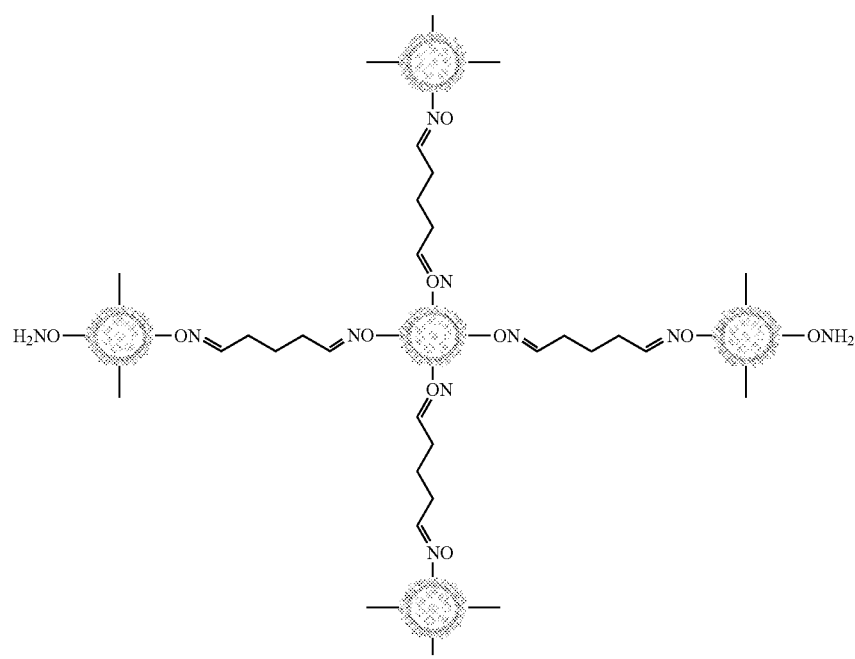

The change in colour observed during the irradiation step (deprotection of the oxyamine functions) is attributed to a degradation of the fluorophore DiD encapsulated in the core of the nanoparticles during the irradiation in basic medium.

The gel remains stable even after several hours after addition of the buffer PBS 1×, which demonstrates evidence of the production of a chemical gel.

Example 11

Formation of Gels with a Maleimide-Function Based Surfactant

A. Synthesis of SA-PEG-Maleimide

This is a PEG surfactant with 100 ethylene glycol units, one end of which is bound to the stearic acid (C18) by an amide bond, and the other end to a maleimide function by a second amide bond.

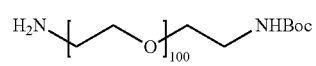

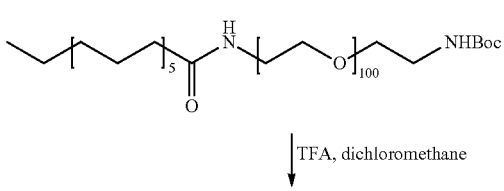

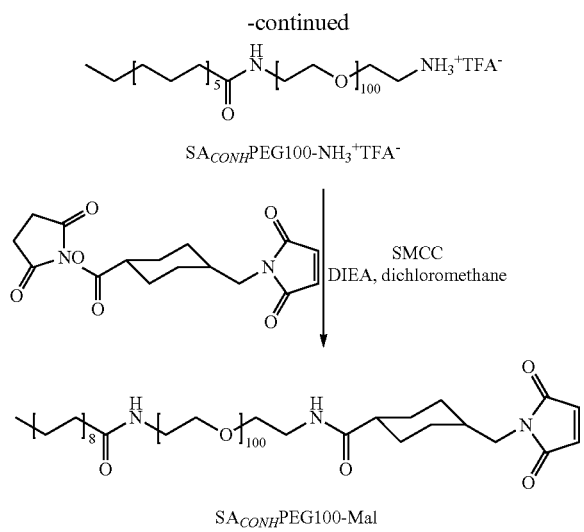

SA$_{CONH}$PEG100-NH$_3$$^+$TFA$^-$

↓ SMCC, DIEA, dichloromethane

SA$_{CONH}$PEG100-Mal

The synthesis of this compound is similar to that of the SA$_{CONH}$PEG100-SPDP (or SSPyr, surfactant LII in the Example 1). As illustrated in the diagram above, the common intermediate SA$_{CONH}$PEG100-NH$_3$$^+$TFA$^-$ (surfactant C in the Example 1), which is obtained in two steps (coupling of the PEG-NHBoc-NH$_2$ with the stearic acid and then deprotection of the Boc group), a nucleophilic substitution of the latter on the SMCC reagent ("maleimide-cyclohexane—NHS") results in the desired product SA$_{CONH}$PEG100-Malargon.

Synthesis of the Product SA$_{com}$PEG100-Mal

Under argon, the SA$_{CONH}$PEG100-NH$_3$$^+$TFA$^-$ (MW: 5191.44; 0.1 g; 0.02 mmol) and the diisopropylethylamine, DIEA (MW: 129.25; 5 µL; 2 eq; 0.04 mmol.) are dissolved in dichloromethane (2 mL). After 5 minutes under stirring, SMCC (MW: 334.32; 20 mg; 0.06 mmol; 3 eq) was added in the reaction medium. The disappearance of the amine was monitored by TLC (CH$_2$Cl$_2$/MeOH 9/1). After 1 hour of reaction and evaporation of the solvent, the product was precipitated two times in ether in order to give after filtration mg of SA$_{CONH}$PEG100-Mal (white powder).

TLC (CH$_2$Cl$_2$/MeOH 9/1) Rf=0.25

$^1$H NMR (300 MHz; CDCl$_3$): d: 0.88 (t; C$\underline{H}_3$—CH$_2$); 1.25 (m; C$\underline{H}_2$ stearate); 1.50 (m; C$\underline{H}_2$ of cyclohexane); 1.60 (m; C$\underline{H}_2$—CH$_2$—CONH); 1.9 (m; cyclo-C$\underline{H}$—CH$_2$—); 2.20 (t; C$\underline{H}_2$—CONH); 3.42 (m; C$\underline{H}_2$—NHCO); 3.45 (m; C $\underline{H}_2$-Mal); 3.48-3.8 (m; xC$\underline{H}_2$(PEG); C$\underline{H}_2$—NHCO); 6.11 (bt; NH); 6.70 (s; $\underline{HC}$=C$\underline{H}$ of maleimide)

B. Preparation of an Emulsion of Droplets of 50 nm (LNP-Maleimide 50)

An emulsion of droplets containing the surfactant SA$_{CONH}$PEG$_{100}$-maleimide were prepared with the composition indicated in the Table 17 here below, as described in the previous Example 7 for preparation of the oily phase, of the aqueous phase, mixing of the two phases and then sonication. The particles were purified by dialysis (MWCO 12-14 KDa) against PBS and diluted so as to obtain a mass fraction of 20%.

TABLE 17 composition of the LNP-maleimide 50

| | Mass (mg) | | | | |
|---|---|---|---|---|---|
| | Lipid Phase | | | Aqueous Phase | |
| Purified | Wax | Lecithin | | | |
| Soybean Oil | Suppocire NC | Lipoid s75 | Myrj ® S40 | SA$_{CONH}$PEG100-maleimide | PBS 1X |
| F 50 | | | | | |
| 68 | 272 | 65 | 276 | 69 | 2500 |

C. Preparation of an Emulsion of Droplets of 120 nm (LNP-Maleimide 120)

An emulsion of droplets containing the surfactant SA$_{CONH}$PEG$_{100}$-maleimide was prepared with the composition indicated in the Table 18 here below, as described in the previous Example 7 for preparation of the oily phase, of the aqueous phase, mixing of the two phases and then sonication. The droplets were purified by dialysis (MWCO 12-14 KDa) against PBS and diluted so as to obtain a mass fraction of 20%.

TABLE 18 composition of the LNP-maleimide F120

| | Mass (mg) | | | | |
|---|---|---|---|---|---|
| | Lipid Phase | | | Aqueous Phase | |
| Purified Soy- | Wax | Lecithin | | | |
| bean Oil | Suppocire NC | Lipoid s75 | Myrj ® S40 | SA$_{CONH}$PEG100-maleimide | PBS 1X |
| F 120 | | | | | |
| 450 | 150 | 45 | 172 | 43 | 1140 |

D. Formation of Gel from the LNP-Mal Emulsion and Cross-Linker SH-PEG-SH

An quantity of 100 mg of the LNP-mal emulsion prepared (500 µL of suspension of droplets measuring 120 nm or 50 nm in diameter) is brought to be reacted with 0.9 mg of poly(ethylene glycol) dithiol (weight average molecular weight 1000 Da) at ambient temperature with a thiol/maleimide ratio of 1:1. The mixture is placed under conditions of moderate stirring.

A gel begins to form within a few minutes after the mixing of the reagents.

Example 12

Formation of Photo-Cleavable Gels

A. Synthesis of the surfactant SA$_{CONH}$PEG100N—ONB-Maléimide

This is a polyethylene glycol type surfactant (100 Units) whose one end is bound to a fatty chain (C18) via an amide function and the other end has another amide function bound to a maleimide group via an ortho nitrobenzyl type (ONB) photocleavable group. Its structure and synthesis process diagram are detailed here below.

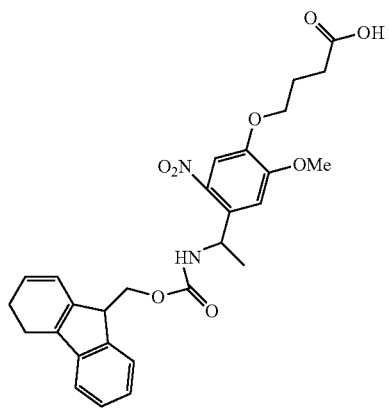
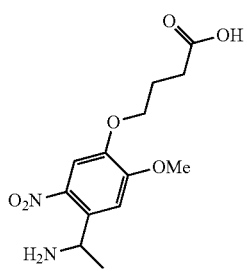
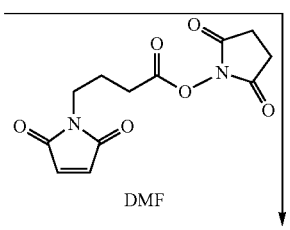
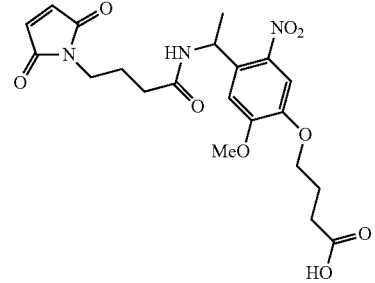
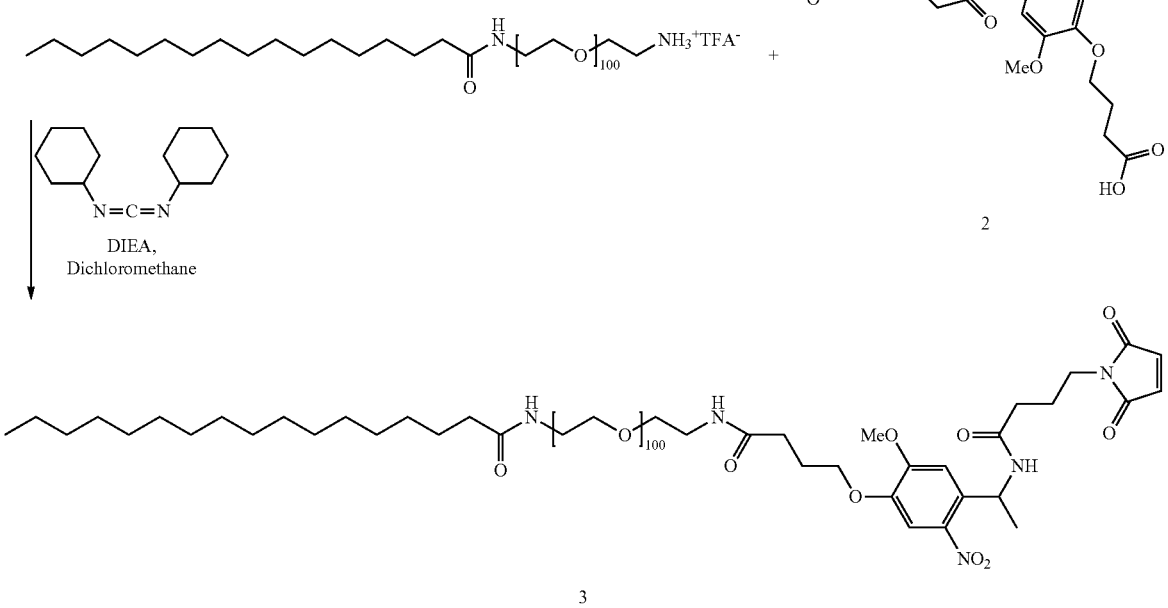

Synthesis of the Product 1

The Fmoc-Photo-Linker (950 mg, 1.82 mmol, supplier IRIS Biotech GmbH) was brought to be reacted with piperidine (237.26 .μL, 2.36 mmol) in 12 mL of dimethylformamide, DMF. Stirring conditions were maintained for a period of 3 hours under argon. The reaction medium was evaporated to dryness. The reaction was monitored by TLC using the eluent dichloromethane/methanol (9/1). The product 1 was obtained in the form of a yellow oil. The crude product was used as is in the subsequent step.

Summary of the Product 2

The product 1 was dissolved in dimethylformamide (15 mL) to which was added the 4-Maleimidobutyric acid N-hydroxysuccinimide ester (665.63 mg, 2.366 mmol). The mixture was stirred for a period of 3 hours under argon and the reaction was monitored by TLC: eluent: dichloromethane/methanol (9/1). After evaporation of the dimethylformamide, DMF, the crude product was purified by chromatography on silica gel (eluent: ethyl acetate and then dichloromethane/methanol 9/1). The product 2 was obtained in the form of a yellow oil (571.42 mg, 1.22 mmol, 67% yield from the two steps).

$^1$H-NMR (200 MHz, CDCl$_3$): ppm 1.51 (3H, d, CH$_3$); 1.89 (2H, m, N—CH$_2$—CH$_2$—CH$_2$); 2.05-2.21 (4H, m, NH—CO—CH$_2$ and O—CH$_2$—CH$_2$); 2.51 (2H, t, COOH—CH$_2$); 3.52 (2H, t, O—CH$_2$); 3.92 (3H, s, O—CH3); 4.11 (2H, t, N—CH$_2$); 5.52 (1H, m, CH—CH$_3$); 6.69 (2H, s, 2CH maleimide); 7-7.55 (2H$_{Ar}$, 2s); 8.02 (1H, NH).

MS (ESI positive mode): M$_{calc}$=463.44 (C$_{21}$H$_{25}$N$_3$O$_9$); m/z=486.2 [M+Na]$^+$ Synthesis of the Product 3

Under argon, the SA$_{CONH}$PEG100-NH$_3^+$TFA$^-$ (surfactant C in the Example 1, 165 mg, 0.033 mmol) and the diisopropylethylamine, DIEA (17.3 .μL, 0.1 mmol) were dissolved in dichloromethane (5 mL). After 5 minutes of stirring, the product 2 (47.62 mg, 0.1 mmol) and DCC (20 mg, 0.1 mmol) were added to the reaction medium. After a reaction period of 3 hours, the reaction mixture was precipitated in ether and purified by chromatography on silica gel. The product 3 was obtained in the form of a yellow powder.

$^1$H-NMR (200 MHz, CDCl$_3$): d ppm 0.88 (3H, t, CH$_3$); 1.07 (2H, m, CH$_2$—CH$_2$—CONH); 1.11 (2H, t, CH2-

CONH); 1.19 (28H, m, 14 CH2); 1.63 (2H, m, N—CH$_2$—CH$_2$—CH$_2$); 1.86 (3H, d, CH$_3$); 2.1-2.2 (6H, m, NH—CO—CH$_2$, O—CH$_2$—CH$_2$ and COOH—CH$_2$); 3.46 (2H, t, O—CH$_2$); 3.5-3.70 (400H, m, CH$_2$ PEG); 3.96 (3H, s, O—CH3); 4.11 (2H, t, N—CH$_2$); 5.14 (1H, m, CH—CH$_3$); 5.65 (2H, s, 2CH maleimide); 6.97-7.53 (2H$_{Ar}$, 2s); 8.32 (1H, NH).

B. Preparation of an Emulsion of Droplets of 50 nm (LNP ONB Maleimide 50)

An emulsion containing the surfactant SA$_{CONH}$PEG$_{100}$-ONB-maleimide was prepared with the composition indicated in the Table 19 here below, as described in the previous Example 7 for preparation of the oily phase, of the aqueous phase, mixing of the two phases and then sonication. The particles were purified by dialysis (MWCO 12-14 KDa) against PBS and diluted so as to obtain a mass fraction of 20%.

TABLE 19 composition of the LNP-ONB-maleimide 50

| Mass (mg) | | | | | |
|---|---|---|---|---|---|
| Lipid Phase | | | | Aqueous Phase | |
| Purified Soybean Oil | Wax Suppocire NC | Lecithin Lipoid s75 | Myrj ® S40 | SA$_{CONH}$PEG$_{100}$-ONB-maleimide | PBS 1X |
| F 50 | | | | | |
| 68 | 272 | 65 | 276 | 69 | 2500 |

C. Preparation of an Emulsion of Droplet of 120 nm (LNP ONB Maleimide 120)

An emulsion containing the surfactant SA$_{CONH}$PEG$_{100}$-maleimide was prepared with the composition indicated in the Table 20 here below, as described in the previous Example 7 for preparation of the oily phase, of the aqueous phase, mixing of the two phases and then sonication. The particles were purified by dialysis (MWCO 12-14 KDa) against PBS and diluted so as to obtain a mass fraction of 20%.

TABLE 20 composition of the LNP-ONB-maleimide F120

| Mass (mg) | | | | | |
|---|---|---|---|---|---|
| Lipid Phase | | | | Aqueous Phase | |
| Purified Soybean Oil | Wax Suppocire NC | Lecithin Lipoid s75 | Myrj ® S40 | SA$_{CONH}$PEG$_{100}$-ONB-maleimide | PBS 1X |
| F 120 | | | | | |
| 450 | 150 | 45 | 172 | 43 | 1140 |

D. Formation of Gel from the LNP-ONB-Mal Emulsion and the Cross-Linker SH-PEG-SH An quantity of 100 mg of the prepared emulsion (500 .μL of suspension, LNP formulation 120 nm or 50 nm) is brought to be reacted with 0.9 mg of poly(ethylene glycol) dithiol (weight average molecular weight 1000 Da) at ambient temperature with a thiol/maleimide ratio of 1:1. The mixture is placed under conditions of moderate stirring.

A gel begins to form within a few minutes after the mixing of the reagents. This gel is formed by means of the formation between particles of SA-PEG$_{5000}$-ONB-mal-S-PEG$_{1000}$-S-mal-ONB-PEG$_{5000}$-SA bonds.

E. Photo-Destruction of the Gel Formed from LNP-ONB-Mal and the Cross-Linker SH-PEG-SH The chemical gel formed earlier, which is held together by the bonds between particles of the type SA-PEG$_{5000}$-ONB-mal-S-PEG$_{1000}$-S-mal-ONB-PEG$_{5000}$-SA, is photocleavable by means of irradiation at 365 nm due to the presence of the group ONB.

What is claimed is:

1. A method for preparing a material comprising of a continuous aqueous phase and a dispersed phase, dispersed in the form of droplets containing a phospholipid and a surfactant having the following formula (I):

$$(L_1\text{-}X_1\text{—}H_1\text{—}Y_1)_v\text{-}G\text{-}(Y_2\text{—}H_2\text{—}X_2\text{-}L_2)_w \quad (I),$$

wherein:
  $L_1$ and $L_2$ are independently selected from among:
    a R or R—(C═O)— group, where R represents a linear hydrocarbon chain containing from 11 to 23 carbon atoms;
    an ester or an amide of fatty acids containing from 12 to 24 carbon atoms and of phosphatidyl ethanolamine;
    and a poly(propylene oxide);
  $X_1$, $X_2$, $Y_1$, and $Y_2$ are independently selected from among:
    a single bond;
    a Z group selected from among —O—, —NH—, —O(OC)—, —(CO)O—, —(CO)NH—, —NH(CO)—, —O—(CO)—O—, —NH—(CO)—O—, —O—(CO)—NH— and —NH—(CO)—NH—;
    a Alk group being an alkylene containing from 1 to 6 carbon atoms; and
    a Z-Alk, Alk-Z, Alk-Z-Alk or Z-Alk-Z group, where Alk and Z are as defined here above and where the two Z groups of the Z-Alk-Z group are identical or different;
  $H_1$ and $H_2$ are independently selected from a poly(ethylene oxide);
  G includes at least one G' group having one of the following formulas:

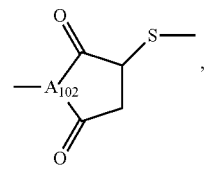

(XIV)

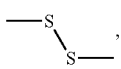

(XV)

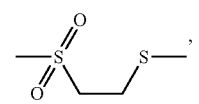

(XVI)

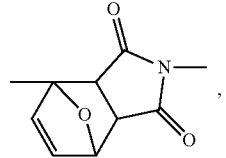

(XVII)

(XVIII)

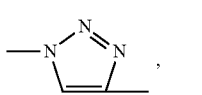

and (XVIIII)

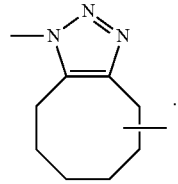

where $A_{102}$ represents CH or N; and
v and w are independently an integer from 1 to 8,
the said method comprising bringing into contact:
an emulsion 1 comprising a continuous aqueous phase and a dispersed phase, dispersed in the form of droplets containing an phospholipid and a surfactant having the following formula (LI):

$$L_1\text{-}X_1\text{—}H_1\text{—}Y_1\text{-}G_1 \quad (LI),$$

with an emulsion 2 comprising a continuous aqueous phase and a dispersed phase, dispersed in the form of droplets containing an phospholipid and a surfactant having the following formula (LII):

$$G_2\text{-}Y_2\text{—}H_2\text{—}X_2\text{-}L_2 \quad (LII)$$

where $G_1$ and $G_2$ are groups that are capable of reacting in order to form the G group,
under conditions that allow for the reaction of the surfactants having the formulas (LI) and (LII) in order to form the surfactant having the formula (I), whereby covalent bonds between the droplets of the dispersed phase are formed.

2. Method of preparation according to claim 1, wherein the reaction of $G_1$ and $G_2$ in order to form the G group is carried out by irradiation of the mixture formed by the emulsion 1 and the emulsion 2 by means of a light radiation.

3. Method of preparation according to claim 1, wherein the aqueous phase of the emulsion 1 and/or of the emulsion 2 has a pH comprised between 5.5 and 8.5.

4. A material obtainable by the method according to claim 1, comprising of a continuous aqueous phase and a dispersed phase, dispersed in the form of droplets bonded to each other in a covalent manner by the surfactant having the formula (I).

5. Material according to claim 4, wherein, in the formula (I), the radicals $L_1\text{-}X_1\text{—}H_1\text{—}$ and/or $L_2\text{-}X_2\text{—}H_2\text{—}$ consist of one of the groups having the following formulas:

(CI)

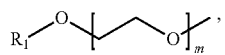

(CII)

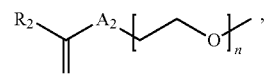

(CIII)

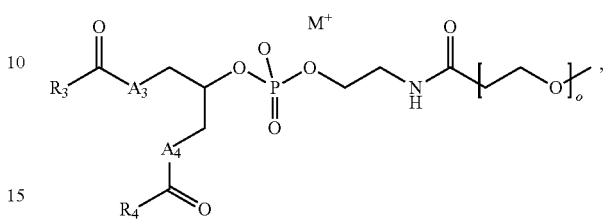

(CIV)

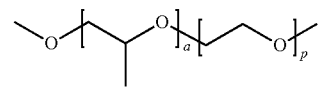

in which:
$R_1$, $R_2$, $R_3$ and $R_4$ independently represent a linear hydrocarbon chain containing from 11 to 23 carbon atoms,
$A_1$, $A_2$, $A_3$ and $A_4$ represent O or NH,
m, n, o and p independently represent integers from 3 to 500,
a represents an integer from 20 to 120,
M represent H or a cation.

6. Material according to claim 5, wherein the surfactant having the formula (I) has the following formula (I'):

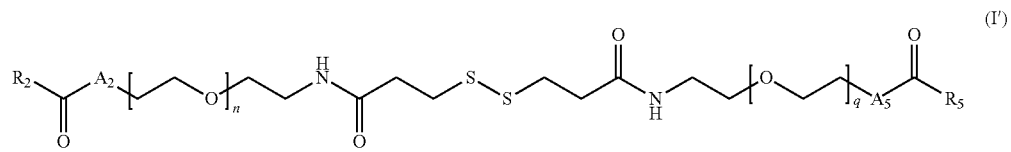

(I')

in which:
$R_2$ and $R_5$ independently represent a linear hydrocarbon chain containing from 11 to 23 carbon atoms,
$A_2$ and $A_5$ represent O or NH, and
n and q independently represent integers from 3 to 500.

7. Material according to claim 4, wherein, in the formula (I), the G group includes a cleavable function.

8. Material according to claim 4, comprising a solubilising lipid including at least one glyceride of fatty acids.

9. Material according to claim 4, comprising a co-surfactant containing a chain composed of units of ethylene oxide or of ethylene oxide and of propylene oxide.

10. Material according to claim 9, wherein the ratio of the mass of surfactant having the formula (I) over the mass of the ensemble (surfactant having the formula (I)/co-surfactant) is greater than or equal to 15%.

11. Material according to claim 4, wherein the zeta potential of the droplets in the aqueous phase is comprised between −20 mV and +20 mV.

12. Material according to claim 4, comprising an oil.

13. Material according to claim 4, comprising an agent of interest.

14. Material according to claim 13, wherein the agent of interest is a therapeutic agent.

15. Membrane or coating comprising the material according to claim 4.

16. Valve or mask for preparing biochips comprising the material according to claim 4.

17. Chemical detector or chemical sensor comprising the material according to claim 4.

18. Method for the delivery of an agent of interest by use of a material according to claim 13.

19. A method for preventing or treating a disease comprising administering to a human being or a mammal in need thereof an effective amount of the material according to claim 14, for its use for treating or preventing a disease.

\* \* \* \* \*